US012636522B2

(12) United States Patent
Sverdlik et al.

(10) Patent No.: US 12,636,522 B2
(45) Date of Patent: May 26, 2026

(54) CONTOUR-ADAPTIVE ULTRASOUND SYSTEM FOR FAT TISSUE TREATMENT

(71) Applicant: Sofwave Medical Ltd., Yokneam Illit (IL)

(72) Inventors: Ariel Sverdlik, Tel-Aviv (IL); Shimon Eckhouse, Haifa (IL); Assaf Gelstein, Haifa (IL)

(73) Assignee: Sofwave Medical Ltd., Yokneam Illit (IL)

( * ) Notice: Subject to any disclaimer, the term of this patent is extended or adjusted under 35 U.S.C. 154(b) by 0 days.

(21) Appl. No.: 19/314,663

(22) Filed: Aug. 29, 2025

(65) Prior Publication Data

US 2026/0021328 A1      Jan. 22, 2026

Related U.S. Application Data

(63) Continuation of application No. 18/887,103, filed on Sep. 17, 2024, which is a continuation of application
(Continued)

(51) Int. Cl.
| | |
|---|---|
| *A61N 7/02* | (2006.01) |
| *A61B 18/18* | (2006.01) |
| *A61N 7/00* | (2006.01) |

(52) U.S. Cl.
CPC ................ *A61N 7/02* (2013.01); *A61B 18/18* (2013.01); *A61N 2007/0008* (2013.01); *A61N 2007/0078* (2013.01)

(58) Field of Classification Search
CPC .............. A61N 7/02; A61N 2007/0008; A61N 2007/0078; A61N 2007/0073;
(Continued)

(56) References Cited

U.S. PATENT DOCUMENTS

| | | | |
|---|---|---|---|
| 4,101,795 A | 7/1978 | Fukumoto et al. | |
| 4,800,316 A | 1/1989 | Ju-Zhen | |

(Continued)

FOREIGN PATENT DOCUMENTS

| | | |
|---|---|---|
| CN | 1430538 | 7/2003 |
| CN | 101166472 | 4/2008 |

(Continued)

OTHER PUBLICATIONS

Hao "GridHub: A Grid-Based, High-Density Material Handling System", A Dissertation Submitted to the Faculty of the J.B. Speed School of Engineering of the University of Louisville in Partial Fulfillment of the Requirements for the Degree of Doctor of Philosophy in Industrial Engineering, Department of Industrial Engineering, University of Louisville, Kentucky, USA, Electronic Theses and Dissertations, Paper 3408: 1-197, May 2020.
(Continued)

*Primary Examiner* — Bo Joseph Peng
(74) *Attorney, Agent, or Firm* — Finnegan, Henderson, Farabow, Garrett & Dunner, LLP

(57) ABSTRACT

A system for treating fat tissue, including: an ultrasound applicator, including: two or more ultrasound transducers configured to generate and direct ultrasonic waves to a selected tissue volume including fat tissue; a control unit, including: a control circuitry electrically connected to the two or more ultrasound transducers, wherein the control circuitry is configured to activate the two or more ultrasound transducers to heat the selected tissue volume.

20 Claims, 32 Drawing Sheets

Related U.S. Application Data

No. 17/265,229, filed as application No. PCT/IL2019/050877 on Aug. 2, 2019, now Pat. No. 12,102,844.

(60) Provisional application No. 62/713,578, filed on Aug. 2, 2018.

(58) Field of Classification Search
CPC ...... A61N 2007/0095; A61N 2007/025; A61N 7/00; A61B 18/18; A61B 18/00
See application file for complete search history.

(56) References Cited

U.S. PATENT DOCUMENTS

| | | | |
|---|---|---|---|
| 5,139,496 A * | 8/1992 | Hed ...................... A61N 7/00 | |
| | | | 606/23 |
| 5,601,526 A | 2/1997 | Chapelon et al. | |
| 5,620,479 A | 4/1997 | Diederich | |
| 5,630,837 A | 5/1997 | Crowley | |
| 5,664,570 A | 9/1997 | Bishop | |
| 6,050,943 A | 4/2000 | Slayton et al. | |
| 6,126,619 A | 10/2000 | Peterson et al. | |
| 6,190,315 B1 * | 2/2001 | Kost ................. A61M 37/0092 | |
| | | | 600/309 |
| 6,589,174 B1 | 7/2003 | Chopra et al. | |
| 6,595,934 B1 | 7/2003 | Hissong et al. | |
| 6,605,043 B1 | 8/2003 | Dreschel et al. | |
| 7,582,050 B2 | 9/2009 | Schlorff et al. | |
| 7,828,734 B2 | 11/2010 | Azhari et al. | |
| 7,878,977 B2 | 2/2011 | Mo et al. | |
| 8,133,180 B2 | 3/2012 | Slayton et al. | |
| 8,183,745 B2 | 5/2012 | Trolier-Mckinstry et al. | |
| 9,737,434 B2 * | 8/2017 | Allison ..................... A61F 7/10 | |
| 10,194,526 B1 | 1/2019 | Simula et al. | |
| 11,241,218 B2 | 2/2022 | Emery et al. | |
| 2001/0029393 A1 | 10/2001 | Tierney et al. | |
| 2002/0115960 A1 * | 8/2002 | Redding, Jr. ..... A61M 37/0092 | |
| | | | 604/22 |
| 2003/0201696 A1 | 10/2003 | Muramatsu et al. | |
| 2003/0229331 A1 | 12/2003 | Brisken | |
| 2004/0039312 A1 | 2/2004 | Hillstead et al. | |
| 2004/0044375 A1 | 3/2004 | Diederich et al. | |
| 2004/0077977 A1 * | 4/2004 | Ella .................... A61H 23/0245 | |
| | | | 601/9 |
| 2004/0236375 A1 | 11/2004 | Redding, Jr. | |
| 2004/0267252 A1 | 12/2004 | Washington et al. | |
| 2005/0075573 A1 | 4/2005 | Park | |
| 2005/0075599 A1 * | 4/2005 | Redding ................. A61N 7/00 | |
| | | | 604/22 |
| 2005/0251235 A1 | 11/2005 | Schlorff et al. | |
| 2006/0089632 A1 | 4/2006 | Barthe et al. | |
| 2006/0094988 A1 | 5/2006 | Tosaya et al. | |
| 2007/0038156 A1 | 2/2007 | Rosenberg | |
| 2007/0055179 A1 | 3/2007 | Deem et al. | |
| 2007/0123764 A1 | 5/2007 | Thao et al. | |
| 2008/0045882 A1 | 2/2008 | Finsterwald | |
| 2008/0071255 A1 * | 3/2008 | Barthe ..................... A61B 8/08 | |
| | | | 606/9 |
| 2008/0139974 A1 | 6/2008 | Da Silva | |
| 2008/0183110 A1 * | 7/2008 | Davenport ............... A61N 7/02 | |
| | | | 601/3 |
| 2008/0195000 A1 * | 8/2008 | Spooner ............. A61H 23/0245 | |
| | | | 601/2 |
| 2008/0262482 A1 | 10/2008 | Hantash et al. | |
| 2008/0287839 A1 * | 11/2008 | Rosen .................... A61H 7/001 | |
| | | | 601/18 |
| 2009/0105588 A1 | 4/2009 | Emelianov et al. | |
| 2009/0171255 A1 * | 7/2009 | Rybyanets ............... A61N 7/02 | |
| | | | 601/3 |
| 2009/0182231 A1 | 7/2009 | Barthe et al. | |
| 2009/0221938 A1 * | 9/2009 | Rosenberg ............. A61N 1/328 | |
| | | | 601/2 |
| 2009/0312693 A1 * | 12/2009 | Thapliyal .......... A61M 37/0092 | |
| | | | 601/2 |

| | | | |
|---|---|---|---|
| 2010/0049186 A1 | 2/2010 | Ingle et al. | |
| 2010/0160782 A1 * | 6/2010 | Slayton ................ A61B 8/4483 | |
| | | | 601/3 |
| 2010/0168583 A1 | 7/2010 | Dausch | |
| 2011/0034833 A1 | 2/2011 | Chopra et al. | |
| 2011/0040213 A1 * | 2/2011 | Dietz ........................ B06B 3/00 | |
| | | | 601/2 |
| 2011/0112405 A1 * | 5/2011 | Barthe ................... A61B 8/467 | |
| | | | 600/459 |
| 2011/0166437 A1 | 7/2011 | Chang et al. | |
| 2011/0270137 A1 * | 11/2011 | Goren ..................... A61N 7/02 | |
| | | | 601/2 |
| 2011/0272179 A1 | 11/2011 | Vasoya | |
| 2012/0016239 A1 | 1/2012 | Barthe et al. | |
| 2012/0016273 A1 | 1/2012 | Diederich | |
| 2012/0029353 A1 | 2/2012 | Slayton et al. | |
| 2012/0065492 A1 | 3/2012 | Gertner et al. | |
| 2012/0095372 A1 | 4/2012 | Sverdlik et al. | |
| 2012/0136280 A1 | 5/2012 | Rosenberg et al. | |
| 2012/0226214 A1 | 9/2012 | Gurtner et al. | |
| 2012/0271294 A1 | 10/2012 | Barthe | |
| 2012/0310232 A1 | 12/2012 | Erez | |
| 2013/0012842 A1 | 1/2013 | Barthe | |
| 2013/0068382 A1 | 3/2013 | Harhen et al. | |
| 2013/0103028 A1 | 4/2013 | Tsoref et al. | |
| 2013/0134834 A1 | 5/2013 | Yoshikawa et al. | |
| 2013/0204167 A1 | 8/2013 | Sverdlik et al. | |
| 2013/0208572 A1 | 8/2013 | Klee et al. | |
| 2013/0245728 A1 | 9/2013 | Galen et al. | |
| 2014/0005521 A1 | 1/2014 | Koehler et al. | |
| 2014/0184022 A1 | 7/2014 | Kobayashi et al. | |
| 2014/0276055 A1 * | 9/2014 | Barthe ................. A61B 8/4466 | |
| | | | 600/439 |
| 2015/0079069 A1 | 3/2015 | Rozkov | |
| 2015/0165241 A1 | 6/2015 | Burdette | |
| 2015/0216719 A1 * | 8/2015 | DeBenedictis .......... A61N 7/00 | |
| | | | 607/108 |
| 2015/0216720 A1 * | 8/2015 | DeBenedictis ...... A61K 31/047 | |
| | | | 607/109 |
| 2015/0217141 A1 * | 8/2015 | Barthe ..................... A61N 7/00 | |
| | | | 601/2 |
| 2015/0283408 A1 | 10/2015 | Barthe et al. | |
| 2015/0319880 A1 | 11/2015 | Strickland et al. | |
| 2016/0016015 A1 | 1/2016 | Slayton et al. | |
| 2016/0036412 A1 | 2/2016 | Suzuki et al. | |
| 2016/0089550 A1 | 3/2016 | DeBenedictis et al. | |
| 2016/0310212 A1 | 10/2016 | Domankevitz | |
| 2017/0028227 A1 | 2/2017 | Emery et al. | |
| 2018/0161002 A1 | 6/2018 | Alford et al. | |
| 2018/0161016 A1 | 6/2018 | Choi et al. | |
| 2018/0264291 A1 | 9/2018 | Rem-Bronneberg et al. | |
| 2019/0001159 A1 | 1/2019 | Chen et al. | |
| 2019/0009111 A1 | 1/2019 | Myhr et al. | |
| 2019/0105520 A1 | 4/2019 | Sverdlik et al. | |
| 2019/0110357 A1 | 4/2019 | Gavagnin et al. | |
| 2019/0132983 A1 | 5/2019 | Weis et al. | |
| 2019/0142380 A1 | 5/2019 | Emery et al. | |
| 2019/0143149 A1 | 5/2019 | Sverdlik et al. | |
| 2019/0224501 A1 | 7/2019 | Burdette | |
| 2019/0254157 A1 | 8/2019 | Kotlar | |
| 2020/0287126 A1 | 9/2020 | Chang | |
| 2021/0252314 A1 | 8/2021 | Sverdlik et al. | |
| 2021/0298812 A1 | 9/2021 | Sverdlik et al. | |
| 2021/0339053 A1 | 11/2021 | Sverdlik et al. | |
| 2022/0008112 A1 | 1/2022 | Sverdlik et al. | |
| 2022/0015227 A1 | 1/2022 | Ogawa et al. | |
| 2022/0176167 A1 * | 6/2022 | Sverdlik ................ A61B 18/18 | |
| 2023/0345615 A1 | 10/2023 | Sverdlik et al. | |

FOREIGN PATENT DOCUMENTS

| | | |
|---|---|---|
| CN | 101232852 | 7/2008 |
| CN | 102098982 | 6/2011 |
| CN | 102958565 | 3/2013 |
| CN | 103371850 | 10/2013 |
| CN | 103987334 | 8/2014 |
| CN | 109475754 | 3/2019 |
| EP | 2629736 | 2/2017 |

(56) References Cited

FOREIGN PATENT DOCUMENTS

| | | |
|---|---|---|
| KR | 10-2018-0107832 | 10/2018 |
| WO | 9948621 A2 | 9/1999 |
| WO | WO00/45445 | 8/2000 |
| WO | WO 2006/114736 | 11/2006 |
| WO | WO 2010/029556 | 3/2010 |
| WO | WO 2013/033066 | 3/2013 |
| WO | WO 2014/022777 | 2/2014 |
| WO | WO 2016/090175 | 6/2016 |
| WO | WO 2015/106118 | 7/2017 |
| WO | WO 2017/212489 | 12/2017 |
| WO | WO 2018/035012 | 2/2018 |
| WO | WO 2020/026253 | 2/2020 |
| WO | WO 2020/026254 | 2/2020 |
| WO | WO 2020/194312 | 10/2020 |
| WO | WO 2021/111450 | 6/2021 |
| WO | WO 2022/144895 | 7/2022 |
| WO | WO 2023/089625 | 5/2023 |

OTHER PUBLICATIONS

Kim et al. "Sortation Control Using Multi-Agent Deep Reinforcement Learning in N-Grid Sortation System", Sensors, 20(12): 3401-l-3401-20, Jun. 16, 2020.
Seibold "Logical Time for Decentralized Control of Material Handling Systems", KIT Scientific Publishing, 1 P., 2016. Abstract.
Seibold et al. "Layout-Optimized Sorting of Goods With Decentralized Controlled Conveying Modules", 2013 IEEE International Systems Conference, SysCon, Orlando, FL, USA, Apr. 15-18, 2013, 6 P., Apr. 15, 2023.
Seibold et al. "Using Logical Time to Ensure Liveness in Material Handling Systems With Decentralized Control", IEEE Transactions on Automation Science and Engineering, 19(1): 545-552, Jan. 2022.
Communication Pursuant to Article 94(3) EPC Dated Sep. 4, 2023 from the European Patent Office Re. Application No. 19843063.9. (4 Pages).
Communication Pursuant to Article 94(3) EPC Dated May 23, 2023 from the European Patent Office Re. Application No. 17731653.6 (7 Pages).
Communication Pursuant to Article 94(3) EPC Dated May 24, 2024 from the European Patent Office Re. Application No. 19843063.9. (3 Pages).
Examination Report Dated Jun. 3, 2021 from the Australian Government, IP Australia Re. Application No. 2017278615. (5 Pages).
Examination Report Dated Nov. 30, 2021 from the Australian Government, IP Australia Re. Application No. 2017278615. (5 Pages).
Examination Report Dated Mar. 31, 2022 from the Australian Government, IP Australia Re. Application No. 2017278615. (3 Pages).
International Preliminary Report on Patentability Dated Oct. 7, 2021 from the International Bureau of WIPO Re. Application No. PCT/IL2020/050368. (8 Pages).
International Preliminary Report on Patentability Dated Feb. 11, 2021 from the International Bureau of WIPO Re. Application No. PCT/IL2019/050877. (13 Pages).
International Preliminary Report on Patentability Dated Feb. 11, 2021 from the International Bureau of WIPO Re. Application No. PCT/IL2019/050878. (10 Pages).
International Preliminary Report on Patentability Dated Jul. 13, 2023 from the International Bureau of WIPO Re. Application No. PCT/IL2021/051558 (12 Pages).
International Preliminary Report on Patentability Dated Jun. 16, 2022 from the International Bureau of WIPO Re Application No. PCT/IL2020/051252 (11 Pages).
International Preliminary Report on Patentability Dated Dec. 20, 2018 from the International Bureau of WIPO Re. Application No. PCT/IL2017/050638. (16 Pages).
International Search Report and the Written Opinion Dated Jan. 2, 2018 from the International Searching Authority Re. Application No. PCT/IL2017/050638. (26 Pages).

Notification of Office Action and Search Report Dated Sep. 2, 2020 From the China National Intellectual Property Administration Re. Application No. 201780044046.5 and Its Translation Into English. (10 Pages).
Notification of Office Action and Search Report Dated Nov. 6, 2023 From the National Intellectual Property Administration of the People's Republic of China Re. Application No. 202080039155.X and Its Machine Translation Into English. (26 Pages).
Notification of Office Action and Search Report Dated Nov. 9, 2023 From the National Intellectual Property Administration of the People's Republic of China Re. Application No. 202110669417.7 and Its Machine Translation Into English. (9 Pages).
Notification of Office Action and Search Report Dated Sep. 26, 2019 From the State Intellectual Property Office of the People's Republic of China Re. Application No. 201780044046.5. (10 Pages).
Requisition by the Examiner Dated May 15, 2023 From the Innovation, Science and Economic Development Canada, Canadian Intellectual Property Office Re. Application No. 3,026,107. (4 pages).
Supplementary European Search Report and the European Search Opinion Dated Apr. 12, 2022 From the European Patent Office Re. Application No. 19843063.9. (7 Pages).
Supplementary European Search Report and the European Search Opinion Dated Nov. 24, 2022 From the European Patent Office Re. Application No. 20776371.5 (9 pages).
Supplementary European Search Report and the European Search Opinion Dated Mar. 31, 2022 From the European Patent Office Re. Application No. 19844582.7. (9 Pages).
Third Party Observation Dated Aug. 11, 2023 Against Korea Republic Application No. 10-2021-7035100 and its Machine translation into English. (311 Pages).
Third Party Observation Dated Aug. 11, 2023 From the Korean Intellectual Property Office Re. Application No. 10-2021-7035100. (2 Pages).
Translation Dated Oct. 20, 2019 of Notification of Office Action Dated Sep. 26, 2019 From the State Intellectual Property Office of the People's Republic of China Re. Application No. 201780044046. 5. (8 Pages).
Translation Dated Sep. 21, 2020 of Notification of Office Action Dated Sep. 2, 2020 From the China National Intellectual Property Administration Re. Application No. 201780044046.5. (8 Pages).
DiBernardo "Evaluation of Skin Tightening After Laser-Assisted Liposuction", Aesthet Surg Journal 29(5):400-407, Sep./Oct. 2009.
Epoxy Technology et al. "EPO-TEK Adhesives Applications", Epoxy Technology Inc., XP055410092, Data Sheets, p. 1-16, Dec. 31, 2013. p. 3-5.
Lee at al. "Flexible Piezoelectric Micromachined Ultrasonic Transducer (pMUT) for Application in Brain Stimulation", Microsystem Technologies, 23: 2321-2328, Published: Apr. 29, 2016.
Lin et al. "Prediction of Heat-Induced Collagen Shrinkage by Use of Second Harmonic Generation Microscopy", Journal of Biomedical Optics 11)3):034020-1-6, May 1, 2006.
Lumenis® "Fem Touch™ Presentation", Lumenis® —Energy to Healthcare, CD-2003696 Rev. F, 40 P., 2018.
Massachusetts Institute of Technoloy "PDMS-MIT", 6.777J/2.751J Material Property Database, Massachusetts Institute of Technology, 2020.
Paul et al. "Three-Dimensional Radiofrequency Tissue Tightening: A Proposed Mechanism and Applications for Body", Aesthetic Plastic Surgery, 35(1):87-95, Sep. 11, 2010.
Tadir "International Update on Genitourinary Devices", ASLMS 2018, 38th Annual Conference of the American Society for Laser Medicine and Surgery, Dallas, TX, USA, Apr. 11-15, 2018, Poster Presentation, 20 P., Apr. 11, 2018.
Tadir et al. "Light and Energy Based Therapeutics for Genitourinary Syndrome of Menopause: Consensus and Controversies", Lasers in Surgery and Medicine, 49(2): 137-159, Published Online Feb. 21, 2017.
Wei et al. "Short-Term Effects of Radiofrequency Shrinkage Treatment for Anterior Cruciate Ligament Relaxation on Proprioception", Journal of International Medical Research, 41(5):1586-1593, Aug. 23, 2013.

(56)        References Cited

OTHER PUBLICATIONS

Yasui et al. "Observation of Dermal Collagen Fiber in Wrinkled Skin Using Polarization-Resolved-Second-Harmonic-Generation Microscopy", Optics Express, 17(2): 912-923, Jan. 19, 2009.

International Search Report and the Written Opinion Dated Jun. 2, 2020 From the International Searching Authority Re. Application No. PCT/IL2020/050368. (36 Pages).

International Search Report and the Written Opinion Dated Mar. 2, 2023 From the International Searching Authority Re. Application No. PCT/IL2022/051243 (12 Pages).

International Search Report and the Written Opinion Dated Mar. 14, 2021 From the International Searching Authority Re. Application No. PCT/IL2020/051252 (16 Pages).

International Search Report and the Written Opinion Dated Jan. 22, 2020 From the International Searching Authority Re. Application No. PCT/IL2019/050877 (25 Pages).

International Search Report and the Written Opinion Dated Nov. 26, 2019 From the International Searching Authority Re. Application No. PCT/IL2019/050878 (17 Pages).

International Search Report and the Written Opinion Dated Apr. 27, 2022 From the International Searching Authority Re. Application No. PCT/IL2021/051558 (17 Pages).

Invitation to Pay Additional Fees and Communication Relating to the Results of the Partial International Search Dated Feb. 8, 2021 From the International Searching Authority Re. Application No. PCT/IL2020/051252. (4 Pages).

Invitation to Pay Additional Fees Dated Nov. 13, 2019 From the International Searching Authority Re. Application No. PCT/IL2019/050877 (2 Pages).

* cited by examiner

| Identifying fat tissue layer | 764 |
| Determining boundaries of fat tissue layer | 766 |
| Adjusting treatment parameters | 768 |

F = 2 MHz, I = 30 w/cm^2, 8 sec

F = 2 MHz, I = 30 w/cm^2, 13 sec

F = 2 MHz, I = 10 w/cm^2, 37 sec

F = 2 MHz, I = 10 w/cm^2, 42 sec

F = 5 MHz, I = 16 w/cm^2, 6 sec

F = 5 MHz, I = 16 w/cm^2, 11 sec

Fig. 13C
Fig. 13D
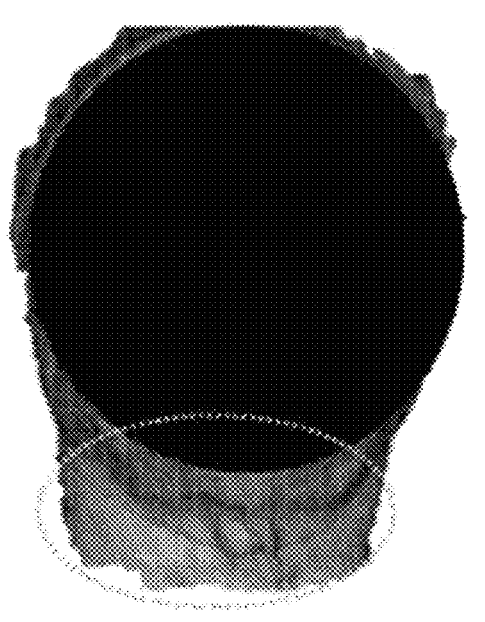
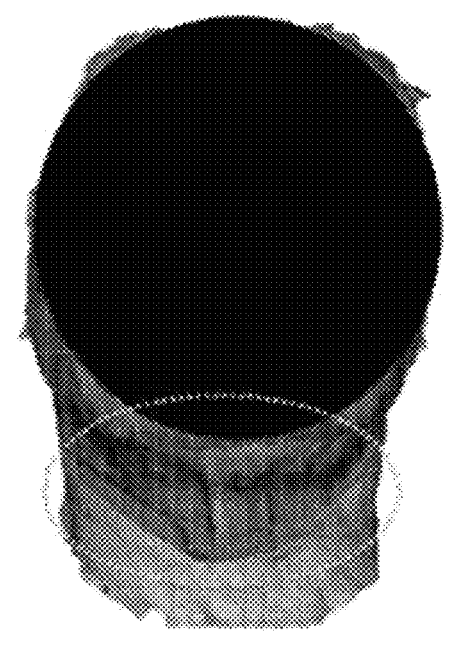

CONTOUR-ADAPTIVE ULTRASOUND SYSTEM FOR FAT TISSUE TREATMENT

RELATED APPLICATION/S

This application is a continuation of U.S. patent application Ser. No. 18/887,103, filed on Sep. 17, 2024, which is a continuation of U.S. patent application Ser. No. 17/265,229, filed on Feb. 2, 2021 (now U.S. Pat. No. 12,102,844, issued Oct. 1, 2024), which is a National Phase of PCT Patent Application No. PCT/IL2019/050877 having International Filing Date of Aug. 2, 2019, which claims the benefit of priority under 35 USC § 119(e) of U.S. Provisional Patent Application No. 62/713,578 filed on Aug. 2, 2018. The contents of the above applications are all incorporated by reference as if fully set forth herein in their entirety.

FIELD AND BACKGROUND OF THE INVENTION

The present invention, in some embodiments thereof, relates to fat tissue treatment, for example a cosmetic fat tissue treatment and, more particularly, but not exclusively, to fat tissue treatment using ultrasonic energy.

SUMMARY OF THE INVENTION

Following are some examples of some embodiments of the invention:

Example 1. A system for treating fat tissue, comprising: an ultrasound applicator, comprising:

two or more ultrasound transducers configured to generate and direct ultrasonic waves to a selected tissue volume comprising fat tissue;

a control unit, comprising:

a memory;

a control circuitry electrically connected to said two or more ultrasound transducers, wherein said control circuitry is configured activate said two or more ultrasound transducers in alternation and/or intermittently according to indications stored in said memory.

Example 2. A system according to example 1, wherein said control circuitry activates said two or more ultrasound transducers according to an activation sequence stored in said memory.

Example 3. A system according to any one of examples 1 or 2, wherein said ultrasound applicator comprises a housing having an inner lumen and at least one opening through a surface of said housing.

Example 4. A system according to example 3, wherein an ultrasound energy emitting surface of said two or more ultrasound transducers face at least partly said opening.

Example 5. A system according to any one of examples 3 or 4, wherein said ultrasound applicator comprises a vacuum opening in said inner lumen, and wherein said vacuum opening is connected to a low-pressure source.

Example 6. A system according to example 5, wherein said control unit is configured to activate said low-pressure source for generating low-pressure levels within said inner lumen of the applicator during the activation of said two or more ultrasound transducers.

Example 7. A system according to any one of the previous examples, wherein said ultrasound applicator comprises at least one cooling element attached to said two or more transducers, wherein said cooling element is configured to cool a skin layer of a tissue contacting the two or more ultrasound transducers.

Example 8. A system according to example 7, wherein said at least one cooling element comprises at least one TEC, and wherein a cold surface of said TEC is attached to a surface of each of said at least two ultrasound transducers or to a surface of at least one thermal conducting transducer holder attached to the two or more transducers.

Example 9. A system according to example 7, wherein said ultrasound applicator comprises at least one cooling chamber comprising cooling liquid, wherein a hot surface of said at least one TEC is attached to a surface of said at least one cooling chamber, or to a surface of a thermal conductive adaptor positioned between said hot surface of said TEC and said at least one cooling chamber.

Example 10. A system according to any one of the previous examples, wherein said ultrasonic waves are unfocused ultrasonic waves.

Example 11. A system according to any one of the previous examples, wherein said control circuitry signals said two or more ultrasound transducers to generate said ultrasonic waves in frequency values in a range of 1-10 MHz.

Example 12. A system according to any one of the previous examples, wherein said control circuitry signals said two or more ultrasound transducers to generate said ultrasonic waves with intensity values of 5-90 W/cm^2.

Example 13. A method for treating fat tissue, comprising:

delivering ultrasonic waves in alternation from at least two spaced-apart locations on the skin towards a selected tissue volume in a tissue, wherein said selected tissue volume comprises fat tissue;

cooling said skin during said delivery.

Example 14. A method according to example 13, comprising:

deforming a portion of said tissue during said delivering.

Example 15. A method according to example 14, wherein said deforming comprises applying vacuum on said tissue.

Example 16. A method according to any one of examples 13 to 15, comprising heating said fat tissue to a temperature of at least 52° C.

Example 17. A method according to any one of examples 13 to 16, comprising generating said ultrasonic waves with frequency values in a range of 1-10 MHz.

Example 18. A method according to example 17, wherein said generating comprises generating said ultrasonic waves with frequency and/or intensity parameter values sufficient for penetrating into a depth of at least 4 mm into said tissue.

Example 19. A method according to any one of examples 13 to 18, wherein said ultrasonic waves are unfocused ultrasonic waves.

Example 20. An assembly comprising:

an ultrasound transducer having a body with a first surface and a second surface, and at least one channel crossing through said body from said first surface and said second surface;

a cooling element attached to said first surface of said body, wherein said cooling element is configured to cool a tissue contacting said second surface through said at least one channel.

Example 21. An assembly according to example 20, wherein said at least one channel comprises a thermal conductive material connecting said cooling element and said tissue.

Example 22. An assembly according to any one of examples 20 or 21, comprising a flex PCB attached to said second surface of said ultrasound transducer.

Example 23. An assembly according to example 22, wherein said flex PCB comprises one or more temperature sensors positioned within said at least one channel.

Following are some additional examples of some embodiments of the invention:

Example 1. A system for treating fat tissue, comprising: an ultrasound applicator, comprising:

two or more ultrasound transducers configured to generate and direct ultrasonic waves to a selected tissue volume comprising fat tissue;

a control unit, comprising:

a control circuitry electrically connected to said two or more ultrasound transducers, wherein said control circuitry is configured to activate said two or more ultrasound transducers to heat said selected tissue volume.

Example 2. A system according to example 1, wherein said control circuitry activates said two or more ultrasound transducers in alternation and/or intermittently.

Example 3. A system according to any one of examples 1 or 2, wherein ultrasonic waves generated by said two or more ultrasound transducers converge in said selected tissue volume.

Example 4. A system according to any one of the previous examples, wherein said two or more ultrasound transducers are positioned at an angle smaller than 180 degrees relative to each other.

Example 5. A system according to any one of the previous examples wherein said control circuitry signals said two or more ultrasound transducers to generate said ultrasonic waves with intensity and/or frequency parameter values suitable to penetrate to a depth of at least 4 mm into said tissue volume.

Example 6. A system according to any one of the previous examples, wherein said control circuitry signals said two or more transducers to generate said ultrasonic waves with intensity and/or parameter values suitable to heat said tissue volume to at least 52° C. for a time period of at least 15 seconds.

Example 7. A system according to example 1, comprising a memory, wherein said control circuitry activates said two or more ultrasound transducers according to an activation sequence stored in said memory.

Example 8. A system according to any one of the previous example, wherein said ultrasound applicator comprises a housing having an inner lumen and at least one opening through a surface of said housing.

Example 9. A system according to example 8, wherein an ultrasound energy emitting surface of said two or more ultrasound transducers face at least 10% of said opening.

Example 10. A system according to any one of example 8 or 9, wherein said ultrasound applicator comprises a vacuum opening in said inner lumen, and wherein said vacuum opening is connected to a low-pressure source.

Example 11. A system according to example 10, wherein said control unit is configured to activate said low-pressure source for generating low-pressure levels within said inner lumen of the applicator during the activation of said two or more ultrasound transducers.

Example 12. A system according to any one of the previous examples, wherein said ultrasound applicator comprises at least one cooling element attached to said two or more transducers, wherein said cooling element is configured to cool a skin layer of a tissue contacting the two or more ultrasound transducers.

Example 13. A system according to example 12, wherein a temperature of said cooling element is in a range of −15° C. to −5° C.

Example 14. A system according to any one of examples 12 or 13, wherein said at least one cooling element comprises at least one TEC, and wherein a cold surface of said TEC is attached to a surface of each of said at least two ultrasound transducers or to a surface of at least one thermal conducting transducer holder attached to the two or more transducers.

Example 15. A system according to example 14, wherein said ultrasound applicator comprises at least one cooling chamber comprising cooling liquid, wherein a hot surface of said at least one TEC is attached to a surface of said at least one cooling chamber, or to a surface of a thermal conductive adaptor positioned between said hot surface of said TEC and said at least one cooling chamber.

Example 16. A system according to example 7, wherein said control circuitry is configured to activate said two or more ultrasound transducers according to indications related to a thickness of said fat tissue layers stored in said memory.

Example 17. A system according to example 1, comprising a memory, and wherein said control circuitry is configured to activate said two or more ultrasound transducers with activation parameters stored in said memory selected not to heat tissue layers adjacent in a depth direction to said fat tissue layer Example 18. A system according to example 17, wherein said activation parameters comprise one or more of ultrasonic waves frequency, ultrasonic waves intensity, ultrasonic waves angles, number of pulses of said ultrasonic waves, duration of each pulse of said ultrasonic waves, number of pulses per day, overall ultrasonic energy per day, desired temperature at said selected tissue volume.

Example 19. A system according to any one of the previous examples, wherein said ultrasonic waves are unfocused ultrasonic waves.

Example 20. A system according to any one of the previous examples, wherein said control circuitry signals said two or more ultrasound transducers to generate said ultrasonic waves in frequency values selected from a range of 1-10 MHz.

Example 21. A system according to any one of examples 1 to 19, wherein said control circuitry signals said two or more ultrasound transducers to generate said ultrasonic waves in frequency values selected from a range of 10-13 Mhz.

Example 22. A system according to any one of the previous examples, wherein said control circuitry signals said two or more ultrasound transducers to generate said ultrasonic waves with intensity values selected from a range of 5-90 W/cm^2. Example 23. A system according to any one of examples 1 to 21, wherein said control circuitry signals said two or more ultrasound transducers to generate said ultrasonic waves with intensity values selected from a range of 3-6 Joules.

Example 24. A system according to any one of the previous examples, wherein said control circuitry signals said two or more ultrasound transducers to generate and direct ultrasonic waves to a selected tissue volume in the Chin and/or the Neck.

Example 25. A system according to any one of the previous examples, wherein said control circuitry signals said two or more ultrasound transducers to generate and direct ultrasonic waves to a selected tissue volume in the Abdomen and/or Chest.

Example 26. A system according to any one of the previous examples, wherein said control circuitry signals said two or more ultrasound transducers to generate and direct ultrasonic waves to a selected tissue volume in the Thighs and/or hands.

Example 27. A system according to example 7, wherein said control circuitry is configured to activate said two or more ultrasound transducers with activation parameter values or indications thereof stored in said memory, selected to penetrate up to 7 mm from an external surface of the skin into said fat tissue.

Example 28. A system according to example 7, wherein said control circuitry is configured to activate said two or more ultrasound transducers with activation parameter values or indications thereof stored in said memory, selected not to heat muscle layer located deeper than said selected tissue volume.

Example 29. A method for treating fat tissue, comprising:

delivering ultrasonic waves from at least two spaced-apart locations on the skin towards a selected tissue volume in a tissue, wherein said selected tissue volume comprises fat tissue; cooling said skin during and/or prior to said delivery.

Example 30. A method according to example 29, wherein said delivering comprises delivering said ultrasonic waves in alternation from said at least two spaced-apart locations on the skin towards said selected tissue volume.

Example 31. A method according to any one of examples 29 or 30, comprising:

deforming a portion of said tissue during said delivering.

Example 32. A method according to example 31, wherein said deforming comprises applying vacuum on said tissue.

Example 33. A method according to any one of examples 29 to 32, comprising heating said fat tissue to a temperature of at least 52° C. for at least 5 seconds.

Example 34. A method according to any one of examples 29 to 33, comprising generating said ultrasonic waves with frequency values selected from a range of 1-10 MHz.

Example 35. A method according to any one of examples 29 to 33, comprising generating said ultrasonic waves with frequency values selected from a range of 10-13 MHz.

Example 36. A method according to any one of examples 29 to 35, comprising sensing fat tissue from at least one of said two spaced-apart locations on the skin.

Example 37. A method according to example 36, comprising adjusting angles of said ultrasonic waves according to said sensed location of said fat tissue.

Example 38. A method according to any one of example 36 or 37, comprising generating said ultrasonic waves with frequency and/or intensity values according to said determined depth of said fat tissue.

Example 39. A method according to any one of example 34 or 35, wherein said generating comprises generating said ultrasonic waves with frequency and/or intensity parameter values sufficient for penetrating into a depth of at least 4 mm into said tissue.

Example 40. A method according to any one of examples 29 to 39, comprising evaluating an effect of said delivering on said skin during and/or following said delivering.

Example 41. A method according to example 40, wherein said effect comprises at least one side effect, and wherein said method comprises adjusting one or more of intensity, frequency and duration of said ultrasonic waves to reduce said at least one side effect.

Example 42. A method according to any one of examples 29 to 41, wherein said ultrasonic waves are unfocused ultrasonic waves.

Example 43. A method according to any one of examples 29 to 42, wherein said method is applied to healthy subjects not suffering from a functional problem.

Example 44. An assembly comprising:

an ultrasound transducer having a body with a first upper surface and a second lower surface, and at least one channel crossing through said body from said first upper surface to said second lower surface;

a cooling element attached to said first upper surface of said body, wherein said cooling element is configured to cool a tissue contacting said second lower surface through said at least one channel.

Example 45. An assembly according to example 44, wherein said at least one channel comprises a thermal conductive material connecting said cooling element and said tissue.

Example 46. An assembly according to any one of examples 44 or 45, comprising an electrical circuitry attached to said second lower surface of said ultrasound transducer.

Example 47. An assembly according to example 46, wherein said electrical circuitry comprises one or more temperature sensors positioned within said at least one channel.

Example 48. A method for delivery of skin treatment, comprising:

selecting a treatment target for an ultrasound treatment located at a layer of the skin, wherein said ultrasound treatment is an unfocused ultrasound treatment;

adjusting values of one or more ultrasound treatment parameters according to said selected treatment target to avoid damage to a different layer of the skin;

delivering said ultrasound treatment to said treatment target.

Example 49. A method according to example 48, wherein said selecting comprises selecting two or more treatment targets for an ultrasound treatment located at different layers of the skin, and wherein adjusting comprises adjusting values of a one or more ultrasound treatment parameters according to said selected two or more treatment targets, wherein parameter values of an ultrasound treatment for treating a first treatment target of said two or more treatment targets are different from parameter values of an ultrasound treatment for treating a second treatment target of said two or more treatment targets;

Example 50. A method according to example 49, wherein said two or more treatment targets are located at one or more of epithelium layer, epidermis layer, hypodermis layer and lamina propria layer.

Example 51. A method according to any one of examples 48 to 50, wherein said one or more ultrasound treatment parameters comprise one or more of ultrasound waves frequency, ultrasound waves intensity, time period of ultrasound waves delivery.

Example 52. A method for targeting a fat tissue layer within skin, comprising;

determining a location of said fat tissue layer within said skin tissue;

calculating one or more of intensity, frequency and time duration values of unfocused ultrasonic waves to heat said fat tissue layer at said determined location without heating tissue layers located deeper than said fat tissue layer.

Example 53. A method according to example 52, wherein said determining comprises determining a thickness of said fat tissue layer and/or location of said deeper tissue layers.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as controlling the activation of ultrasound transducers to heat a deep layer of fat tissue, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2C and 2D are schematic illustrations of different treatment regions of the human body, according to some exemplary embodiments of the invention;

FIG. 7H is a schematic cross-section illustrations of skin layers, for example skin layers related to cellulite treatment, according to some exemplary embodiments of the invention;

FIGS. 10A-10E, 11A-11D, 12A-12D, 13A-13D are images of face regions before and after treatment delivered during an experiment;

Figure 1:
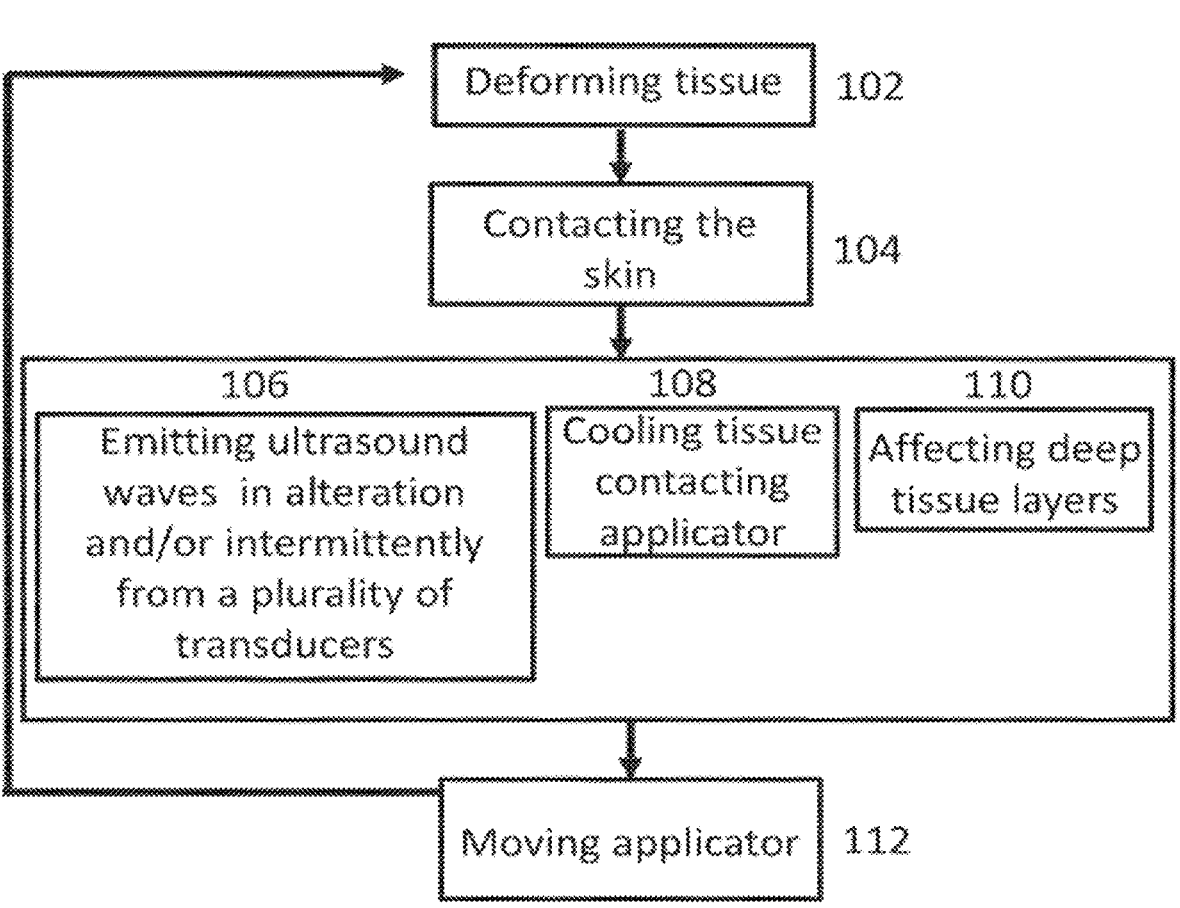
FIG. 1 is a is a flow chart of a general process for treating tissue, according to some exemplary embodiments of the invention.

Table A summarized treatment parameter values when emitting ultrasonic waves in a frequency of 2 MHZ, according to some exemplary embodiments of the invention; and Table B summarizes treatment parameter values when emitting ultrasonic waves in a frequency of 5 MHz, according to some exemplary embodiments of the invention.

DESCRIPTION OF SPECIFIC EMBODIMENTS OF THE INVENTION

The present invention, in some embodiments thereof, relates to fat tissue treatment, for example a cosmetic fat tissue treatment and, more particularly, but not exclusively, to fat tissue treatment using ultrasonic energy.

An aspect of some embodiments relates to heating a selected tissue volume comprising fat tissue located under the skin by a plurality of ultrasonic waves, for example unfocused ultrasonic waves, directed towards the selected tissue volume. As used herein the term unfocused means non-converging. In some embodiments, unfocused ultrasonic waves are ultrasonic waves, which are not focused to converge in two dimensions. In some embodiments, fat tissue comprises cellulite. In some embodiments, the ultrasonic waves are generated by two or more ultrasound transducers operating in alternation optionally in a repeated or a non-repeated sequence, for example to continuously heat the tissue volume while keeping the skin contacting the transducers cool. Alternatively or additionally, the ultrasonic waves are generated by intermittently activating one or more ultrasound transducers.

According to some embodiments, at least some of the ultrasonic waves cross each other. In some embodiments, the crossing point is located in the selected tissue volume. In some embodiments, the ultrasonic waves are emitted with a shift of at least 1° from a line of sight. Optionally, the ultrasonic waves are emitted with a shift of at least 1° from a line of sight relative to other ultrasonic waves.

According to some embodiments, at least some of the ultrasonic waves contact the selected tissue volume at spaced apart contact points positioned at a distance of up to 20 cm from each other, for example up to 10 cm, up to 5 cm, up to 2 cm, up to 0.1 cm or any intermediate, smaller or larger value, in the selected tissue volume.

According to some embodiments, the selected tissue volume has a maximal dimension value, for example maximal length, maximal width, maximal diameter, maximal thickness of up to 25 cm, for example up to 20 cm, up to 10 cm, up to 1 cm, up to 0.1 cm or any intermediate smaller or larger value.

According to some embodiments, the ultrasonic waves are generated by two or more ultrasound transducers positioned on top the skin. In some embodiments, the two or more ultrasound transducers are in direct contact with the skin. Alternatively, the two or more ultrasound transducers transmit the ultrasonic waves through a cover placed in direct contact with the skin.

According to some embodiments, the ultrasonic waves directed to the selected tissue volume are generated with intensity and frequency levels sufficient to affect the structure and/or stability of the fat tissue. In some embodiments, the ultrasonic waves heat the fat tissue to temperature levels in a range of 45-85° C., for example to temperature levels in a range of 45-55° C., 52-57° C., 50-70° C., 60-85° C., or any intermediate smaller or larger temperature value or range of temperatures. In some embodiments and without being bound by any theory, heating the fat tissue to these temperature levels causes death of adipose tissue, and specifically apoptosis of fat cells due to the heating. Optionally the heating causes damage to the micro-vasculature that supply blood to the fat cells, thus causing them to die. Optionally, during the heating of the fat tissue, the epidermis layer remains in a temperature level of up to 55° C.

According to some embodiments, the two or more ultrasound transducers generate ultrasonic waves in a frequency range of 1-10 MHz, for example, in a frequency range of 1-5 MHz, 3-7 MHz, 5-10 MHz or any intermediate, smaller or larger value or range of values.

According to some embodiments, the two or more ultrasound transducers generate ultrasonic waves in an intensity range of 5-90 W/cm^2, for example 5-20 W/cm^2, 10-30 W/cm^2, 40-90 W/cm^2 or any intermediate, smaller or larger value or range of values. In some embodiments, the two or more transducers deliver energy in a range of 1-18 Joules to the tissue.

According to some embodiments, the two or more ultrasound transducers generate high ultrasonic energy levels in the target tissue volume, with optionally lower energy levels on the skin surface. In some embodiments, the two or more ultrasound transducers generate the ultrasonic waves with low frequency, for example frequency values in a range of 1-5 MHz, for example, frequency values in a range of 1-2 MHZ, 2-4 MHZ, 3-5 MHz or any intermediate, smaller or larger range of values. In some embodiments, the low frequency ultrasonic waves allow deeper penetration into the tissue with less absorption in dermis and fascia. In some embodiments, the low frequency ultrasonic waves generate, for example, cavitation. In some embodiments, the cavitation is used, for example, to increase the ultrasonic energy absorption of the tissue.

According to some embodiments, the two or more ultrasound transducers generate the ultrasonic waves with higher frequency levels, for example, frequency levels in a range of 4-10 MHz, for example frequency levels in the range of 4-5 MHZ, 5-6 MHZ, 6-10 MHz or any intermediate, smaller or larger range of values. In some embodiments and without being bound by any theory, the high frequency ultrasonic waves intensify the absorption of the ultrasonic energy within the tissue, and optionally the heating of the tissue.

According to some embodiments, each ultrasound transducer generates ultrasonic waves with different frequencies, for example differences in a range of 0.1-2 MHZ. In some embodiments, the generated ultrasonic waves with the different frequencies allow to create acoustic beats. In some embodiments and without being bound by any theory, the acoustic beats allow, for example, to generate a low frequency that is half of the difference between the original two frequencies, and frequency that is the average of the original two frequencies. The low frequency can generate cavitation, which enhances absorption of ultrasonic energy in the tissue volume which is applied by the two frequencies.

According to some embodiments, one or more of a plurality of the ultrasound transducers are activated at a given time. In some embodiments, ultrasonic waves generated by the plurality of ultrasound transducers are directed towards the same tissue volume, which includes fat tissue. In some embodiments, at least two ultrasound transducers facing the tissue volume are activated for a pre-determined time before switching to different ultrasound transducers, for example at least two different ultrasound transducers of the same ultrasound applicator. In some embodiments, one or more ultrasound transducers of the applicator, facing the tissue volume, are intermittently activated. In some embodiments, an ultrasound energy emitting surface of said one or more ultrasound transducers faces the tissue volume. Alternatively or additionally, two or more ultrasound transducers of the applicator are activated in alternation, optionally in a repeated or a non-repeated sequence.

According to some embodiments, the activation period of each group of transducers is determined based on the temperature of the skin near the transducers, for example to minimize thermal damage of the skin. In some embodiments, activating different ultrasound transducers optionally groups of transducers in a sequence, one after the other, allows for example, to minimize thermal damage to the skin while continuously heating the deep tissue volume. In addition, it allows more efficient cooling of deactivated transducers.

According to some embodiments, each transducer or a group of transducers, for example 2 transducers, 3 transducers, 4 transducers or any larger number of transducers deliver a sequence of ultrasonic energy pulses to the tissue volume. In some embodiments, each transducer or a group of transducers are activated with zero emission windows between activation sequences. In some embodiments, during the delivery of the ultrasonic energy to the issue volume, some of the transducers, for example one or more of the transducers are deactivated while other transducers, for example one or more of the transducers are activated.

According to some embodiments, intermittently activating one or more transducers and/or activating the transducers in alternation allows for example, to cool thick transducers, for example thick piezoelectric (PZT) plates of the transducers. As used herein, the term PZT relates to any piezo-electric material that is used to generate ultrasound. In some embodiments, the thick PZT plates are cooled by a cool surface of a cooling element, for example the cool surface of a thermoelectric cooler (TEC). In some embodiments, cooling down the PZT plates allows, for example, to cool down the epidermis layer placed in contact with the ultrasound transducers.

According to some embodiments, the tissue is deformed into a desired geometrical shape while delivering the ultrasonic energy to the tissue volume. In some embodiments, the tissue is deformed, for example to ensure a better contact between the ultrasound transducers and the tissue. Alternatively or additionally, the tissue is deformed, for example, to better align the ultrasound transducer and the target tissue volume located deep inside the tissue.

According to some embodiments, the tissue is deformed by pressure applied by a mechanical assembly, for example clamps. In some embodiments, the tissue is held between two clamps, optionally comprising one or more transducers placed between the clamps ad the tissue.

According to some embodiments, the tissue is deformed by applying negative pressure, for example vacuum, on the tissue. As used herein, the term vacuum refers to pressure levels, which are lower than atmospheric pressure. In some embodiments, a negative pressure outlet tube is positioned near the tissue surface. In some embodiments, application of vacuum causes the tissue to bend through one or more openings in the ultrasound applicator, optionally without contacting an opening of the negative pressure outlet tube.

According to some embodiments, vacuum is stably applied on the tissue. In some embodiments, vacuum application during ultrasound energy delivery causes stretching of the skin. In some embodiments, stretching of the skin during ultrasound energy delivery increases thermal damage effect on collagen fibers in the tissue. In some embodiments, vacuum application allows, for example, to press the skin against the external face of the ultrasonic transducers. In some embodiments, pressing the skin against the transducers allows to minimize the general thickness of the tissue. Alternatively or additionally, pressing the skin against the transducers allows better acoustic contact and/or better thermal contact between the transducers and the tissue.

According to some embodiments, the tissue is vibrated during the delivery of the ultrasonic energy to the issue volume. In some embodiments, the tissue is vibrated by a vibrator attached to the applicator. Alternatively, the tissue is vibrated by applying vacuum intermittently. Optionally, the tissue is vibrated by changing levels of the negative pressure applied on the tissue.

According to some embodiments, the tissue vibration stretches and/or elongates collagen fibers in the tissue. Alternatively or additionally, the vibration decreases tissue perfusion, which optionally increases ultrasonic tissue heating.

An aspect of some embodiments relates to delivery of ultrasonic energy to a tissue volume using one or more ultrasound transducers having one or more cross through openings, for example cross-through channels. In some embodiments, the ultrasonic energy is delivered using the one or more ultrasound transducers while cooling layers of the skin, for example the epidermis layer of the skin. In some embodiments, tissue volume is a deep tissue volume and optionally comprises fat tissue. In some embodiments the one or more cross-through openings, for example one or more cross-through channels, crossing through a PZT plate of the one or more ultrasound transducers. Optionally, the one or more cross-through channels cross the PZT plate from one surface to another surface of the PZT plate.

According to some embodiments, a cooling element, for example a cool surface of a TEC and/or a surface of a cooling basement attached to a first surface of the one or more ultrasound transducers cool the skin contacting a second surface of the one or more transducers through the channels. In some embodiments, the channels are filled at least partly with a thermal conducting material, for example Aluminum, Iron, Copper, Silver, Gold, Alumina past.

According to some embodiments, the filled channels form cooling pillars between the cooling element and the skin. In some embodiments, the thermal conducting material in the cooling pillars conducts cold from the first surface to the second surface of the one or more transducers. In some embodiments, at least some of the cooling pillars comprise thermal isolators, for example to control the cooling level of the skin and optionally to avoid over cooling of the skin. In some embodiments, conducting cold through the cooling pillars allows, for example, to protect the epidermis layer of the skin from over-heating during the delivery of the ultrasonic energy. Alternatively or additionally, conducting cold through the cooling pillars allows, for example, to cool the dermis in order to avoid extensive continuous thermal damage.

According to some embodiments, a flex printed circuit board (PCB), optionally a thin flex PCB, comprising one or more thermistors configured to measure epidermal temperature, is attached to the second surface of the transducers. Optionally, the one or more thermistors are positioned within the channels. In some embodiments, the one or more thermistors are positioned within the cooling pillars.

According to some embodiments, the one or more channels are filled with a plurality of heat conducting materials, at different heat conductivity constants, for example Aluminum, Iron, Copper, Silver, Gold, Alumina past, positioned on the cooling plate. Alternatively or additionally, the one or more channels are filled with multi-layered stacks of materials positioned on the cooling plate. In some embodiments, the materials are used for cooling the tissue and/or for cooling the PZT.

According to some embodiments, the one or more crossing-through channels are empty. In some embodiments, the empty channels allow, for example, to apply vacuum on the skin surface through the channels. In some embodiments, applying vacuum through the channels allows, for example, better acoustic and/or better thermal contact with the skin.

According to some embodiments, a flex PCB, optionally a flex thin PCB, comprising one or more thermistors is attached to the second surface of the ultrasound transducer. In some embodiments, the one or more thermistors are positioned within the empty channels and are configured to measure temperature levels of the skin contacting the ultrasound transducer. In some embodiments, temperature measurements using the thermistors allows, for example, to protect the skin layers, for example the epidermis from over-heating and/or over cooling. Alternatively and/or additionally, measurements through the empty channels allow, for example, evaluation of acoustic and thermal contact with the skin.

According to some embodiments, having an ultrasound transducer with crossing-through channels, allows, for example to avoid overheating of the epidermis in temperature pick points on the PZT surface.

A potential advantage of using an ultrasound transducers with channels is that it allows to use thick ultrasound transducers, which generate ultrasonic energy with high intensity while controlling and/or cooling the temperature of the skin through the opening as abovementioned.

According to some embodiments, the applicator is connected to one or more fixtures and/or set-ups, configured to allow stand-alone positioning of the applicator against the skin. In some embodiments, the fixtures comprise at least one elastic band, for example at least one clastic band shaped and sized for positioning around the torso or a limb. In some embodiments, the one or more fixtures comprise at least one external elongated arm connected on one end to a system console, and configured to hold a plate with several treatment heads, for example several ultrasound applicators. In some embodiments, one or more vacuum cups are connected to the applicator head, for example to attach the vacuum head to the skin.

An aspect of some embodiments relates to targeting a fat tissue layer of the skin with ultrasonic energy. In some embodiments, the fat tissue layer is targeted by determining a depth of the fat tissue layer from the external surface of the skin. Additionally, the fat tissue layer is targeted by determining boundaries location of the fat tissue layer with upper and lower tissue layers contacting the fat tissue layer, for example a dermis layer and a muscle layer.

According to some embodiments, the fat tissue layer is targeted based on an anatomical location, and an average depth of the fat tissue layer from the external surface of the skin at the anatomical location. In some embodiments, the anatomical position comprises the Chin, left Neck, right Neck, Submental space, inner Thigh, outer Thigh, Buttocks, Chest and Abdomen. In some embodiments, by selecting a specific anatomical location, a depth, for example an average depth, of the fat tissue layer is determined. Optionally, by selecting a specific anatomical location, a width of the tissue layer, for example an average width of the fat tissue layer and/or location of the fat tissue layer boundaries at the specific anatomical location are determined. In some embodiments, treatment parameter values, for example ultrasonic waves intensity, ultrasonic waves frequency, ultrasonic waves angles, number and/or duration of ultrasonic waves pulses are adjusted, optionally automatically by a control unit of an ultrasound applicator based on the selected anatomical position.

According to some exemplary embodiments, the fat tissue layer is targeted, for example by scanning tissue layers for example deep tissue layers underneath a selected position on the external surface of the skin. In some embodiments, a scanner, for example an ultrasound scanner or an ultrasound probe is positioned at a selected position on the external surface of the skin, and scans deep tissue layers. In some embodiments, the fat tissue layer, and/or fat tissue boundaries with adjacent tissue layers are identified in the scans. In some embodiments, a depth, and/or a width of the fat tissue layer at the selected position on the external surface of the skin are calculated based on the scans. In some embodiments, location of the fat tissue layer boundaries with adjacent tissue layers are calculated based on the scans. In some embodiments, treatment parameter values, for example ultrasonic waves intensity, ultrasonic waves frequency, ultrasonic waves angles, number and/or duration of ultrasonic waves pulses are adjusted based on the scans.

An aspect of some embodiments relates to delivery of ultrasonic energy to one or more deep tissue layers of the skin for treating cellulite. In some embodiments, the delivered ultrasonic energy, for example unfocused ultrasonic energy, disrupts the deep tissue layers formation by heating deep tissue layers to a desired temperature level while cooling the external surface of the skin. In some embodiments, the deep tissue layers comprise fat tissue layer and/or connective tissue, for example connective tissue between fat cells.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary General Treatment Process

According to some exemplary embodiments, ultrasonic energy is directed from one or more ultrasound transducers of an ultrasound applicator towards a selected tissue volume, optionally comprising fat tissue. In some embodiments, in order to ensure close contact between the ultrasound applicator and the tissue, the tissue is deformed during the delivery of the ultrasonic energy. In some embodiments, deformation of the tissue, presses the tissue against the ultrasound transducer and/or against a surface of the applicator. In some embodiments, the ultrasound energy is delivered to the selected tissue volume by two or more ultrasound transducers that are activated intermittently and/or in alternation, for example to ensure continuous heating of the tissue volume while cooling the skin contacting a temporary inactive ultrasound transducer. Alternatively, the two or more ultrasound transducer work simultaneously, for example during more than 30% of their activation period. Reference is now made to FIG. 1 depicting a general process for treating deep tissue layers, according to some exemplary embodiments of the invention.

According to some exemplary embodiments, a selected target tissue is deformed at 102. In some embodiments, the tissue is deformed by applying negative pressure, for example vacuum on the tissue. Alternatively or additionally, the tissue is deformed by pressing an ultrasound applicator with a distorted external surface, for example with a curved external surface, against the tissue.

According to some exemplary embodiments, at least part of the ultrasound applicator is placed in contact with the skin at 104. In some embodiments, deforming the tissue at 102 allows, for example, a close contact between one or more ultrasound transducers of the ultrasound applicator and the skin. Alternatively or additionally, deforming the tissue at 102 allows, for example, to align one or more ultrasound transducers with a selected tissue volume within the selected target tissue.

According to some exemplary embodiments, ultrasound waves are emitted by activating two or more ultrasound transducers in alternation and/or intermittently, towards the selected tissue volume at 106. In some embodiments, the ultrasound waves are emitted from one or more ultrasound transducers while other ultrasound transducers of the applicator are temporary inactive. In some embodiments, the ultrasound waves are emitted while the tissue is at least partly deformed.

According to some exemplary embodiments, the tissue contacting the applicator and/or one or more of the transducers of the applicator is cooled in a timed relationship with the emitting of ultrasound waves, at 108. In some embodiments, the tissue contacting the applicator, for example the skin and/or the epidermis layer of the skin is cooled at 108. In some embodiments, the tissue contacting the transducer is cooled during and/or after the delivery of ultrasonic energy to the tissue. In some embodiments, the tissue contacting the transducer is cooled through one or more openings in the transducer. Alternatively or additionally, the tissue contacting the transducer is cooled by at least one cooling element, for example a TEC and/or a thermal conducting element attached to the one or more of the transducers.

According to some exemplary embodiments, the emitted ultrasound waves heat deep tissue layers at 110. In some embodiments, the deep tissue layers are heated to a temperature level in a range of 45-85° C., for example to a temperature level the range of 45-55° C., 52-57° C., 56-70° C., 65-85° C. or any intermediate, smaller or larger range of temperatures. In some embodiments, the deep tissue layers are positioned at a depth of 1-30 mm, for example at a depth of 2-20 mm, 5-30 mm or any intermediate, smaller or larger value, from the skin. In some embodiments, the deep tissue layers comprise fat tissue. In some embodiments and without being bound by any theory, heating fat tissue to a temperature in a range of 45-85° C., for example to a temperature range of 45-75° C., 52-57° C., 53-85° C. or any intermediate, smaller or larger range of temperatures, causes lipolysis of the fat tissue.

According to some exemplary embodiments, the applicator is moved to a different region on the skin at 112. In some embodiments, the applicator is moved to a different location when tissue deformation and/or emitting of ultrasound waves is stopped. Optionally, the applicator is moved to a different region when the ultrasound waves are emitted during a pre-determined time period. Alternatively or additionally, the applicator is moved when temperature levels at the contact site between the transducers and the skin are higher than a pre-determined temperature level, for example above 37° C., for example above 42° C.

Exemplary System for Treating Fat Tissue

Figure 2A:
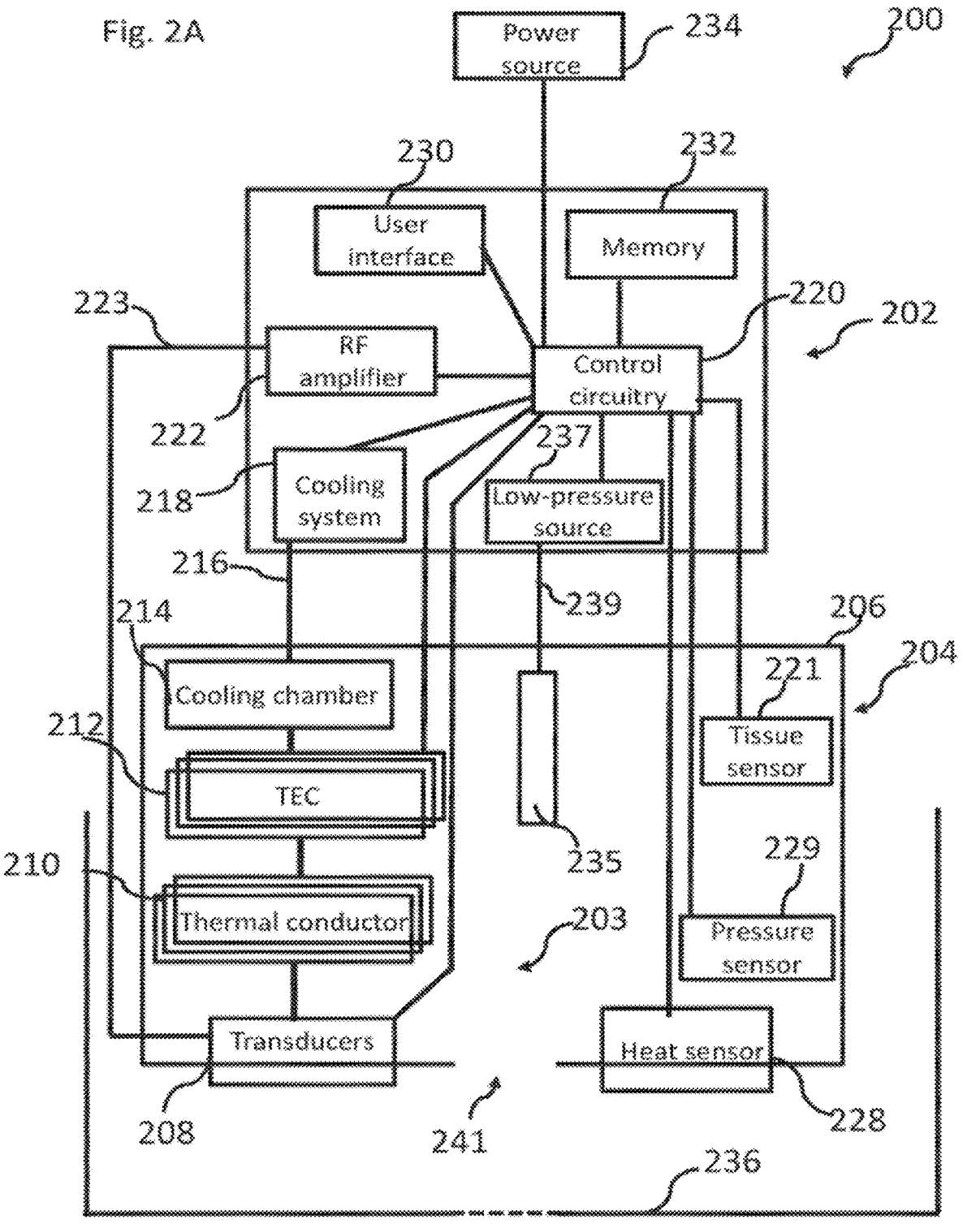
FIG. 2A is a block diagram of a system for delivery of ultrasonic energy treatment, according to some exemplary embodiments of the invention.

Reference is now made to FIG. 2A, depicting a system for treating a selected tissue volume comprising fat tissue, according to some exemplary embodiments of the invention.

According to some exemplary embodiments, a system for treating fat tissue, for example system 200 comprises a control console, for example control unit 202 and at least one ultrasound applicator, for example applicator 204. In some embodiments, applicator 204 comprises one or more ultrasound transducers, for example transducers 208 located at least partly within housing 206 of the applicator. In some embodiments, at least part of the transducers 208 extends out from the housing 206. In some embodiments, the transducers are spaced-apart and are distributed on the surface of the applicator. In some embodiments, each transducer of transducers 208 has a surface area in a range of 2×2 mm-20×20 mm, for example 5×5 mm, 10×10 mm or any intermediate, smaller or larger value.

According to some exemplary embodiments, the ultrasound applicator, for example applicator 204, has a maximal dimension, for example length or diameter in a range of 20-200 mm, for example in a range of 20-100 mm, 50-150 mm, 100-200 mm or any intermediate, smaller or larger value or range of values. In some embodiments, the ultrasound applicator, for example applicator 204 has a thickness in a range of 10-200 mm, for example in a range of 10-100 mm, 50-150 mm, 100-200 mm or any intermediate, smaller or larger value or range of values.

According to some exemplary embodiments, at least some transducers of transducers 208 have a transducer assembly comprising a PZT and one or more electrical connections. Optionally, the transducer assembly comprises at least one coating, for example coating of the PZT. In some embodiments, a thickness of the transducer assembly is in a range of 0.1-7 mm, for example in a range of 0.1-0.8 mm, 0.3-2 mm, 0.3-5 mm or any intermediate, smaller or larger value or range of values. In some embodiments, a thickness of a PZT is in a range of 0.1-5 mm, for example in a range of 0.1-2 mm, 0.2-3 mm, 0.5-5 mm or any intermediate, smaller or larger value or range of values.

According to some exemplary embodiments, the applicator 204 comprises at least one thermal conducting element. In some embodiments, the transducers 208 are attached to the at least one thermal conducting element, for example thermal conductor 210. In some embodiments, a surface of the one or more transducers 208 is attached to a surface of the thermal conductor 210. In some embodiments, a single thermal conductor is attached to two or more transducers. In some embodiments, the thermal conductor 210 is made from a thermal conductive material, for example Aluminum or Copper.

According to some exemplary embodiments, the applicator 204 comprises at least one cooling element, for example TEC 212. In some embodiments, a cold surface of the TEC is attached to a surface of the thermal conductor 210. Alternatively, a cold surface of the TEC is attached to the one or more ultrasound transducers 208. In some embodiments, the thermal conductor delivers cold from the cold surface of the TEC to the one or more transducers, optionally through the thermal conductor 210. In some embodiments, the TEC, for example TEC 212 has a surface area in a range of 10×10 mm-50×50 mm, for example 20×20 mm, 40×20 mm or any intermediate, smaller or larger surface area.

According to some exemplary embodiments, the applicator 204 comprises a cooling chamber, for example cooling chamber 214. In some embodiments, the cooling chamber 214 comprises cooling liquid, for example water. In some embodiments, the cooling chamber 214 is fluidically connected to a cooling system in the console by tubing 216. In some embodiments, the cooling chamber 214, for example a surface of the cooling chamber 214 is attached to a hot surface of the TEC 212. In some embodiments, heat is conducted from the hot surface of TEC 212 to the cooling liquid in the cooling chamber 214. In some embodiments, the cooling liquid is circulated between the cooling chamber 214 and the cooling system 218 of the control unit 202 via tubing 216.

According to some exemplary embodiments, the applicator 204 comprises at least one inlet of a low pressure source, for example inlet 235. In some embodiments, the inlet is connected to a low-pressure source 237, for example a vacuum pump in the control unit 202. Alternatively, the low-pressure source 237 is external to the control unit 202. In some embodiments, the low pressure source 237 is configured to generate negative pressure within lumen 203 of the applicator 204 by air suction through the inlet 235. In some embodiments, housing 206 comprises one or more openings, for example opening 241 at a surface facing a tissue. In some embodiments, suction of air through the inlet 235 causes penetration of tissue through the opening 241, optionally firmly attaching tissue penetrating into lumen 203 against the transducers 208.

According to some exemplary embodiments, the control unit 202 comprises at least one control circuitry, for example control circuitry 220. In some embodiments, the control circuitry 220 is electrically connected to memory 232, which stores indications of values and/or values related to activation parameters of the system 200. Alternatively or additionally, the memory 232 stored log files of the system. In some embodiments, the memory 232 stores at least one treatment protocol and/or parameters thereof.

According to some exemplary embodiments, the control circuitry 220 is electrically connected to the one or more transducers 208 of the applicator 204. In some embodiments, the control circuitry 220 controls the activation, for example intermittent and/or alternating activation, of the transducers 208 according to indications stored in memory 232. In some embodiments, the control circuitry 220 activates two or more or the transducers 208 in alternation according to a sequence stored in memory 232. In some embodiments, the control circuitry activates a transducer or a group of transducers of transducers 208 while other transducers and inactive. In some embodiments, the control circuitry deactivates the active transducer or the active group of transducers and activates at least one different ultrasound transducer or a different group of transducers directed to the same tissue volume.

According to some exemplary embodiments, the control circuitry 220 is electrically connected to the low-pressure source 237, for example the vacuum pump. In some embodiments, the control circuitry activates the low-pressure source 237 prior-to activating the transducers 208, for example to increase the attachment between the tissue and the transducers 208. In some embodiments, the applicator comprises at least one pressure sensor, for example pressure sensor 229, electrically connected to the control circuitry 220. In some embodiments, the pressure sensor 229 is configured to measure the pressure levels in the lumen 203 of the applicator 204. In some embodiments, the control circuitry adjusts the low pressure levels applied by the low pressure source 237 based on signals received from the pressure sensors 229. Alternatively or additionally, the control circuitry adjusts the low pressure levels applied by the low pressure source based on indications stored in the memory 232.

According to some exemplary embodiments, the applicator 204 comprises at least one heat sensor, for example heat sensor 228 electrically connected to the control circuitry 220. In some embodiments, the heat sensor is a thermistor. In some embodiments, the heat sensor 228 is configured to sense the temperature levels of the skin, optionally at the contact site between the transducers and the tissue. In some embodiments, the control circuitry 220 controls the activation of the cooling system 218, for example the circulation of the cooling liquid between the applicator and the cooling system, based on signals received from the heat sensor 228. In some embodiments, if the temperature of the tissue contacting at least one active transducer is higher than 40° C., for example higher than 42° C., then the control circuitry 220 increases the circulation of the cooling liquid. Alternatively or additionally, the control circuitry 220 signals the TEC to increase the cooling of the transducers.

According to some exemplary embodiments, the control circuitry 220 is electrically connected to the transducers 208 and/or to a RF amplifier, for example RF amplifier 223. In some embodiments, if the temperature of the tissue contacting at least one active transducer is higher than 40° C., for example higher than 42° C., then the control circuitry deactivates the at least one active transducer, for example to allow cooling of the tissue. Additionally or optionally, the control circuitry activates a different transducer or a group of different transducers, for example for continuous heating of the selected tissue volume.

According to some exemplary embodiments, the control unit 202 comprises at least one user interface, for example user interface 230. In some embodiments, the user interface 230 is configured to generate at least one human detectable indication, for example a light indication and/or a sound indication. In some embodiments, the control circuitry 220 signals the user interface 230 to generate an alert signal if the temperature level of the tissue, for example, the tissue contacting the transducers and/or the applicator is higher than a pre-determined value. Alternatively or additionally, the control circuitry 220 signals the user interface 230 to generate a human detectable indication when a treatment session at a selected tissue target ends.

According to some exemplary embodiments, the user interface 230 is configured to receive input from a user of the system 200. In some embodiments, the user input comprises at least one treatment protocol or parameters thereof. Alternatively or additionally, the user input comprises vacuum parameters values and/or values of ultrasonic energy parameters, for example intensity and/or frequency values.

According to some exemplary embodiments, the system 200 comprises a cover 236. In some embodiments, the cover 236 is shaped and sized to prevent direct contact between the transducers 208 and the tissue, optionally the tissue penetrating through opening 241 into the lumen 203. In some embodiments, the cover 236 allows, for example, to maintain sterility of the applicator 204.

According to some exemplary embodiments, the system 200 comprises a tissue sensor 221, for example a tissue detection sensor, electrically connected to the control circuitry 220. In some embodiments, the tissue detection sensor is configured to detect tissue type and/or cellular composition of the tissue, for example percentage of fat cells in the tissue. In some embodiments, the tissue detection sensor is configured to detect cellulite. Optionally, the tissue detection sensor detects cellulite by sensing texture changes in the skin, for example by sensing the presence of dimples in the skin.

According to some exemplary embodiments, the control circuitry 220 adjusts the parameter values of ultrasound waves generated by the transducers 208, for example, frequency and intensity values, according to signals received from the tissue sensor 221. In some embodiments, the control circuitry 220 signals the transducers 208 to generate ultrasound waves with intensity and frequency values suitable for treating cellulite, based on signals received from the tissue sensor 221.

Exemplary Spatial Relationship Between Transducers and Tissue Volume

Figure 2B:
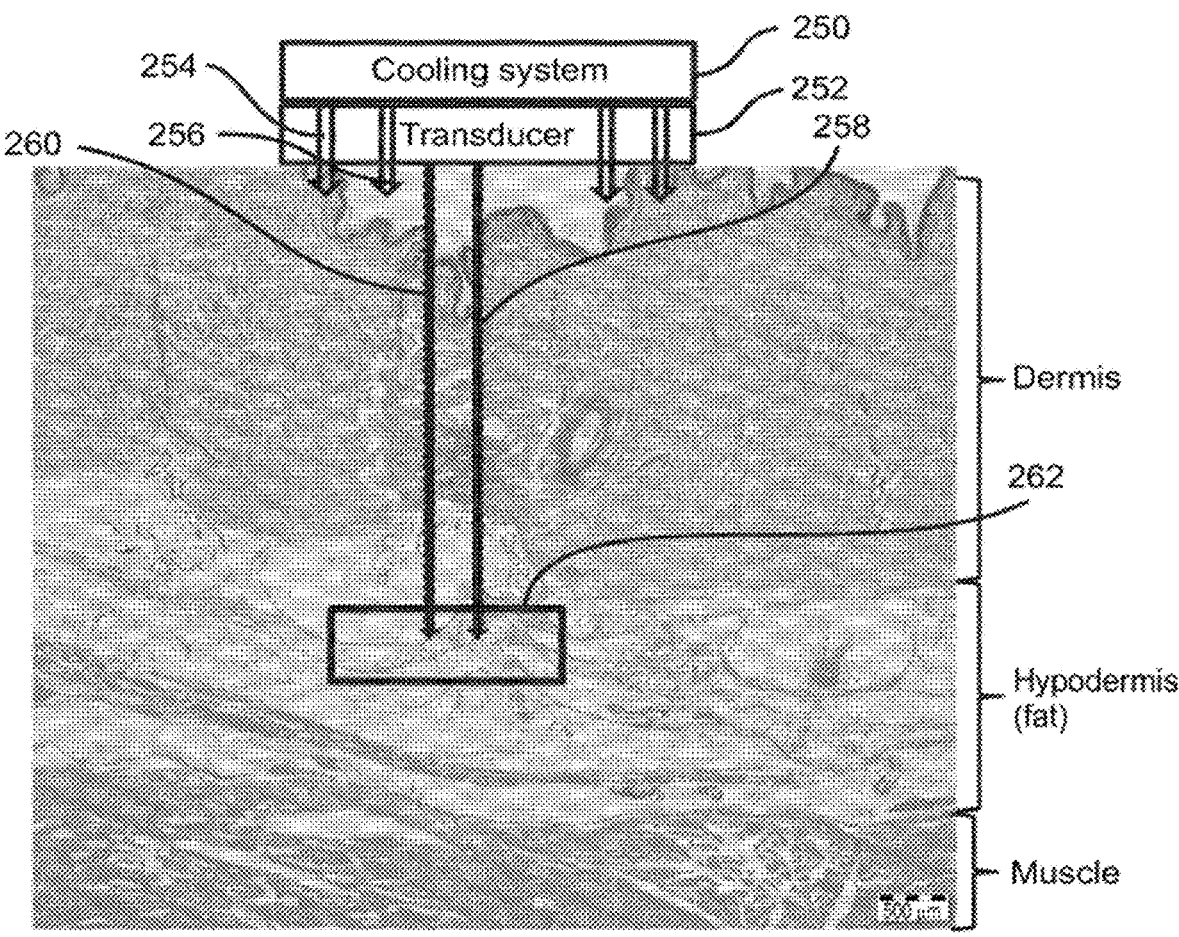
FIG. 2B is an image showing a distance and/or orientation between one or more transducers and a target tissue volume, according to some exemplary embodiments of the invention.

Reference is now made to FIG. 2B depicting a spatial relationship, for example distance and orientation between one or more ultrasound transducers and a tissue volume comprising fat tissue, according to some exemplary embodiments of the invention.

According to some exemplary embodiments, one or more transducers 252 are positioned at a close contact with a skin layer of a tissue. In some embodiments, the transducers 252 generate ultrasonic waves 258 and 260 towards a selected tissue volume, for example tissue volume 262. In some embodiments, the ultrasonic waves 260 and 258 penetrate to a depth of 0-30 mm, for example to a depth of 0-20 mm, 15-25 mm, 20-30 mm or any intermediate, smaller or larger depth, inside the tissue. In some embodiments, the ultrasonic waves penetrate through the dermis layer and into the selected tissue volume 262, which is positioned in the hypodermis layer comprising a fat tissue layer. In some embodiments, the ultrasonic waves are generated with intensity and/or frequency and/or duration sufficient to heat the fat tissue to a temperature in a range of 45-85° C., for example to a temperature range of 45-75° C., 52-57° C., 53-85° C. or any intermediate, smaller or larger range of temperatures. According to some exemplary embodiments, selected tissue volume 262 in the fat tissue layer is heated to the desired temperature while keeping skin layers, for example the epidermis layer of the skin and optionally the dermis layer cool enough, for example to minimize in at least 50% thermal damage caused by the thermal energy emitted from the transducers. In some embodiments, the skin layers are cooled down by a cooling system 250, which cools the skin contacting the transducers, either by cooling the transducers and/or by cooling the skin contacting the transducers through openings, for example channels passing through the transducers. In some embodiments, the channels comprise thermal conductive material configured to conduct cold from the cooling system directly to the skin.

According to some exemplary embodiments, the ultrasound transducers 252 are configured to deliver ultrasonic waves to different tissue layers, for example to the lamina propria tissue layer and/or to the fibromuscular tissue layer. In some embodiments, the ultrasound transducers 252 deliver ultrasonic waves to the lamina propria and/or to the fibromuscular in a timed relationship with the delivery of ultrasonic waves to the hypodermis, for example before, after and/or during the delivery of the ultrasonic waves to the hypodermis. In some embodiments, the ultrasonic waves are delivered to the lamina propria and/or to the fibromuscular tissue layers as part of additional treatment types, for example skin tightening treatments.

Exemplary Treating Different Regions of the Human Body

Figures 2C, 2D:
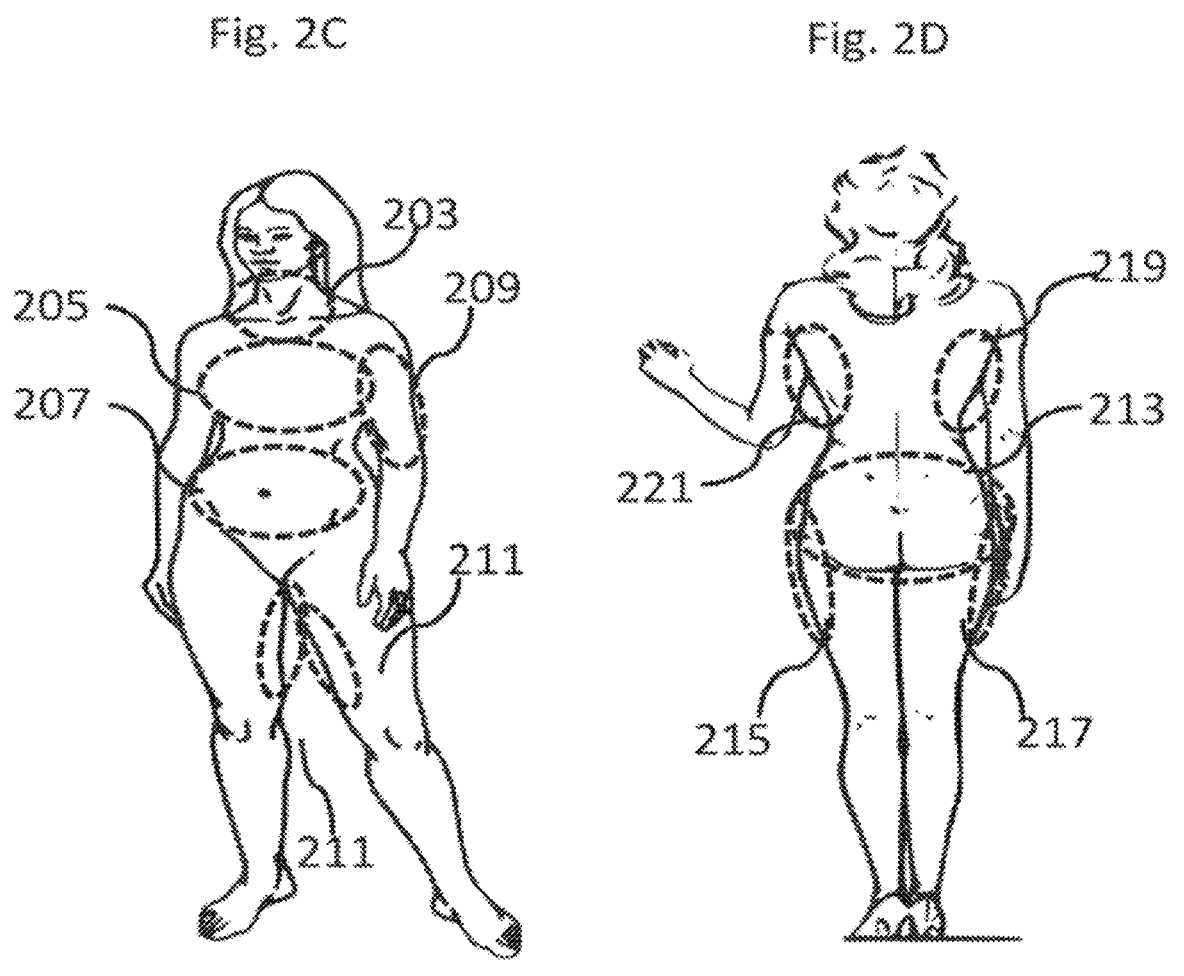

According to some exemplary embodiments, different regions of the human body, for example a male human body and a female human body, are treated using ultrasonic energy, for example unfocused ultrasonic energy. In some embodiments, the ultrasonic energy is delivered as part of body sculpting or body contouring treatments, which include for example fat reduction. In some embodiments, fat reduction is combined with other body contouring treatments. Reference is now made to FIGS. 2C and 2D depicting different treatment regions of the human body, according to some exemplary embodiments of the invention.

According to some exemplary embodiments, the ultrasonic energy is delivered to one or more body regions or portions thereof of men and women comprising, the chin and neck 203, the chest 205, the abdomen 207 including abdomen flanks, inner thighs 211, chest sides 219 and 221, outer thighs 215 and 217 and/or the buttocks 213.

Figure 2E:
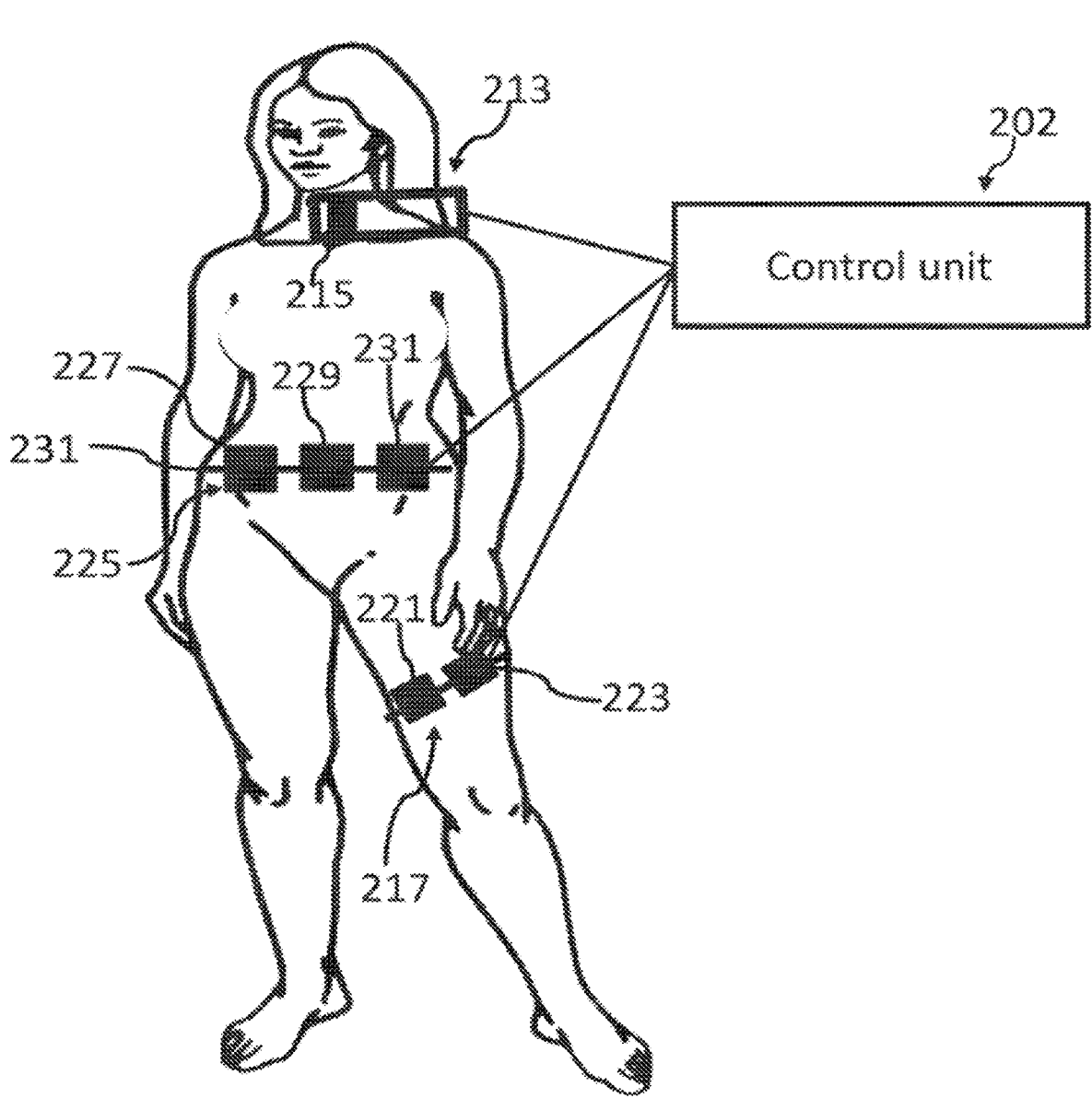
FIG. 2E is a schematic illustration of different ultrasound applicators at some of the treatment regions shown in FIGS. 2C and 2D, according to some exemplary embodiments of the invention.

According to some exemplary embodiments, for example as shown in FIG. 2E, different ultrasound applicators are selected when treating different regions of the body. In some embodiments, the different ultrasound applicators have different number of ultrasound transducers, different types of ultrasound transducers, for example ultrasound transducers having transmitting surface areas with varying size, and/or a different rearrangement of ultrasound transducers. Optionally, some of the ultrasound applicators comprise vacuum and/or vibration applicators, for example to apply the ultrasonic energy to the target region in a timed relationship with application of mechanical force on the tissue. In some embodiments, the ultrasound transducers vary in their cooling ability, for example when cold is delivered to the tissue before, during and/or after the application of ultrasonic energy to the tissue.

According to some exemplary embodiments, for example as shown in FIG. 2E, an ultrasound applicator, optionally a handheld ultrasound applicator for example applicator 213 is used when treated narrow body regions and/or small size body regions. In some embodiments, one or more ultrasound applicators, for example ultrasound applicator 215 are positioned in narrow width regions of the applicator 213, for example to allow positioning of the ultrasound transducer in narrow body regions, for example the neck or the chin. Optionally the handheld ultrasound applicator 213 is configured to stretch and/or to vibrate the tissue at the treatment region before, during and/or after application of ultrasonic energy. In some embodiments, the hand held ultrasound applicator 213 or portion thereof, for example a portion containing the one or more ultrasound transducers, is at least partly flexible, for example to conform to the body contour at the treatment region.

According to some exemplary embodiments, when treating larger regions of the human body, for example regions of the abdomen, a belt-shaped ultrasound applicator 225 comprises a plurality of ultrasound transducers, for example 3, 4, 5, 6 or any larger number of transducers, for example transducers 227, 229 and 231 is used. In some embodiments, the belt-shaped applicator comprises a strap 231, for example an elastic strap, configured to fasten the ultrasound transducers to the skin at the treated region. Optionally, the strap 231 interconnects at least some of the plurality of transducers. Optionally, the plurality of transducers are arranged linearly, for example side by side along the treatment region. Alternatively, the plurality of ultrasound transducers are arranged in any geometrical shape, for example to form a large flat surface to be placed in contact with the skin at the treatment region, According to some exemplary embodiments, at least some of the ultrasound transducers of the belt-shaped applicator 225 are movable relative to each other, for example to conform to the contour of the treatment region, for example the abdomen. In some embodiments, at least some of the ultrasound transducers are interconnected by one or more joints or elastic bands, for example to allow the relative movement of at least some of the transducers.

According to some exemplary embodiments, when applying ultrasonic energy to regions of a limb, for example inner or outer parts of a thigh, a belt-shaped applicator 217 is used, for example similar to applicator 225, which includes a small number of ultrasound applicators 221 and 223. In some embodiments, the number of ultrasound applicators and/or their arrangement is adjusted according to the surface area that needs to be treated. In some embodiments, as in applicator 225, the ultrasound transducers, for example transducers 221 and 223 are movable relative to each other, for example to allow the applicator to conform to the shape, for example contour, of the limb. In some embodiments, the ultrasound applicator comprises one or more ultrasound applicators within a sleeve, for example a stretchable sleeve. In some embodiments, the sleeve is shaped and sized to allow insertion of a limb of a subject through an opening in the sleeve.

According to some exemplary embodiments, the ultrasound applicators, for example ultrasound applicators 213, 225 or 217 is electrically connected to a control unit, for example the control unit 202 shown in FIG. 2A. In some embodiments, the control unit 202 is used to adjust one or more parameters of the treatment, for example intensity of the ultrasonic energy, frequency of the ultrasonic energy, application duration of the ultrasonic energy, skin cooling temperature and/or duration or any other treatment parameter, according to the applicator type and/or treated body region.

Exemplary Treatment Process

Figure 2F:
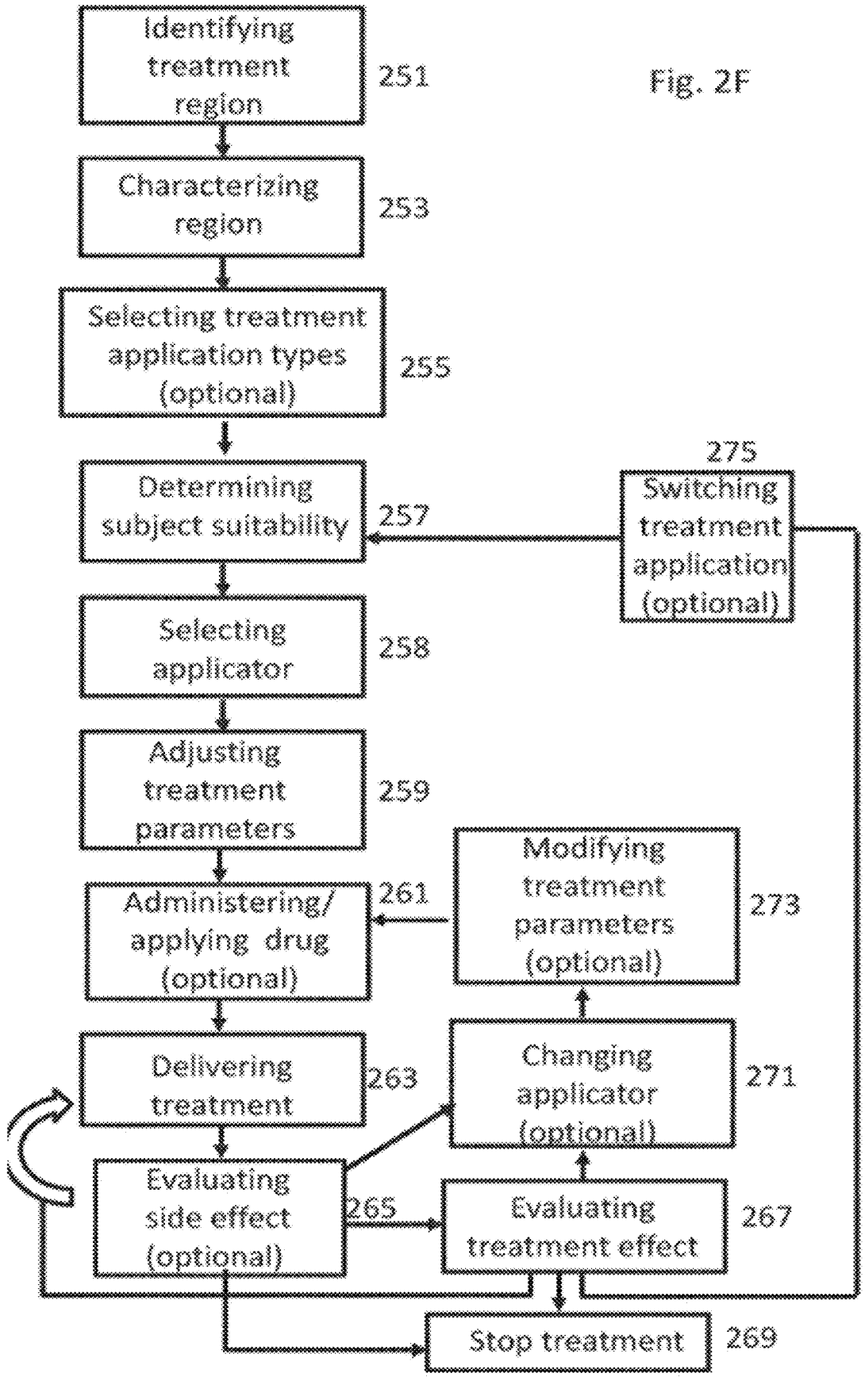
FIG. 2F is a flow chart of one or more treatment procedures, according to some exemplary embodiments.

According to some exemplary embodiments, ultrasonic energy, for example unfocused ultrasonic energy is delivered to one or more regions of the human body or animal body as part of a treatment, for example a cosmetic fat tissue treatment. In some embodiments, the ultrasonic energy is delivered with parameter values adjusted to reduce fat in a selected, for example targeted volume in the tissue. In some embodiments, the fat reduction treatment is combined with additional treatments, for example skin tightening. In some embodiments, the fat reduction treatment and/or any other treatments using the ultrasonic energy are part of body sculpting or body contouring treatments. Reference is now made to FIG. 2F, depicting a process of delivery of one or more treatment types, according to some exemplary embodiments of the invention.

According to some exemplary embodiments, for example during a diagnosing meeting, a treatment region is identified at block 251. In some embodiments, the identified treatment region comprises one or more of chin, neck, chest, abdomen, abdomen flanks, inner thighs, outer thighs, chest sides and/or the buttocks.

According to some exemplary embodiments, the identified treatment region is characterized at block 253. In some embodiments, the identified treatment region is characterized, for example by identifying one or more of cell types, tissue layer types, order of the tissue layers, thickness of one or more of the tissue layers, size and/or shape of one or more of the tissue layers in the treatment target.

According to some exemplary embodiments, optionally, treatment type applications are selected at block 255. In some embodiments, one or more treatment application types are selected at block 255. In some embodiments, the one or more treatment type applications are selected according to the treatment region identified for example at block 251, and/or based on the characteristics of the treatment region. In some embodiments, the treatment types comprise in addition to fat reduction treatments used for example to change the shape and size of fat cells, skin tightening treatments, and/or cellulite reduction treatments for example by shrinking and/or remodeling connective tissue.

According to some exemplary embodiments, subject suitability to the selected one or more treatment applications is determined at block 257. In some embodiments, the subject suitability to the selected one or more treatment applications is determined based on one or more of, subject current clinical condition, subject medical history, subject drug regime, subject thermal sensitivity for example the sensitivity of the subject to high levels of heat and/or cold, and/or subject age.

According to some exemplary embodiments, an ultrasound applicator is selected at block 258. In some embodiments, an ultrasound applicator is selected according to the selected one or more treatment applications type and/or according to the identified target region. In some embodiments, if the identified target region comprises the chin or the neck, for example as shown in FIG. 2C, then the selected application in a hand held ultrasound applicator that is, for example, at least partly flexible. Optionally, the applicator for treating the chin and/or the neck regions comprises one or more ultrasound transducers located on a narrow width portion of the applicator body, for example applicator 213 shown in FIG. 2E. In some embodiments, the hand held applicator 213 is used to treat body regions that have a surface area size of up to 400 cm$^2$, for example up to 200 cm$^2$, up to 300 cm$^2$, up to 400 cm$^2$, or any intermediate, smaller or larger surface area size.

According to some exemplary embodiments, if the selected treatment region comprises one or more treatment regions that have a large surface area, for example the abdomen, the chest and/or the buttocks, the selected ultrasound applicator comprises an array of ultrasound transducers coupled to each other and arranged to deliver ultrasonic energy to a large surface area, for example surface areas up to 1500 cm$^2$, for example up to 800 cm$^2$, up to 1000 cm$^2$, up to 1200 cm$^2$ or any intermediate, smaller or larger surface area size.

According to some exemplary embodiments, treatment parameter values are adjusted at block 259. In some embodiments, the treatment parameters are adjusted according to properties of the tissue layers at the identified treatment target, for example thickness, size, shape, depth of fat cells or fat layer from the epithelium or from the external layer of the skin, the shape, size and/or width of the fat layer. In some embodiments, the treatment parameters are adjusted according to the presence of nerve, blood vessels and/or other organs, for example organs that should not receive the ultrasonic energy, in the target region or near the target region, for example up to 5 cm, up to 4 cm, up to 2 cm or any intermediate, smaller or larger value from the target region.

According to some exemplary embodiments, treatment parameter values are adjusted according to characteristics of the subject, for example the subject ability to sustain continuous high heat levels or high cold levels during a predetermined time period, for example a time period in a range of 2-180 seconds, for example 2-50 seconds, 40-100 seconds, 50-120 seconds, 70-180 seconds, or any intermediate, smaller or larger range of values. In some embodiments, the treatment parameters comprise, ultrasonic waves frequency, ultrasonic waves intensity, duration of ultrasonic waves delivery, angle of delivery, cold level delivered to the skin and/or the duration of cold delivery. In some embodiments, the treatment parameters are adjusted according to the selected applicator and/or the characteristics of the treatment region.

According to some exemplary embodiments, when hating a fat cells layer, two or more ultrasound transducers of an applicator are directed to the same target region and are activated intermittently, for example to reduce epithelium heating by a single ultrasound transducer at a specific location, while continuously heating the fat cells layer by a different ultrasound transducer. In some embodiments, cold is continuously delivered to the epithelium by the two or more ultrasound transducers that deliver ultrasonic energy intermittently. Alternatively, cold is delivered intermittently by the two or more transducers. In some embodiments, the adjuster treatment parameters comprises the activation duration and/or sequence of activation of the two or more intermittently activated ultrasound transducers.

According to some exemplary embodiments, optionally, a drug is administered, for example systemically, or applied, for example, topically applied at block 261. In some embodiments, the drug is used to reduce thermal sensitivity of a subject or a specific skin region to high levels of heat and/or cold. In some embodiments, the drug is a topical anesthetic drug. In some embodiments, the drug comprises Lidocaine, prilocaine or any combination thereof.

According to some exemplary embodiments, a treatment, for example a cosmetic treatment to treat fat is delivered at block 263. In some embodiments, the treatment is delivered using the treatment parameter values adjusted at block 259. In some embodiments, the treatment is delivered to the to the identified treatment region.

According to some exemplary embodiments, optionally, treatment side effects are evaluated at block 265. In some embodiments, the treatment side effects are evaluated during the delivery of the ultrasonic energy to the fat tissue layer. Alternatively or additionally, the treatment side effects are evaluated after the delivery of the ultrasonic energy is stopped, for example up to 30 seconds, up to 1 minute, up to 10 minutes, up to 1 hour, up to 1 day or any intermediate, shorter or longer time period following the stopping of ultrasonic energy delivery. In some embodiments, the treatment side effects comprise the formation of edema at or near a contact site of the ultrasound transducers with the skin. Additionally or alternatively, the treatment side effects comprise formation of skin erythema or skin redness at or near a contact site of the ultrasound transducers with the skin. In some embodiments, the side effects comprise complaints of the treated subject on pain sensation.

According to some exemplary embodiments, the side effects are evaluated while the subject is in the clinic following a treatment session in which ultrasonic energy is delivered to the tissue. As used herein, a clinic refers to any location other than the house of the subject in which treatment and/or evaluation is provided. In some embodiments, the side effects are evaluated between two or more consecutive treatment sessions, scheduled for the save visit. Alternatively, the side effects are evaluated between visits, for example when the subject is at home. Optionally, the side effects are evaluated at home by the subject himself, for example, using an optic sensor of a mobile device, for example a cellular device. In some embodiments, the side effects are evaluated in a new visit at the clinic, for example in the beginning of a new treatment session.

According to some exemplary embodiments, a treatment effect is evaluated at block 267. In some embodiments, evaluation of the treatment effect comprises evaluation of the skin, for example evaluation of the shape and color of the skin. In some embodiments, evaluation of the treatment effect comprises evaluating shape and/or appearance of the treatment target, for example circumference of the treatment target.

According to some exemplary embodiments, the treatment effect is evaluated while the subject is in a visit following a treatment session or between two or more consecutive treatment sessions scheduled for the same visit in the clinic. In some embodiments, the treatment effect is evaluated at least 5 minutes, for example at least 10 minutes, at least 15 minutes, at least 30 minutes or any intermediate, shorter or longer time period following a treatment session, while the subject is still in the clinic. Alternatively or additionally, the treatment effect is evaluated at least 30 minutes, at least 1 hour, at least 24 hours, at least 48 hours or any intermediate, shorter or longer time period following a treatment session while the subject is at home. Optionally, the subject evaluated the treatment effect at home using an optic sensor of a mobile device, for example a cellular device.

According to some exemplary embodiments, if the treatment effect is not a desired effect, then the treatment is delivered again, in one or more treatment sessions at block 263. In some embodiments, the treatment is delivered again in one or more visits to the clinic. In some embodiments, if the treatment effect is not a desired effect then, the treatment is stopped at block 269. In some embodiments, if side effects appear, for example in an extent that is not allowed by the treatment protocol and/or regulatory approval, the treatment is stopped at block 269.

According to some exemplary embodiments, if the treatment effect is not a desired effect, then the ultrasound applicator is optionally changed at block 271. In some embodiments, the ultrasound applicator is changed, for example to better fit a selected treatment application and/or an identified treatment region. In some embodiments, the ultrasound applicator is changed to an ultrasound applicator which includes a different number of ultrasound transducers and/or a different arrangement of ultrasound transducers. In some embodiments, if side effects appear, for example in an extent that is not allowed by the treatment protocol and/or regulatory approval, the ultrasound applicator is changed at block 271.

According to some exemplary embodiments, if the treatment effect is not a desired effect, then the treatment parameters are modified at block 273. In some embodiments, the treatment parameters are modified at block 273 if side effects appear, for example in an extent that is not allowed by the treatment protocol and/or regulatory approval. In some embodiments, the treatment parameters are modified, for example ultrasound waves frequency, intensity, delivery time, cooling temperature and/or cooling direction.

According to some exemplary embodiments, if the treatment effect is a desired effect, then a treatment application is switched to a different application at block 275. In some embodiments, if the fat tissue reduction treatment reaches a desired effect, then the treatment application is switched to a skin tightening treatment application and/or other skin treatments.

Figure 2G:
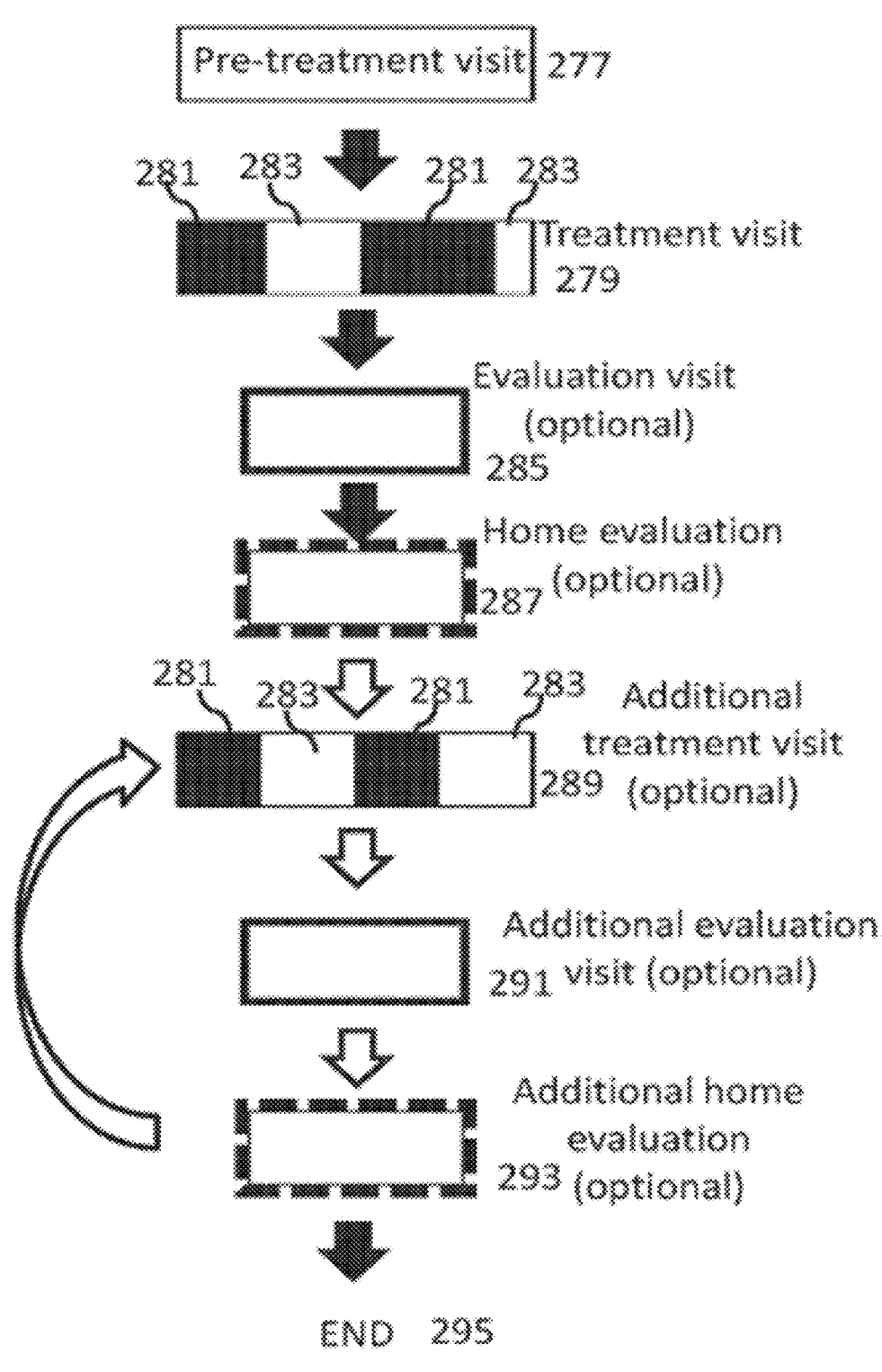
FIG. 2G is an overall treatment scheme, according to some exemplary embodiments of the invention.

Reference is now made to FIG. 2G, depicting a treatment scheme, according to some exemplary embodiments of the invention.

According to some exemplary embodiments, a subject arrives to a treatment center, for example a clinic to a pre-treatment visit at block 277. In some embodiments, the pre-treatment visit comprises performing one or more of identification of a treatment region, characterization of the treatment region, selection of treatment application types, and subject suitability determination, for example as described in steps 251-257 shown in FIG. 2F. In some embodiments, during the pre-treatment visit, a treatment plan is prepared. In some embodiments, the treatment plan comprises one or more of number of visits, number of treatment sessions per visit, time duration between visits, number of evaluation visits, type of evaluation, for example evaluation in the clinic or evaluation at home, amount of overall energy to be delivered to the tissue, amount of energy to be delivered to the tissue is a single visit and/or in a single treatment session.

According to some exemplary embodiments, the subject arrives at the clinic for a treatment visit 279, for example to receive ultrasonic energy treatment. In some embodiments, each treatment visit to the clinic lasts a time duration of up to 3 hours, for example up to 2 hours, up to 1 hour, up to 0.5 hour, up to 0.25 hour or any intermediate, smaller or larger time duration. In some embodiments, each treatment visit, for example treatment visit 279, comprises one or more treatment sessions, for example treatment sessions 281 in which ultrasonic energy is actively delivered to the tissue, for example as described in block 263 shown in FIG. 2F. Additionally, each treatment visit, for example treatment visit 279 comprises at least one evaluation session, for example evaluation sessions 283. In some embodiments, the at least one evaluation session comprises evaluation of side effects, for example as described in block 265 shown in FIG. 2F, and/or evaluation of a treatment effect, for example as described in block 267 shown in FIG. 2F. In some embodiments, at an end of a treatment visit, the subject is released from the clinic to his home.

According to some exemplary embodiments, optionally, the subject arrives at the clinic to a follow up visit, for example an evaluation visit, at block 285. In some embodiments, the evaluation visit is scheduled at least 1 day, for example 1 day, 3 days, 1 week, 2 weeks, 1 month, 3 months or any intermediate, shorter or longer time period following a treatment visit, for example treatment visit 279. In some embodiments, the evaluation visit comprises evaluation of side effects, for example as described at block 265 shown in FIG. 2F, and/or evaluation of a treatment effect, for example as described at block 267 shown in FIG. 2F.

According to some exemplary embodiments, optionally, the subject undergoes home evaluation at block 287. In some embodiments, the subject undergoes home evaluation using one or more sensors, for example an optic sensor of a mobile device, for example a cellular device. Optionally, the home evaluation is performed using a designated application installed in a memory of the mobile device. In some embodiments, the home evaluation comprises evaluation of side effects, for example as described at block 265 shown in FIG. 2F, and/or evaluation of a treatment effect, for example as described at block 267 shown in FIG. 2F. In some embodiments, the home evaluation is scheduled at least 1 day, for example 1 day, 3 days, 1 week, 2 weeks, 1 month, 3 months or any intermediate, shorter or longer time period following a treatment visit, for example treatment visit 279. Optionally, the subject receives an alert signal from the mobile device to perform the home evaluation.

According to some exemplary embodiments, based on the results of the evaluation visit at block 285 and/or the home evaluation at block 287, additional treatment visits are scheduled at block 289 and/or additional evaluation visits or home evaluations are scheduled at blocks 291 and 293 respectively.

Exemplary Detailed Fat Tissue Treatment Process

Figure 3A:
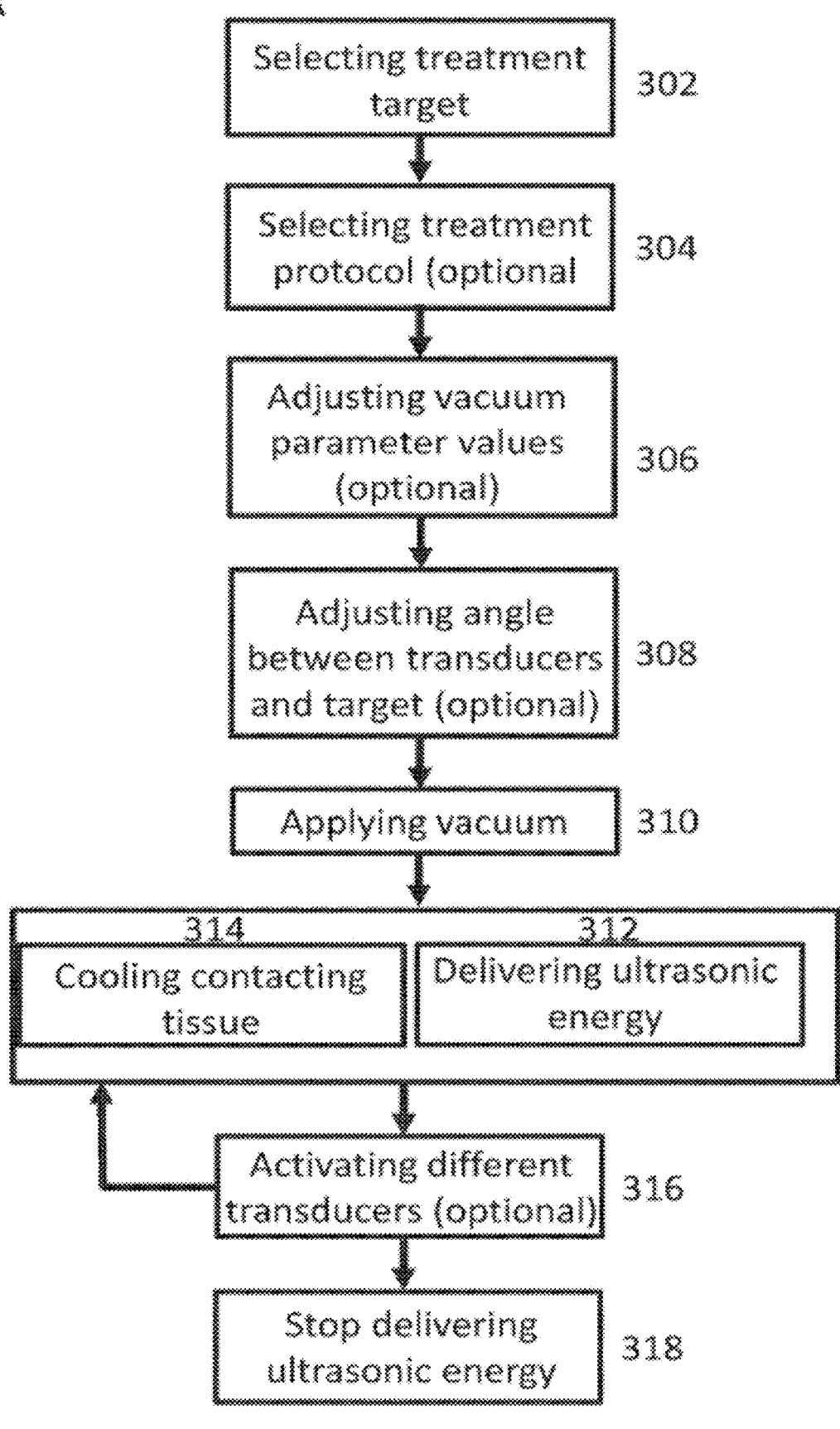
FIG. 3A is a flow chart of a detailed process for treating tissue by ultrasonic energy, according to some exemplary embodiments of the invention.

Reference is now made to FIG. 3A depicting a detailed process for treating fat tissue, according to some exemplary embodiments of the invention.

According to some exemplary embodiments, a treatment target is selected at 302. In some embodiments, the treatment target comprises a tissue region which is accessible to an ultrasound applicator. In some embodiments, the treatment target is selected based on a distance between the skin and selected tissue volume located within the tissue at the treatment target.

According to some exemplary embodiments, a treatment protocol is selected at 304. In some embodiments, the treatment protocol is selected based on an anatomical location of the selected treatment target. Alternatively or additionally, the treatment protocol is selected based on the age and/or the gender of the subject. Optionally, the treatment protocol is selected based on the tissue composition in the selected treatment target and/or the selected tissue composition in the selected tissue volume. In some embodiments, the tissue composition comprises a ratio between fat cells and other tissue types, for example collagen and/or elastin fibers, blood vessels, fibroblasts and so, in the selected tissue volume.

According to some exemplary embodiments, vacuum parameter values are adjusted at 306. In some embodiments, the vacuum parameter values are adjusted based on an anatomical location of the selected treatment target. Alternatively or additionally, the vacuum parameter values are adjusted, based on the tissue composition in the selected treatment target and/or the selected tissue composition in the selected tissue volume. In some embodiments, the vacuum parameter values are adjusted based on the elasticity of the tissue, for example based on the ability of the tissue to bend and/or to stretch.

According to some exemplary embodiments, an angle between the transducers and a target tissue volume is adjusted at 308. In some embodiments, at least some of transducers are positioned on a movable surface that allows to align the transducers at a desired angle with a selected tissue volume, for example to generate a selective effect at the tissue volume and not at adjacent tissue regions.

According to some exemplary embodiments, vacuum is applied at 310. In some embodiments, vacuum is applied on the tissue, for example by activating the low-pressure source 237 shown in FIG. 2A. In some embodiments, vacuum application causes at least part of the tissue to bend through at least one opening of the ultrasound applicator. In some embodiments, bending of the tissue through the opening presses the tissue against one or more ultrasound transducers of the ultrasound applicator.

According to some exemplary embodiments, ultrasonic energy is delivered to the selected tissue volume at 312. In some embodiments, the ultrasonic energy is generated by one or more transducers, for example transducers 208 shown in FIG. 2A. According to some exemplary embodiments, tissue contacting the transducers is cooled at 314. In some embodiments, the contacting tissue is cooled during the generation of the ultrasonic energy. Alternatively or additionally, the contacting tissue is cooled as long the tissue remains in contact with the at least part of the external surface of the one or more transducers. In some embodiments, the contacting tissue is cooled by cooling elements passing through a transducer body, for example through channels in the transducer body.

According to some exemplary embodiments, different transducers are activated at 316. In some embodiments, a least some of the transducers are sequentially activated, for example transducer groups directed to the same tissue volume are activated sequentially. Alternatively, single transducers are activated sequentially. In some embodiments, the transducers are sequentially activated for example, to allow continuous heating of the selected tissue volume without causing thermal damage to the skin be heating a single skin area.

According to some exemplary embodiments, the delivery of ultrasonic energy is stopped at 318. In some embodiments, the delivery of ultrasonic energy is stopped when a treatment session is finished. Alternatively, the delivery of ultrasonic energy is stopped when a skin temperature at a contact point between the transducers and/or the applicator reaches a pre-determined temperature value, for example 42° C.

Exemplary Ultrasound Applicator

Figure 3B:
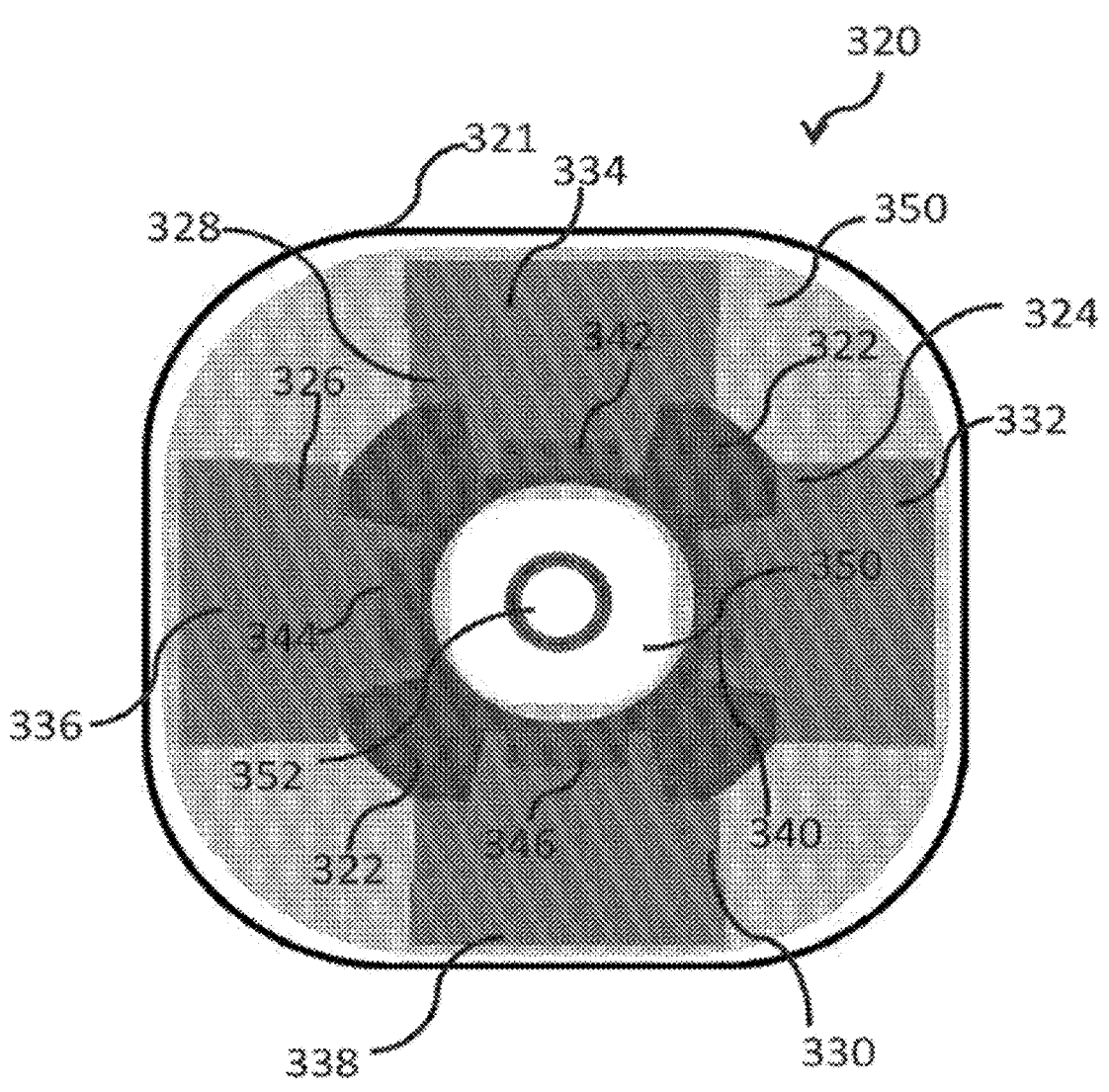
FIG. 3B is a schematic illustration showing from a bottom view an ultrasound applicator, according to some exemplary embodiments of the invention.

Reference is now made to FIG. 3B, depicting an ultrasound applicator from a bottom view, according to some exemplary embodiments of the invention.

According to some exemplary embodiments, ultrasound applicator, for example applicator 320 comprises at least one cooling chamber, for example cooling chamber 322. Optionally, the cooling chamber is a central cooling chamber and is used to cool a plurality of cooling elements, for example a plurality of TECs. In some embodiments, the cooling chamber is a ring shaped cooling chamber, shaped and sized to surround an inner lumen of the applicator 320. In some embodiments, the applicator 320 comprises housing 321 having at least one opening through a surface of said housing, for example opening 350, connecting the inner lumen with the external environment.

According to some exemplary embodiments, the applicator 320 comprises one or more cooling elements for example one or more TECs. In some embodiments, the applicator, for example applicator 320 comprises at least two TECs, for example 2 TECs, 4 TECs, 6 TECs or any intermediate, smaller or larger number of TECs. In some embodiments, for example as shown in FIG. 3B the applicator 320 comprises 4 TECs, for example TECs 324, 326, 328, and 330. In some embodiments, a hot surface of each TEC is attached to a surface of the cooling chamber 322, for example to allow heat dissipation from the TEC to the cooling liquid inside the cooling chamber 322.

According to some exemplary embodiments, a cold surface of each TEC is attached directly to an ultrasound transducer, for example to cool down the ultrasound transducer. Alternatively, the cold surface of the TEC is attached to transducer holder, for example a transducer base. In some embodiments, the transducer holder is a thermal conductive transducer holder, optionally made from Aluminum. In some embodiments, for example as shown in FIG. 3B, each of the TECs 324, 326, 328 and 330 is attached to a single transducer, for example transducers 340, 344, 342 and 346 respectively.

According to some exemplary embodiments, each of the transducers is aligned to face at least partly the inner lumen of the applicator and/or the opening 350. In some embodiments, each of the transducers is aligned to have an ultrasound emitting surface of the transducer facing at least partly the inner lumen of the applicator and/or the opening 350. In some embodiments, the transducers are aligned by an angled portion of each transducer base which is shaped and sized to align the transducers towards the inner lumen or the opening 350. In some embodiments, the transducers surround the inner lumen and/or the opening 350. In some embodiments, the transducers are evenly spaced-apart around the opening 350. Optionally, at least two transducers face each other, for example transducers 340 and 344, and transducers 342 and 346. In some embodiments, at least two transducers are positioned in opposite directions around the opening 350.

According to some exemplary embodiments, the applicator 320 comprises an opening of a low-pressure source, for example a vacuum opening 352 also termed herein in some embodiments as vacuum outlet. In some embodiments, activation of a low-pressure source, for example a vacuum pump, connected to the vacuum opening 352, lowers the pressure within the inner lumen of the applicator 320. Optionally, lowering the pressure causes a tissue contacting the applicator to penetrate at least partly into the inner lumen through the opening 350.

According to some exemplary embodiments, the applicator comprises at least one cover, for example cover 350. In some embodiments, cover 50 covers the transducers when they are placed in contact with tissue, for example to maintain sterility of the transducers and/or at least part of the applicator.

Figure 4A:
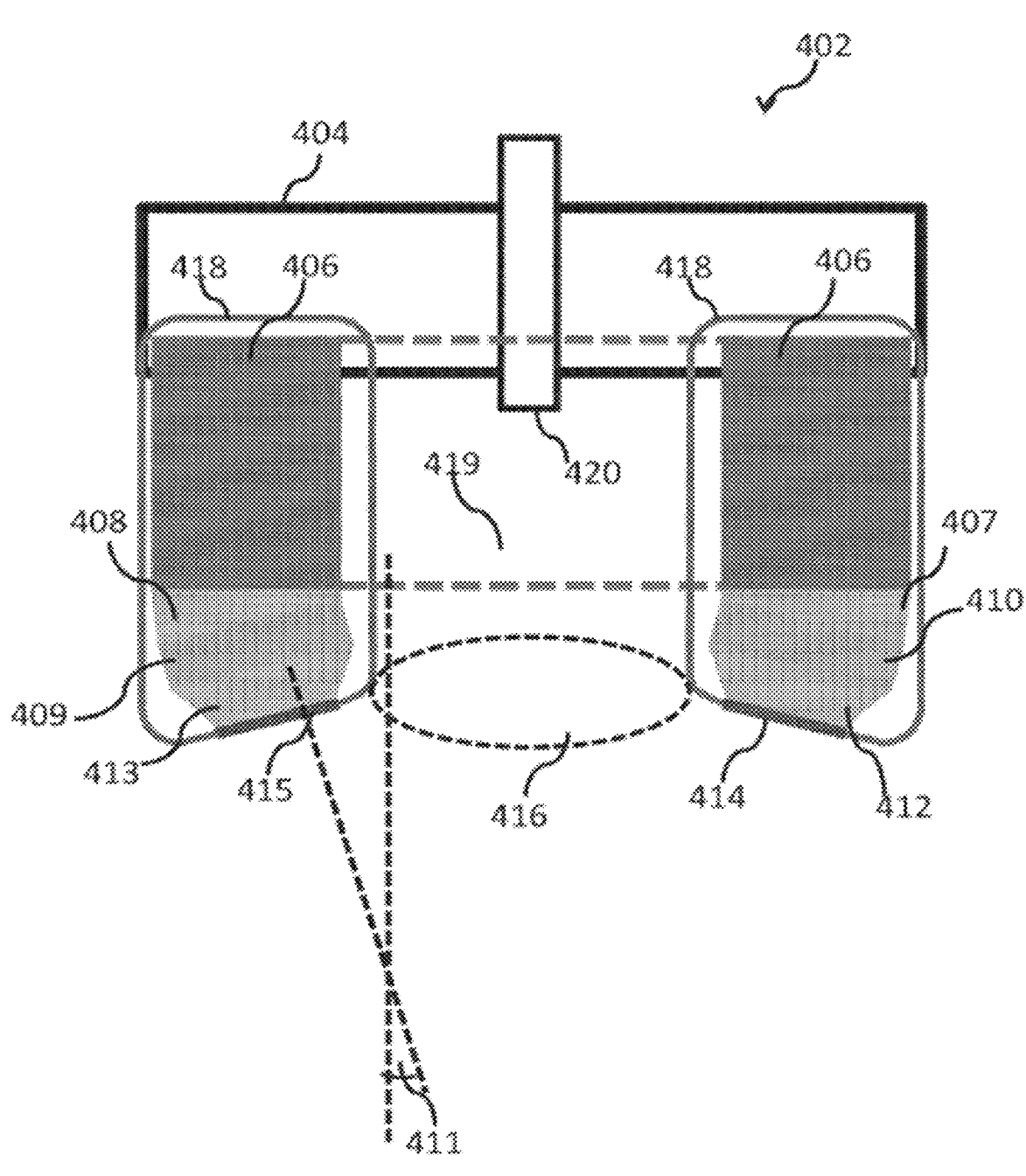
FIG. 4A is a schematic cross-section view of an applicator with an opening having a plurality of ultrasonic transducers and a low pressure source, according to some exemplary embodiments of the invention.

Reference is now made to FIG. 4A depicting a cross-section of an ultrasound applicator with at least two ultrasound transducers directed towards a single tissue volume, according to some exemplary embodiments of the invention.

According to some exemplary embodiments, an ultrasound applicator, for example applicator 402 comprises casing 404 and at least one opening in the casing 404, for example opening 416. In some embodiments, the applicator 402 comprises at least one cooling chamber, for example cooling chamber 406. In some embodiments, the cooling chamber 406 surrounds an internal lumen of the applicator 402, for example lumen 419. In some embodiments, the cooling chamber comprises cooling liquid, for example water, which circulates between the applicator 402 and a cooling system in a control unit, for example as described in FIG. 2A.

According to some exemplary embodiments, a lower surface of the cooling bath is attached to a surface of an adaptor, for example adaptor 408. In some embodiments, the adaptor 408 is a thermal conducting adaptor, optionally made from Aluminum. In some embodiments, the adaptor 408 is an angled adaptor, having a lower surface positioned in an angle relative to the upper surface contacting the cooling chamber. In some embodiments, the applicator comprises a plurality of adaptors attached to the lower surface of the cooling bath. Additionally, the plurality of adaptors surround the lumen 419 of the applicator 402.

According to some exemplary embodiments, at least one cooling element, for example TEC 409 is attached to a lower surface of adaptor 408. In some embodiments, each adaptor is attached to one or more TECs. Optionally, each adaptor is attached to a single TEC. In some embodiments, a lower surface of adaptor 408 is attached to a hot surface of TEC 409, and a lower surface of adaptor 407 is attached to a hot surface of adaptor 410.

According to some exemplary embodiments, each TEC is connected to at least one ultrasound transducer by a transducer holder. In some embodiments, a cold surface of the TEC is attached to an upper surface of the transducer holder or directly to the ultrasound transducer. In some embodiments, the cold surface of the TEC cools the transducer and/or a tissue contacting the transducer via the transducer holder or by directly contacting the transducer. In some embodiments, a cold surface of TEC 409 is connected to an ultrasound transducer 415 by a transducer holder 413. Additionally, a cold surface of TEC 410 is connected to an ultrasound transducer 414 by a transducer holder 412.

According to some exemplary embodiments, each of the transducers of a single applicator, for example transducers 414 and 415 face the opening 416 in the applicator's casing.

Optionally, each of the transducers of a single applicator at least partly faces at least some of the other transducers of the same applicator.

According to some exemplary embodiments, the applicator 402 comprises at least one vacuum outlet, for example outlet 420 in the applicator inner lumen, for example lumen 419. In some embodiments, the outlet 420 is connected to a low-pressure source, optionally positioned in a control unit connected to the applicator, for example as described in FIG. 2A.

Figure 4B:
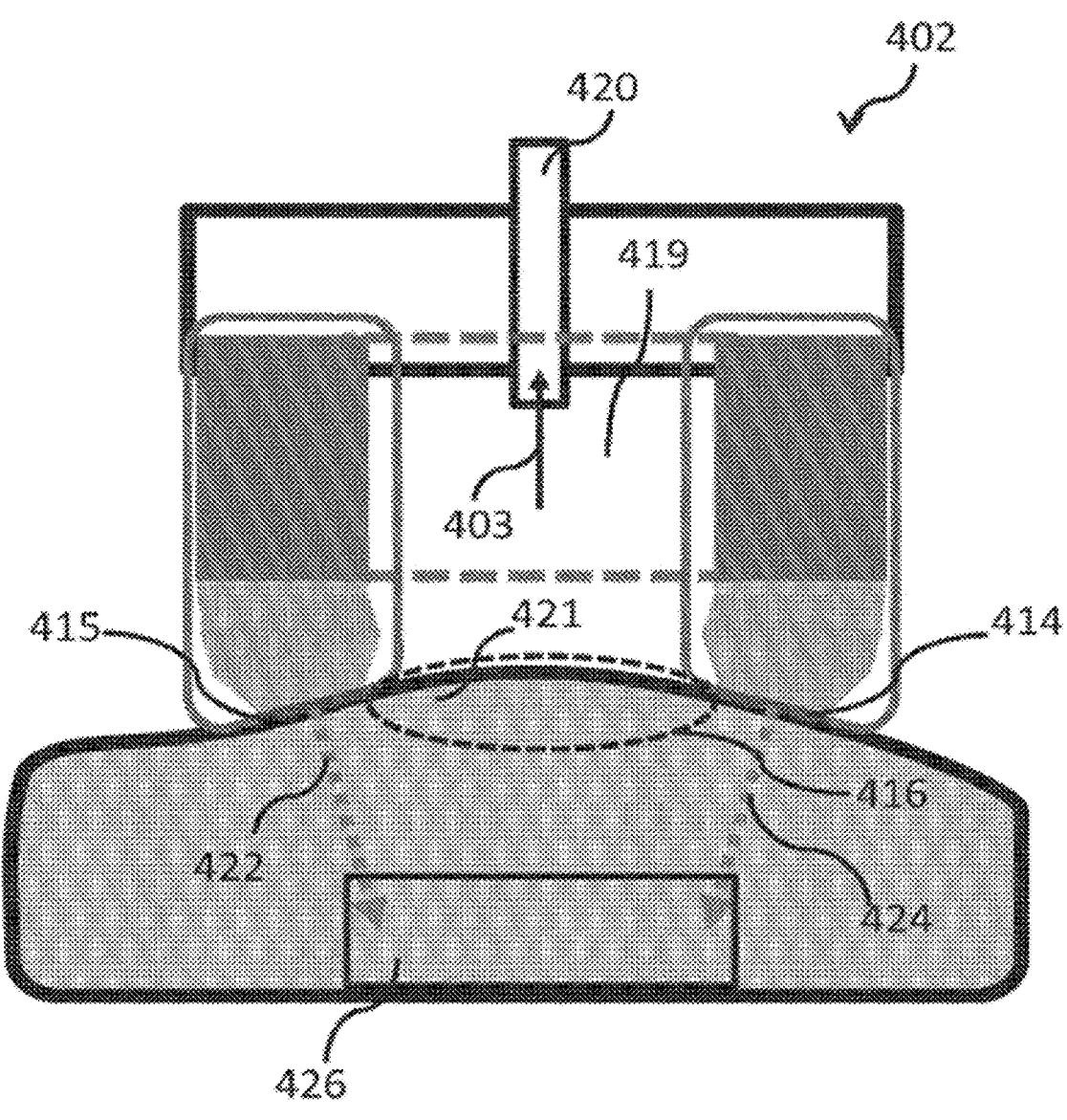
FIG. 4B is a schematic cross-section view of the applicator shown in FIG. 4A placed in contact with a target tissue, according to some exemplary embodiments of the invention.

Reference is now made to FIG. 4B which is a cross section view, depicting the applicator shown in FIG. 4A during the delivery of ultrasonic energy to a tissue volume, according to some exemplary embodiments of the invention.

According to some exemplary embodiments, vacuum is applied through the outlet 420 causing suction of air into the outlet in direction 403 and reduces the pressure within the inner lumen 419. In some embodiments, application of vacuum while pressing the applicator against a tissue surface causes penetration of tissue 421 through the opening 416 at least partly into the lumen 419. In some embodiments, at least partial penetration of the tissue 421 into the lumen 419 forces the tissue against the transducers 414 and 415, optionally ensuring tight contact between the transducers and the skin when delivering the ultrasonic energy.

According to some exemplary embodiments, while vacuum is applied, each transducer generates ultrasonic waves, for example unfocused ultrasonic waves, for example beams 422 and 424, from different angular directions into a single tissue volume 426. In some embodiments, the applicator is configured to deliver ultrasonic waves to a tissue volume in a range of 10-10000 mm^2, for example 10-800 mm^2, 20-1000 mm^2, 900-5000 mm^2, 4000-10,000 mm^2 or any intermediate, smaller or larger tissue volume. In some embodiments, each of the transducers of a single ultrasound applicator is positioned in an angle of 0-90°, relative to the tissue volume, for example in an angle of 10°, 20°, 30°, 45° or any intermediate, smaller or larger value. In some embodiments, treated tissue volumes are separated by regions of tissue with no damage. In some embodiments, the distance between treated tissue volumes is in the range of 0.5-20 mm, for example in a range of 1-15 mm, 1-5 mm, 4-20 mm or any intermediate, smaller or larger range of values.

Figure 5A:
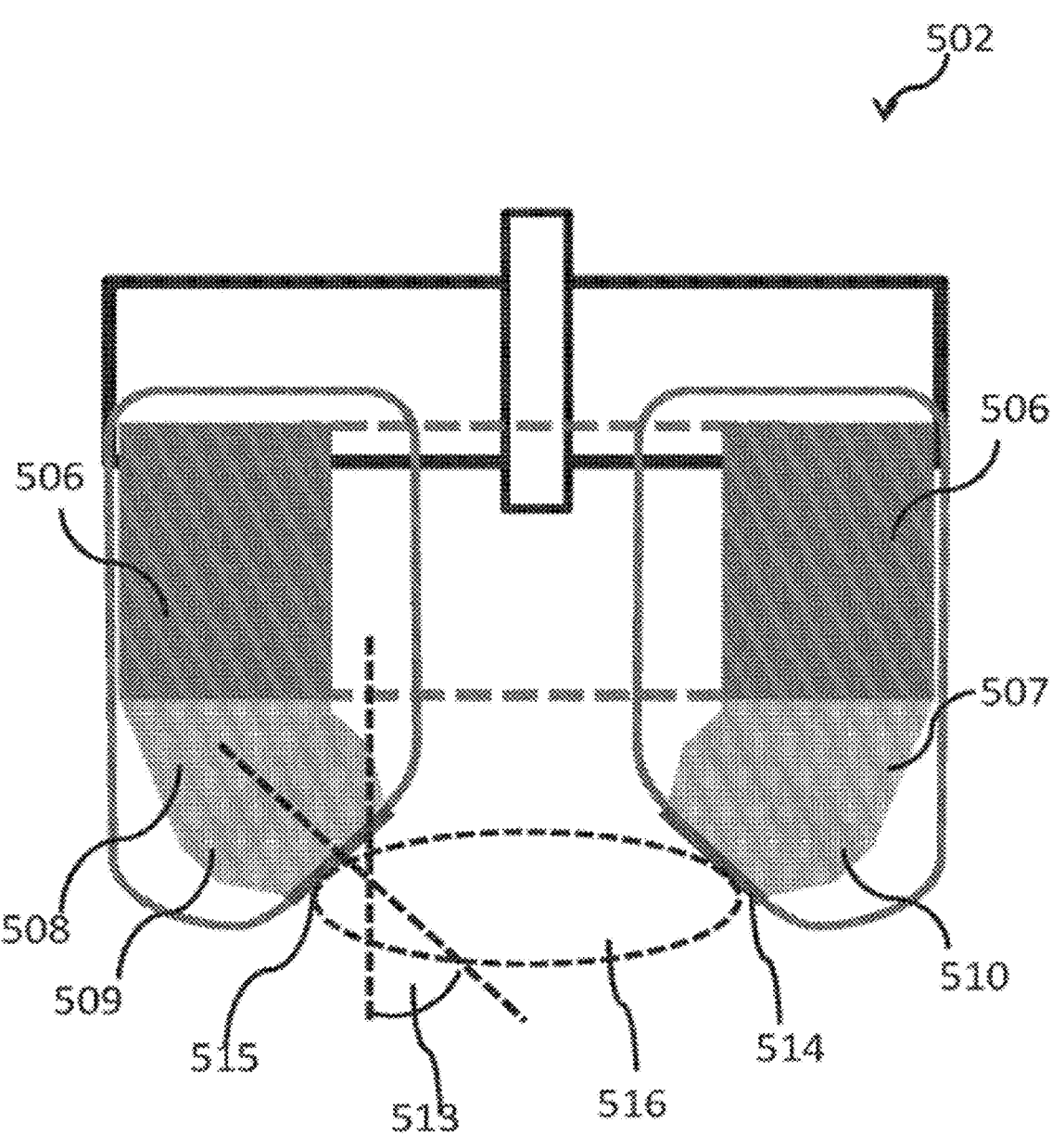
FIG. 5A is a schematic cross-section view of an applicator with an opening having a plurality of ultrasonic transducers facing the opening, according to some exemplary embodiments of the invention.
Figure 5B:
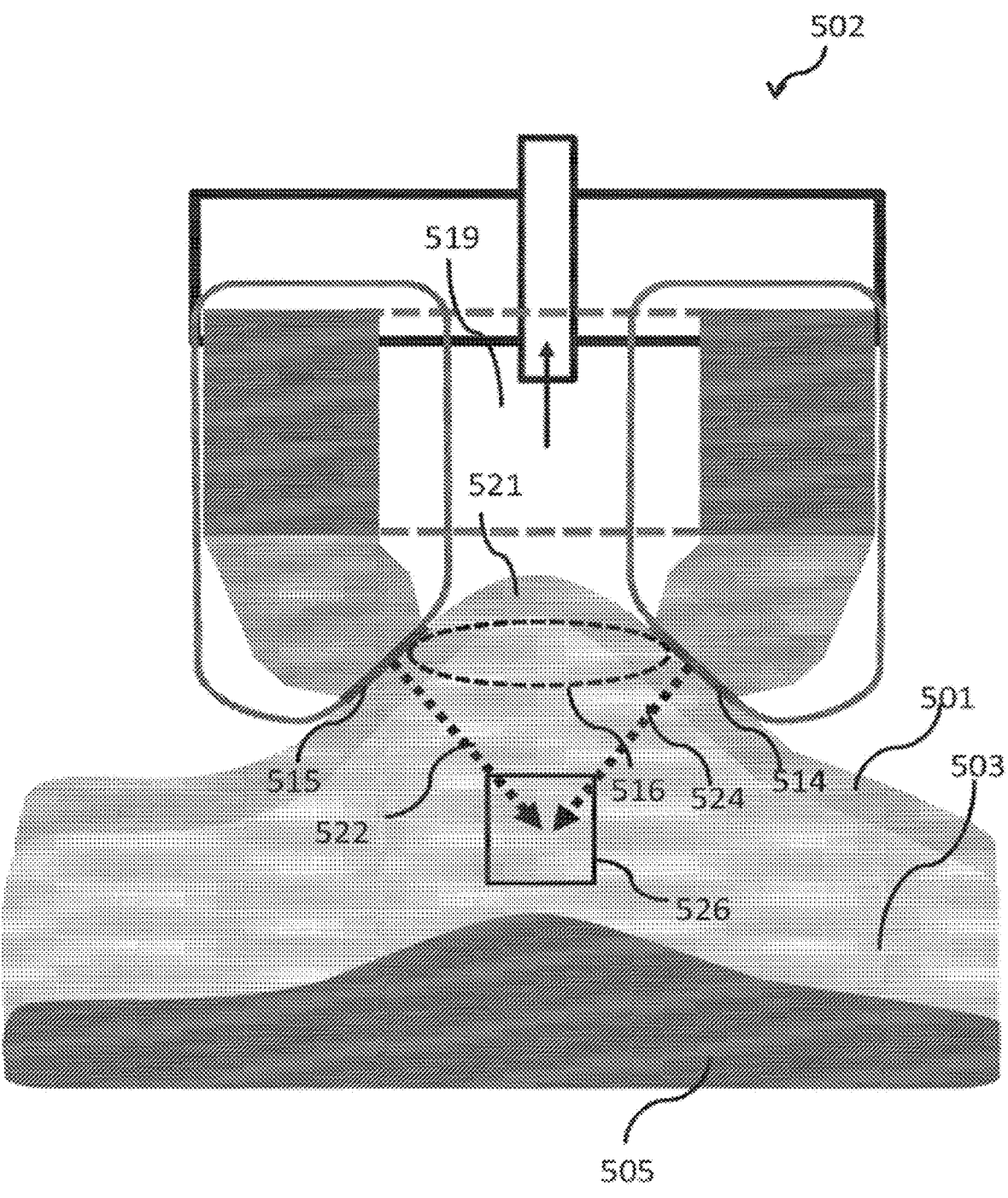
FIG. 5B is a schematic cross-section view of the applicator shown in FIG. 5A placed in contact with a target tissue, according to some exemplary embodiments of the invention.

Reference is now made to FIGS. 5A and 5B depicting a cross-section view of an applicator where the ultrasound transducers are directed to a smaller tissue volume, according to some exemplary embodiments of the invention.

According to some exemplary embodiments, replacing an adaptor between the cooling bath and the TEC allows, for example to change the relative angle between the transducers of an ultrasound applicator and a tissue volume. In some embodiments, for example as shown in FIG. 5A, adaptors 507 and 508 are attached to the cooling chamber 506. In some embodiments, a lower surface of each of the adaptors is positioned in a larger angle 513 relative to the cooling chamber and/or to the upper surface of the adaptor, compared to angle 411 in applicator 402.

According to some exemplary embodiments, for example as shown in FIG. 5B, when vacuum is applied in lumen 519 of the applicator 502, a tissue portion 521 penetrated through an opening 516 into an inner lumen 519 of the applicator. In some embodiments, ultrasonic waves generated by transducers 514 and 515, for example beams 524 and 522 respectively are directed to a smaller tissue volume 526. In some embodiments, the ultrasonic waves penetrate through a dermis layer 501 of the skin and into the tissue volume 526 in a hypodermis layer 503 containing fat tissue, for example as previously shown in FIG. 2B. In some embodiments, the ultrasonic waves are generated with frequency and/or intensity values that prevent at least partly the penetration of the ultrasonic waves into a muscle tissue layer 505 located underneath the hypodermis layer 503.

According to some exemplary embodiments, an angle between the transducers and the tissue volume is controlled using one or more angled adaptors between the cooling chamber and the transducers. Optionally, the adaptors are flexible and optionally allow to control the angle by controlling the applied vacuum level. In some embodiments, high vacuum levels cause the adaptors to bend inward, and to direct the ultrasonic waves to a smaller tissue volume.

Figure 6A:
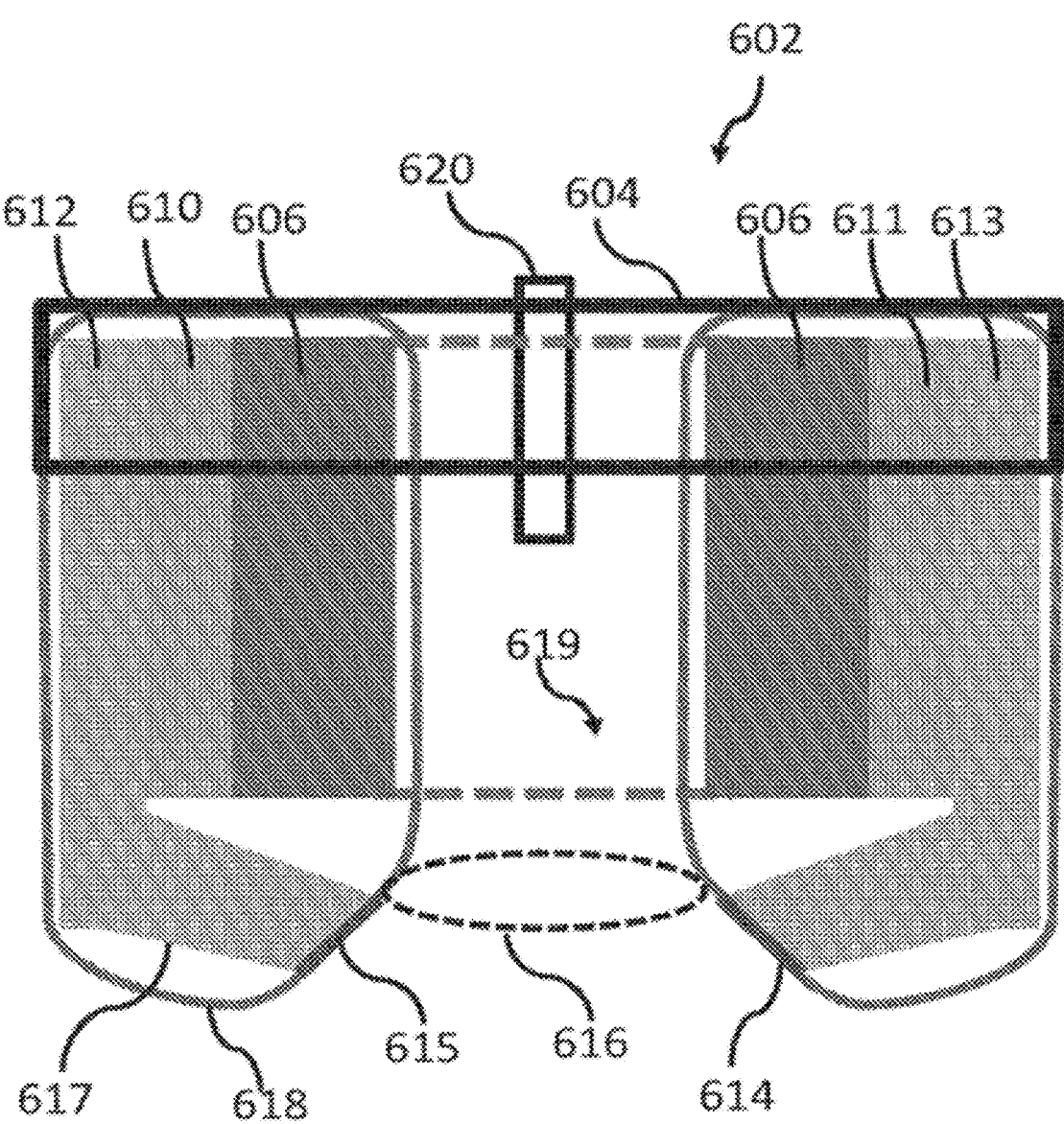
FIG. 6A is a schematic cross-section view of an applicator with an opening having a plurality of ultrasonic transducers facing the opening and a large contact area between TECs and thermal energy conducting elements, according to some exemplary embodiments of the invention.
Figure 6B:
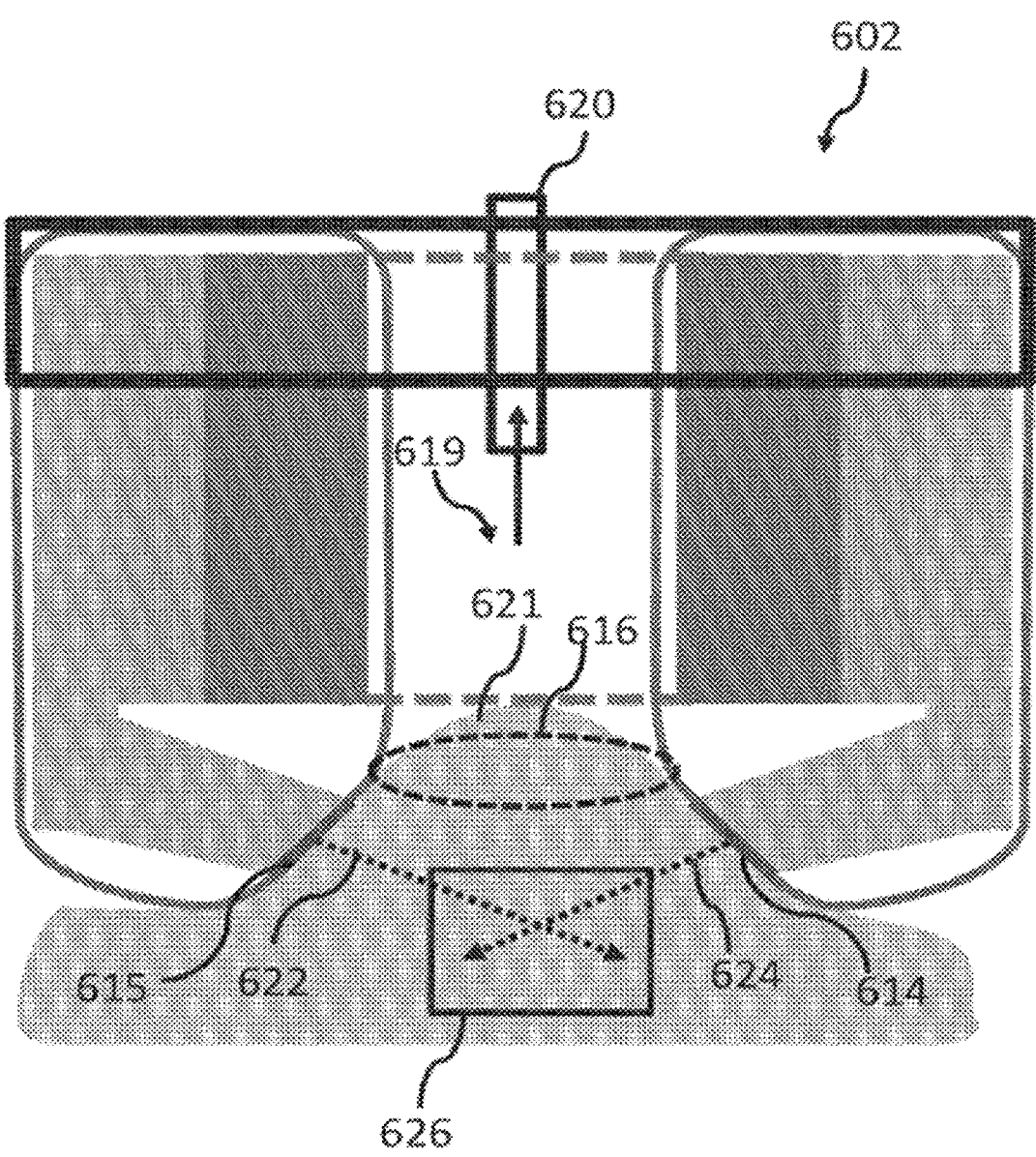
FIG. 6B is a schematic cross-section view of the applicator shown in FIG. 6A placed in contact with a target tissue, according to some exemplary embodiments of the invention.

Reference is now made to FIGS. 6A and 6B depicting a cross-section view of an ultrasound applicator having a large contact area between a TEC and a cooling chamber, according to some exemplary embodiments of the invention.

According to some exemplary embodiments, an ultrasound applicator, for example applicator 602 comprises a housing 604 having at least opening 616 shaped and sized to face a tissue. In some embodiments, the applicator 602 comprises at least one cooling chamber, for example cooling chamber 606. In some embodiments, the cooling chamber 606 comprises cooling liquid, for example water, as previously described in FIG. 5A. In some embodiments, the cooling chamber 606 surrounds an inner lumen 619.

According to some exemplary embodiments, a side surface of the cooling chamber 606 is attached to at two or more cooling elements, for example TECs 610 and 611. In some embodiments, a hot surface of each of the TECs is attached to the surface of the cooling chamber 606, for example to allow heat dissipation from the TEC into the cooling liquid inside the cooling chamber.

According to some exemplary embodiments, a cold surface of the TEC, for example TEC 610 is attached to a surface of at least one transducer holder, for example transducer holder 612. In some embodiments, the transducer holder 612 is a thermally conductive transducer holder, configured to conduct cold towards at least one ultrasound transducer, for example transducer 612 attached to the holder. In some embodiments, the transducer holder is made from a thermally conductive material, for example aluminum.

According to some exemplary embodiments, a distal section of each transducer holder, for example distal section 617 is angled towards the opening 616 and/or the inner lumen 619. In some embodiments, the transducer 615 is attached to a distal end of the transducer holder 617.

According to some exemplary embodiments, at least one vacuum outlet, for example outlet 620 is connected to the inner lumen 619. In some embodiments, activation of a low-pressure source connected to the outlet 620 allows lower the pressure levels within the inner lumen 619.

According to some exemplary embodiments, for example as shown in FIG. 6B, lowering the pressure levels in the inner lumen 619 while the applicator is attached to a tissue surface causes a partial penetration of a tissue portion 621 through the opening 616 into the inner lumen 619 of the applicator. In some embodiments, the partial penetration of the tissue portion 621 into the inner lumen 619 pushes the tissue against the transducers, for example transducers 614 and 615. In some embodiments, ultrasonic waves generated by the transducers 614 and 615 are directed towards the same tissue volume, for example tissue volume 626.

A potential advantage of having a large contact area, and optionally a direct contact between a hot surface of a TEC and a surface of a cooling chamber is that it improves heat dissipation and allows to activate ultrasound transducers with large contact area with the skin, for longer time periods.

Exemplary Ultrasound Applicators Array

Figure 6C:
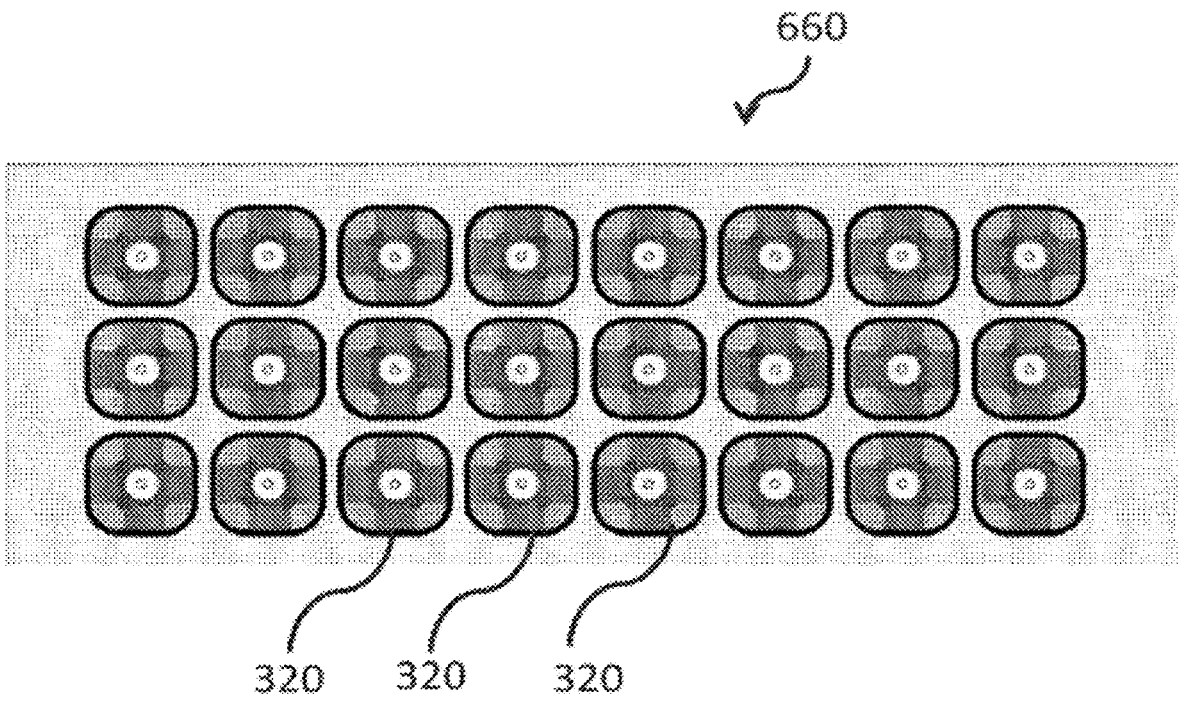
FIG. 6C is a schematic illustration showing an array of ultrasound transducers, according to some exemplary embodiments of the invention.

According to some exemplary embodiments, a two or more ultrasound applicators are combined into an array of ultrasound applicators. In some embodiments, an ultrasound applicator array is used, for example to treat large areas of tissue, which optionally include fat tissue. Reference is now made to FIG. 6C depicting an array of ultrasound applicators, according to some exemplary embodiments of the invention.

According to some exemplary embodiments, an array of ultrasound applicators, for example array 660 comprises two or more ultrasound applicators, for example applicator 320 previously shown in FIG. 3B. In some embodiments, the two or more transducers are attached to an elastic material, for example a strap or a belt. In some embodiments, the elastic material is shaped and sized to be wrapped around a body part, for example a limb. In some embodiments, the array is fastened to a tissue surface and/or a body part by one or more fasteners.

Exemplary Ultrasound Transducer with One or More Openings

Figure 7A:
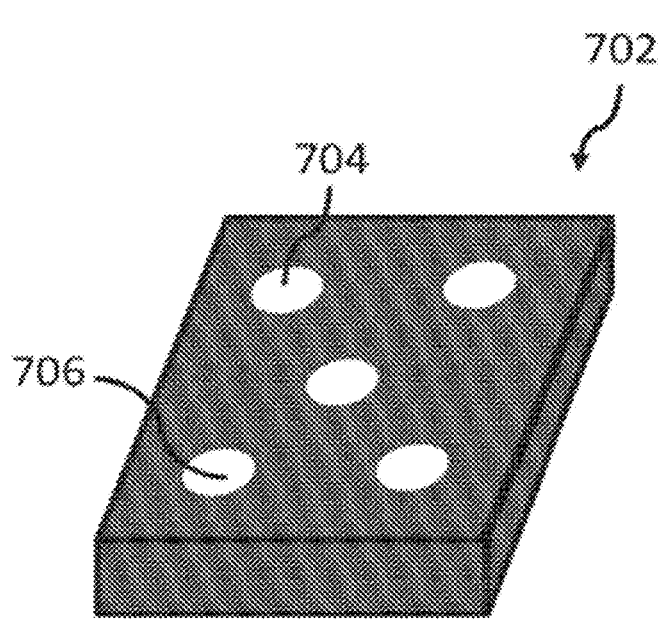
FIG. 7A is a schematic illustration of an ultrasound transducer having crossing through openings, according to some exemplary embodiments of the invention.

Reference is now made to FIG. 7A, depicting an ultrasound transducer with at least one channel, according to some exemplary embodiments of the invention.

According to some exemplary embodiments, an ultrasound transducer comprises a PZT plate, for example plate 702 with one or more channels, for example channel 704 and channel 706. In some embodiments, the channels cross-through the plate from a first surface to a second surface of the plate 702.

Reference is now made to FIGS. 7B-7E depicting different assemblies of an ultrasound transducer having at least one channel, according to some exemplary embodiments of the invention.

According to some exemplary embodiments, assembly 710 comprises a cooling basement 712, for example a transducer holder, attached to an upper surface PZT plate 702. In some embodiments, the assembly 710 comprises a flex PCB 716, attached to a lower surface of the PZT plate 702. In some embodiments, one or more temperature sensors, for example thermistor 714, are electrically connected to the flex PCB 716 and are positioned within the channels, for example within channel 704 of the PZT plate 702. Optionally, each thermistor is positioned in a different channel.

According to some exemplary embodiments, having a PZT plate with empty channels allows, for example to cool a tissue contacting the flex PCB, through the channels. In some embodiments, the thermistors in the channels allow, for example, to monitor the temperature level of the PZT plate during the delivery of ultrasonic energy, and or the temperature inside the channel, for example to determine the efficiency level of the cooling process. Additionally or alternatively, the thermistors monitor the temperature at the contact point between the PZT plate and the contacting tissue.

Figure 7B:
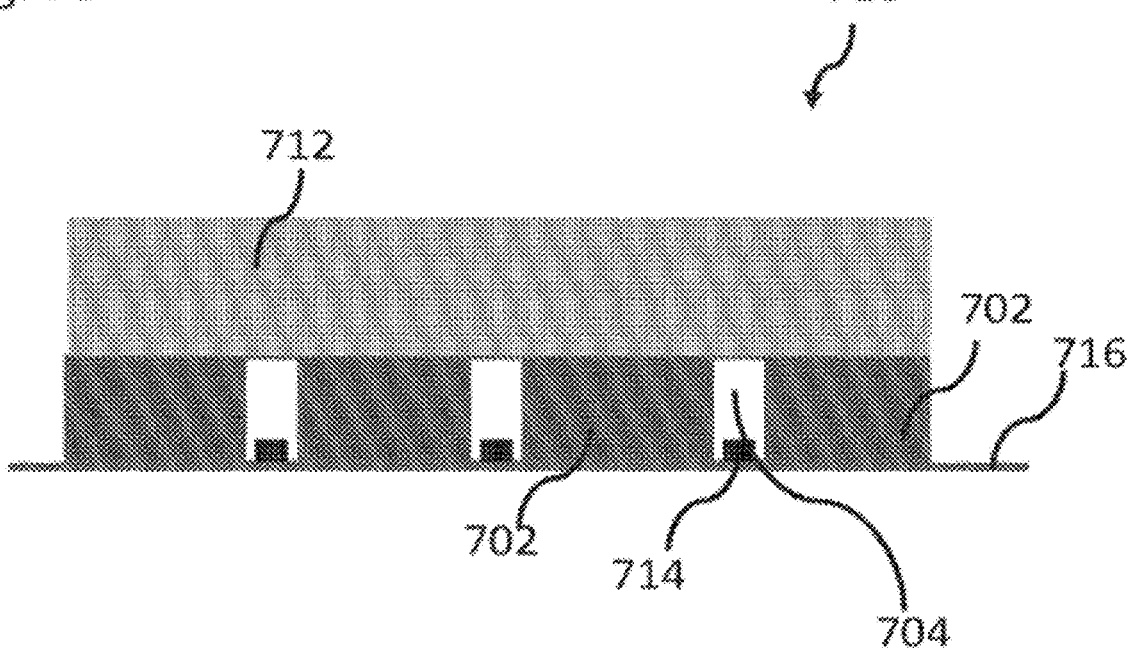
FIG. 7B is a schematic cross-section view of an assembly of a cooling element attached to a surface of the ultrasound transducer shown in FIG. 7A, according to some exemplary embodiments of the invention.
Figure 7C:
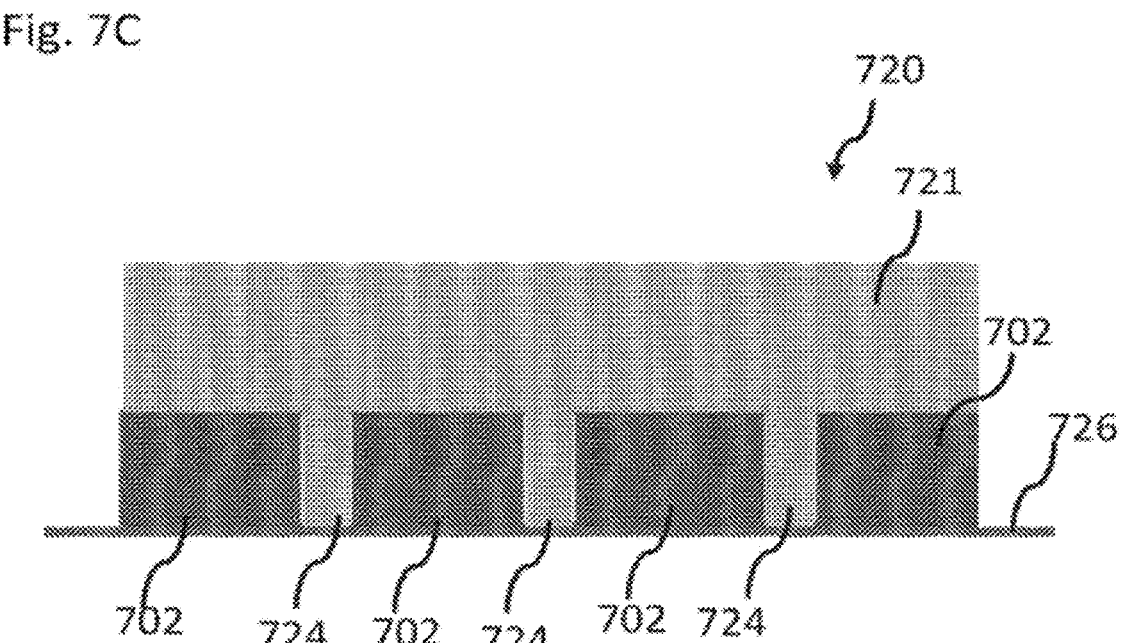
FIG. 7C is a schematic cross-section view of the assembly shown in FIG. 7B having cooling pillars passing through the openings in the ultrasound transducer, according to some exemplary embodiments of the invention.

According to some exemplary embodiments, for example as shown in FIG. 7C, a cooling basement 721 is attached to a surface of a PZT plate 702 having one or more channels, for example channels 704 and 706 shown in FIGS. 7A and 7B. In some embodiments, each channel is filled with a thermal conductive material, forming cooling basement pillars, for example thermal-conductive pillars 724 attached or part of a cooling basement 721. In some embodiments, filling the channels with thermal conducting materials, for example to form thermal conducting pillars, allows, a more efficient cooling of a tissue contacting the PZT plate compared to an assembly with empty pillars.

Figure 7D:
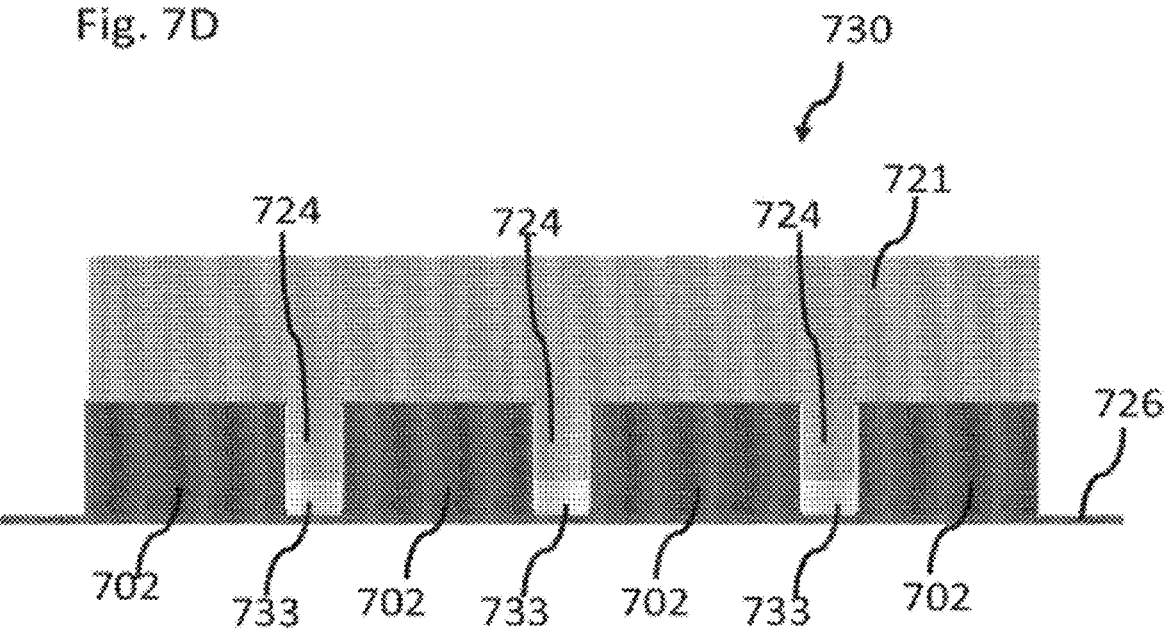
FIG. 7D is a schematic cross-section view of the assembly shown in FIG. 7C having low thermal conductivity elements between the cooling pillars and the external surface of the applicator, according to some exemplary embodiments of the invention.
Figure 7E:
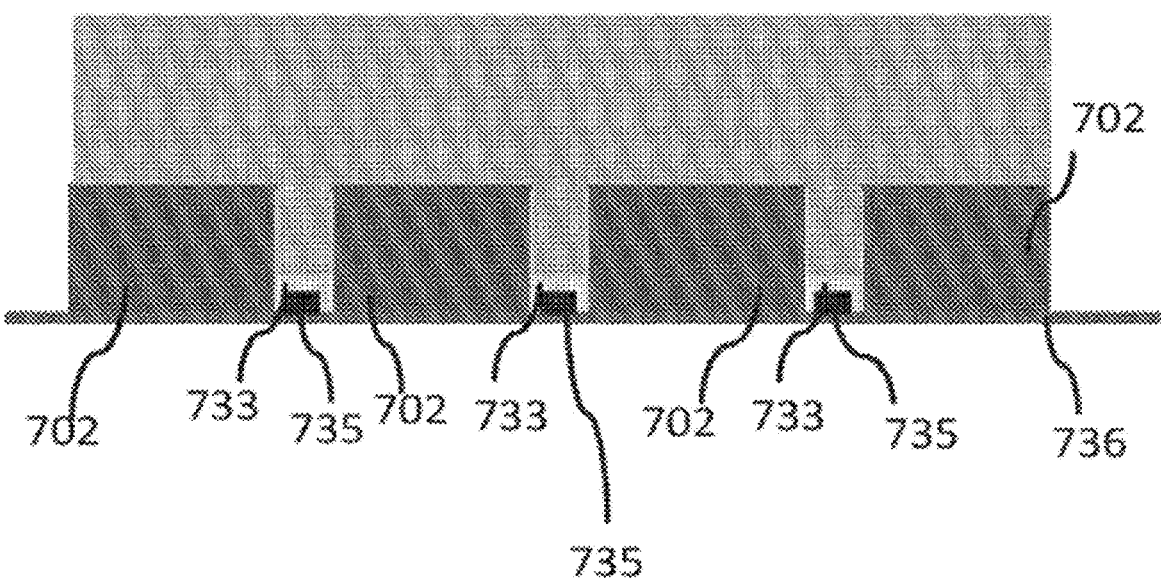
FIG. 7E is a schematic cross-section view of the assembly shown in FIG. 7D having one or more temperature sensors, according to some exemplary embodiments of the invention.

According to some exemplary embodiments, for example as shown in FIG. 7D, in assembly 730 at least some the channels crossing through the PZT plate 702 comprise a lower thermal conductivity material 733, between the thermal conductive pillars 724 and the flex PCB. In some embodiments, having less efficient thermal conductive material between the pillars 724 and the flex PCB which is placed in contact with the tissue allows, for example, to prevent over-cooling of the tissue. In some embodiments, for example as shown in FIG. 7E, the assembly 730 comprises one or more thermistors, for example thermistors 735 attached to the PCB. In some embodiments, the thermistors 735 are positioned within the channels of the PZT plate 702, optionally at least one thermistor per channel. In some embodiments, the thermistors are positioned near the contact of the flex PCB 736 with the tissue. Alternatively or additionally, the thermistors 735 are positioned within or near the lower thermal conductivity material 733. In some embodiments, the thermistors in the channels allow, for example, to monitor the temperature level of the PZT plate during the delivery of ultrasonic energy, and or to measure the temperature inside the channel, for example to determine the efficiency level of the cooling process. Additionally or alternatively, the thermistors monitor the temperature at the contact point between the PZT plate and the contacting tissue.

Exemplary Fat Layer Targeting

Figures 7F, 7G:
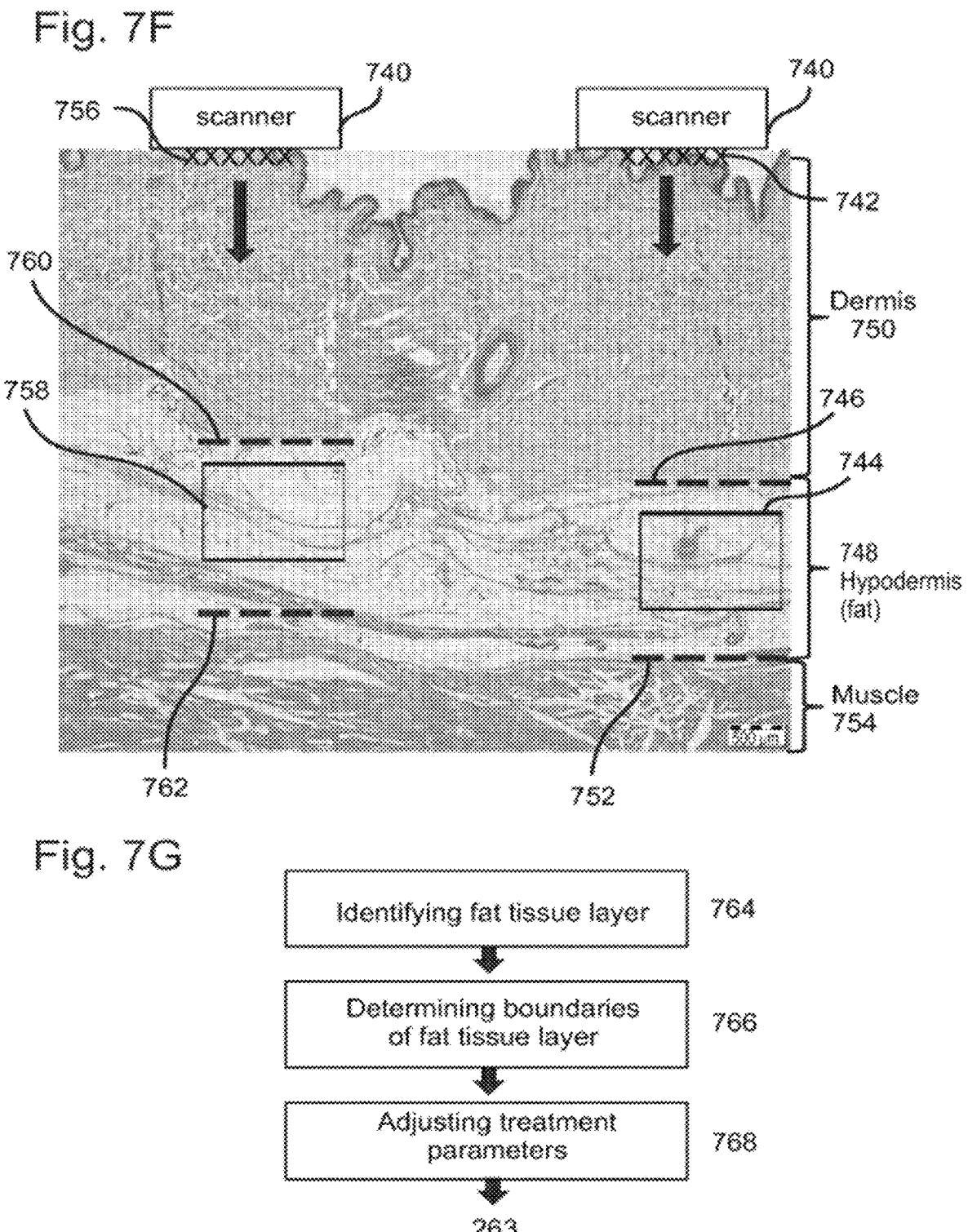
FIG. 7F is a histochemical cross-section image showing boundaries between the fat tissue layer, for example the hypodermis layer and adjacent tissue layers, according to some exemplary embodiments of the invention.
FIG. 7G is a flow chart of a process for targeting the fat tissue layer, according to some exemplary embodiments of the invention.

According to some exemplary embodiments, tissue at a selected anatomical location is analysed, for example to identify the fat layer, for example the hypodermis. In some embodiments, once the fat tissue layer is identified, treatment parameters are adjusted in order to target a selected tissue volume within the fat layer, optionally without causing damage to other tissue layers and/or organs near the selected tissue volume and/or near the fat tissue layer. Reference is now made to FIG. 7F depicting a schematic cross-section of different tissue layers of the skin, and FIG. 7G depicting a process for targeting fat tissue layer according to some exemplary embodiments of the invention.

According to some exemplary embodiments, a fat tissue layer is identified at block 764. In some embodiments, the fat tissue layer is identified by positioning a tissue scanner or a tissue sensor at a selected target location. In some embodiments, for example as shown in FIG. 7F, a scanner, for example an ultrasound scanner 740 is positioned at a selected target location on the skin, for example location 742. In some embodiments, the ultrasound scanner 740 is used to scan the tissue layers at the selected target location. In some embodiments, the scanner 740 is used to identify the fat tissue layer 748. Optionally, the scanner 740 is activated at an A-MODE, for example to identify the fat tissue layer 748.

According to some exemplary embodiments, boundaries of the fat tissue layer 748 are determined at block 766, for example using the scanner 740. In some embodiments, a border or an interface region between the fat tissue layer 748 and the dermis layer 750 is determined, for example using the scanner 740. Alternatively or additionally, a border or an interface region between the fat tissue layer 748 and the muscle layer 754 is determined, for example using the scanner 740. In some embodiments, a depth of the fat tissue layer 748 from the scanner or the external layer of the skin is calculated. In some embodiments, a width of the fat tissue layer 748 is calculated.

According to some exemplary embodiments, for example as shown in FIG. 7F, the fat tissue layer 748 is located at different depths from the epithelium layer, depending on a location of the external surface of the skin. In some embodiments, in location 742 on the external surface of the skin, the fat layer 748 is located at a larger depth from the epithelium, compared to the depth of the fat layer 748 from the epithelium in location 756. In some embodiments, a scanner 740 placed on the external surface of the skin, for example at a target location 742 identifies the fat tissue layer 748, and/or the border 744 of the fat tissue layer 748 with the dermis 750 and/or the border 752 of the fat tissue layer 748 with the muscle layer 754. Optionally, based on the borders detection, a width of the fat tissue layer at target location 742 is calculated.

According to some exemplary embodiments, when moving on the external surface of the skin to a different target location, for example target location 756, a depth of the fat tissue layer 748 from the epithelium changes. In some embodiments, a border 760 between the fat tissue layer 748 and the dermis 750 is located at a different depth relative to the border 746. In some embodiments, the border 762 between the fat tissue layer 748 and the muscle layer 754 is located at a different depth relative to the border 752. Optionally a width of the fat tissue layer 748 at location 756 is different from a width of the fat tissue layer at location 742.

According to some exemplary embodiments, a position of selected one or more target volumes, for example target volumes 744 and 758 in the fat tissue layer 748, is identified. In some embodiments, the depth of the one or more target volumes from the epithelium or any other reference point, is calculated.

According to some exemplary embodiments, one or more treatment parameters are adjusted according to the identified position of the fat tissue layer and/or determined borders of the fat tissue layer, at block 768. In some embodiments, one or more treatment parameters are adjusted at block 768, for example according to the identified position of one or more target volumes in the fat tissue layer. In some embodiments, one or more treatment parameters are adjusted according to a depth of the fat tissue layer from the epithelium layer or any other reference point, and/or a width of the fat tissue layer. In some embodiments, the treatment parameters comprise one or more of frequency of ultrasonic waves, intensity of ultrasonic waves, angle of one or more ultrasound transducers relative to a selected target volume.

According to some exemplary embodiments, the one or more treatment parameters are adjusted according to regulatory and/or safety limitations. In some embodiments, the one or more treatment parameters are changed automatically, for example by entering a name or coordinates of a selected location on the skin to a control unit, for example a control console of the applicator. In some embodiments, a memory of a control unit, for example memory 232 shown in FIG. 2A, stores one or more treatment parameter values or indications thereof, related to selected one or more anatomical locations or coordinates on the external surface of the skin.

According to some exemplary embodiments, the one or more treatment parameters are adjusted manually, for example following a scan of tissue layers, using one or more scanners, for example scanner 740. In some embodiments, a position sensor, a tissue sensor or any type of sensor in the ultrasound applicator used to deliver the ultrasound treatment, is used to identify the fat tissue layer, the borders with adjacent tissue layers, the depth of the fat tissue later from the skin surface and/or a width of the fat tissue layer at a selected location on the skin surface.

Exemplary Cellulite Treatment

Figure 7H:
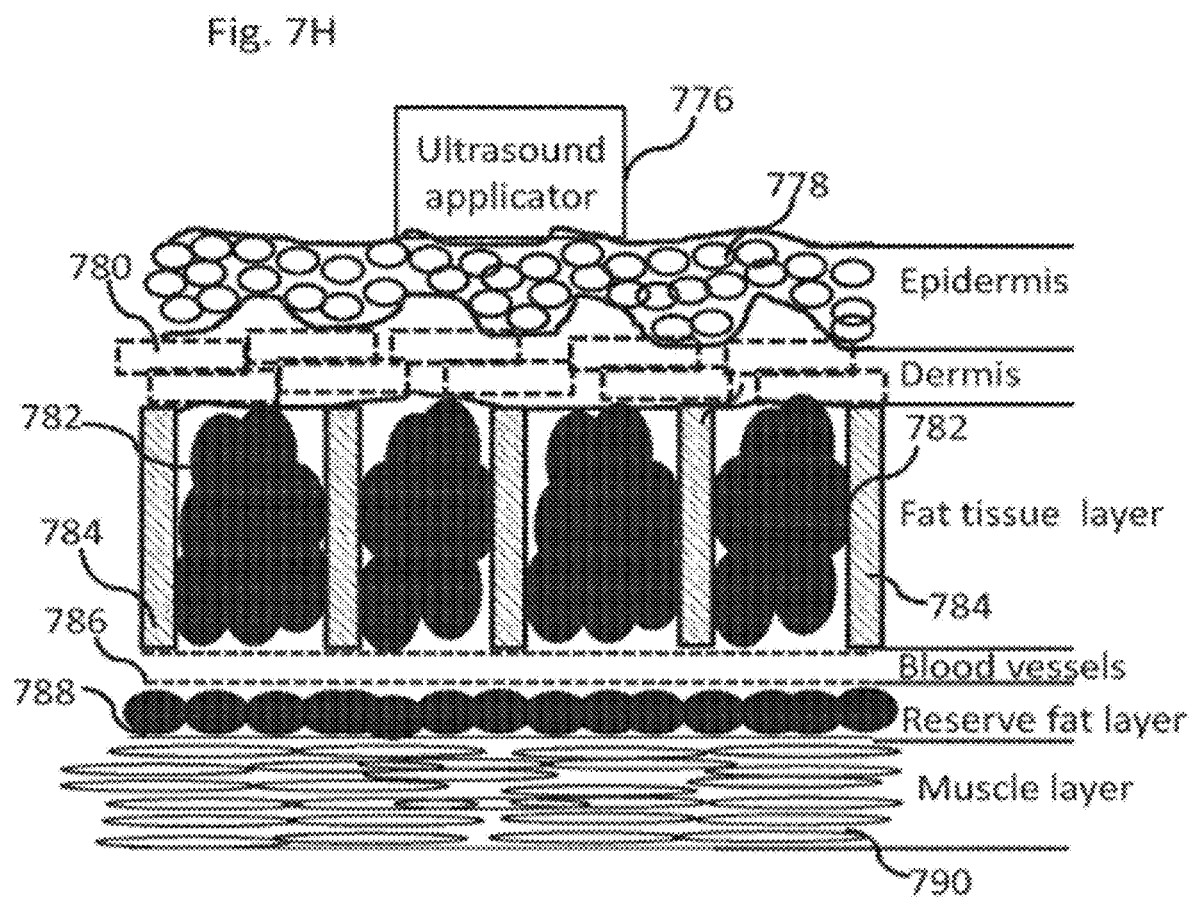

According to some exemplary embodiments, ultrasonic waves, for example unfocused ultrasonic waves, are used to treat cellulite. Reference is now made to FIG. 7H, depicting a schematic cross-section view of tissue layers at a cellulite-affected area of the body, according to some exemplary embodiments of the invention.

According to some exemplary embodiments, an ultrasound applicator, for example, applicator 776 is positioned on an external surface of the skin. In some embodiments, the applicator 776 delivers ultrasonic energy to different layers of the skin, for example to treat cellulite. In some embodiments, one or more of the cellulite treatment parameters are adjusted, for example to deliver ultrasonic energy, for example unfocused ultrasonic energy to different tissue layers. In some embodiments, the tissue layers comprise one or more of the layers, the epidermis comprising cells 778, the dermis which includes dermis cells 780, fat tissue layer which includes fat cells 782, optionally organized in clusters, and connective tissue 784 optionally located between adjacent fat cells clusters in the fat tissue layer, blood vessels 786 which deliver blood to the fat cells 782, a reserve fat layer which includes fat cells 788, and a muscle layer which includes muscle cells 790.

According to some exemplary embodiments, each of the layers is located at a different depth from the external surface of the skin.

According to some exemplary embodiments, in a cellulite treatment, ultrasonic waves, for example unfocused ultrasonic waves are delivered to the fat tissue layer, for example to affect fat cells and/or connective tissue. Additionally or optionally, in the cellulite treatment, the ultrasonic waves are delivered to the dermis and/or epidermis layer, for example as part of a complementary skin tightening treatment. In some embodiments, the ultrasonic waves are delivered to the epidermis and/or dermis.

According to some exemplary embodiments, in a cellulite treatment, ultrasonic waves, for example unfocused ultrasonic waves, are delivered to blood vessels 786, providing blood to the fat cells in the fat tissue layer. In some embodiments, the ultrasonic waves are delivered to the blood vessels 786.

According to some exemplary embodiments, in a cellulite treatment, ultrasonic waves, for example unfocused ultrasonic waves are delivered to the reserved fat layer.

According to some exemplary embodiments, in a cellulite treatment, ultrasonic waves, for example unfocused ultrasonic waves are delivered to the muscle layer. In some embodiments, the ultrasonic waves are delivered to the muscle layer.

Exemplary Simulations

Several simulations were performed in order to determine frequency, intensity and duration parameter values of ultrasonic energy delivery, in order to reach a temperature level in a range of 52-57° C. for a time duration of at least 5 seconds within a selected tissue volume.

Table A below summarizes the treatment parameter values when delivering ultrasonic waves with a frequency of 2 MHz:

TABLE A

| Intensity [W/cm^2] | Excitation duration [sec] | Fat temp. range [° C.] | Duration at temp. range [sec] | ~Pick temp. depth [mm] |
|---|---|---|---|---|
| 10 | 42 | 52-57 | 5 | 6.0 |
| 12 | 35 | 52-57 | 5 | 5.7 |
| 14 | 30 | 52-57 | 5 | 5.4 |
| 16 | 25 | 52-57 | 5 | 5.0 |
| 20 | 20 | 52-57 | 5 | 4.7 |
| 22 | 18 | 52-57 | 5 | 4.6 |
| 24 | 16 | 52-57 | 5 | 4.5 |
| 26 | 15 | 52-57 | 5 | 4.4 |
| 28 | 14 | 52-57 | 5 | 4.3 |
| 30 | 13 | 52-57 | 5 | 4.2 |

Figure 8A:
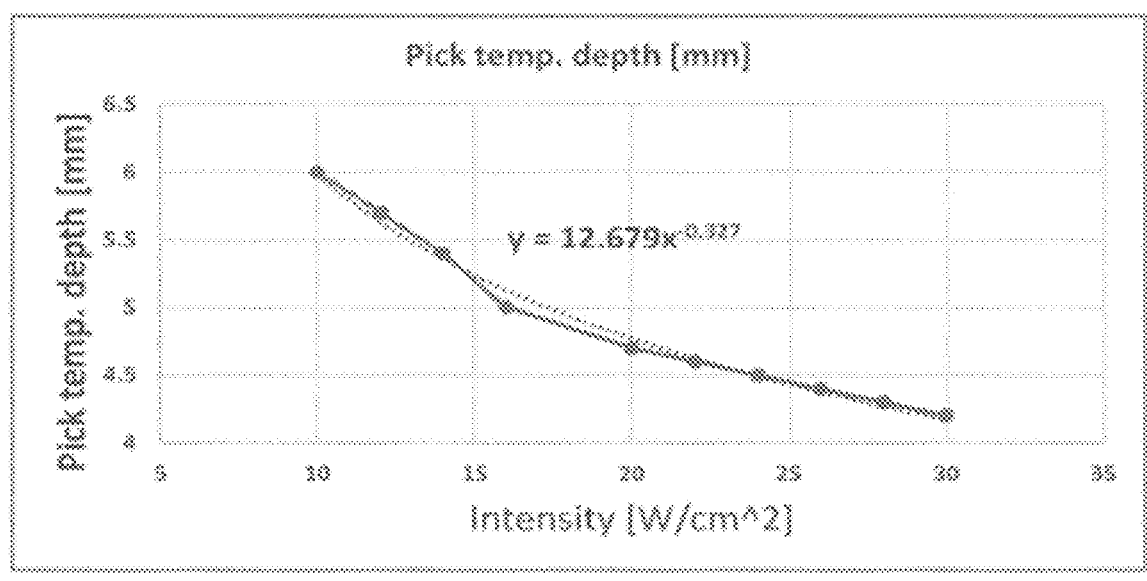
FIG. 8A is a graph of simulation results, according to some exemplary embodiments of the invention.

FIG. 8A describes a relation between intensity levels and the depth in which a peak in the temperature is measured.

Figure 8B:
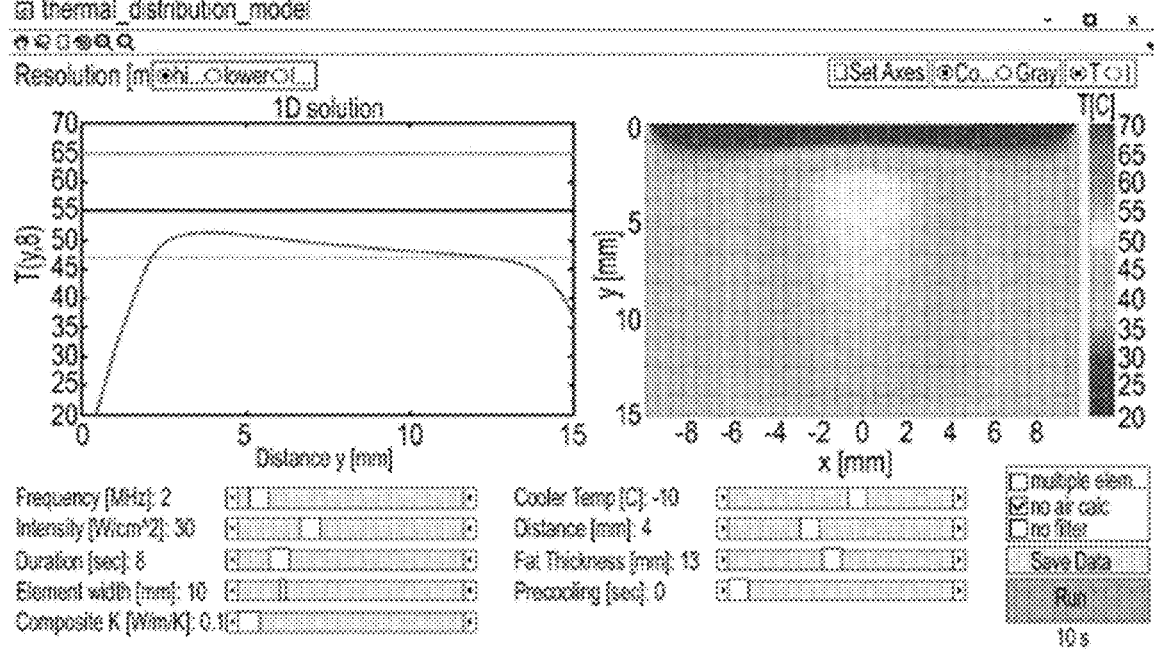
FIGS. 8B to 8E are simulation results when emitting ultrasonic waves in a frequency of 2 MHz, according to some exemplary embodiments of the invention.
Figure 8C:
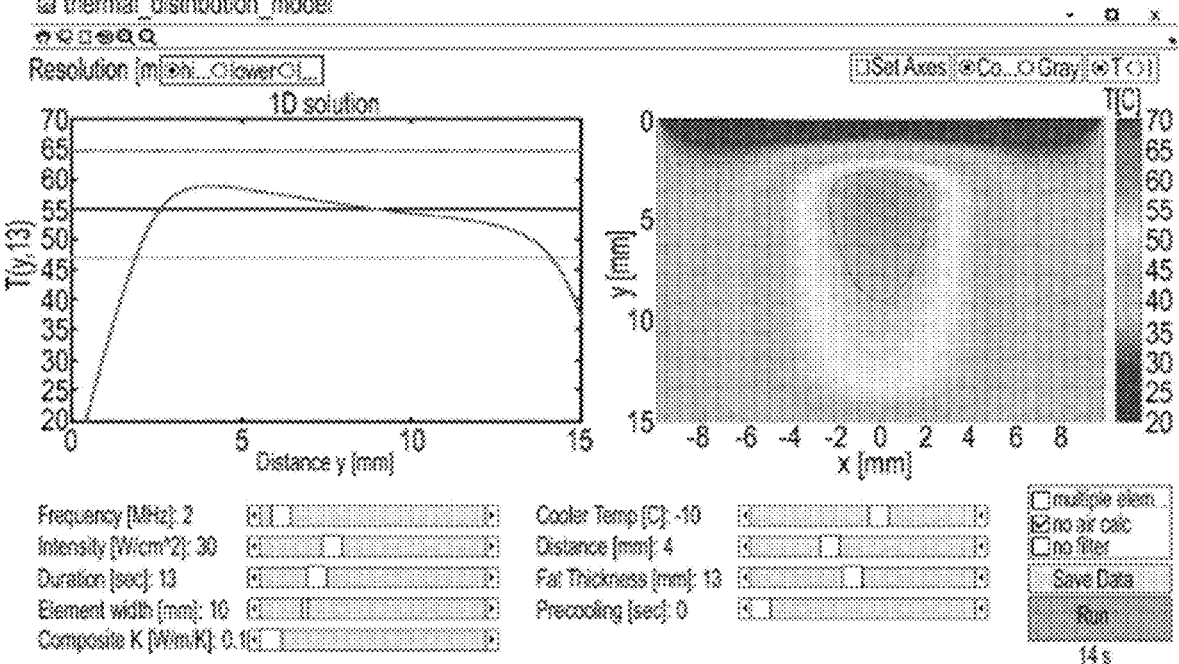

FIG. 8B describes simulation results obtained when using a frequency of 2 MHZ, intensity levels of 30 w/cm² for 8 seconds. FIG. 8C describes simulation results when using the parameter values as in FIG. 8B for a time period of 13 seconds. As shown in FIG. 8C, the temperature in the last 5 seconds of the simulation was in a range between 52-57° C.

Figure 8D:
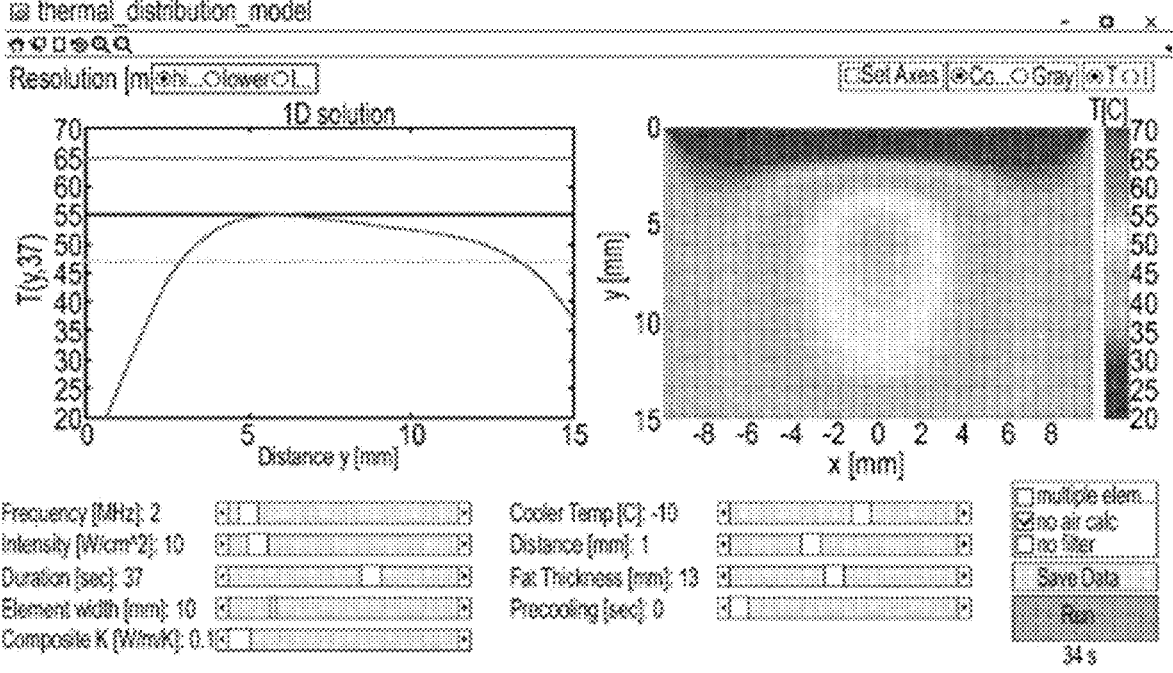
Figure 8E:
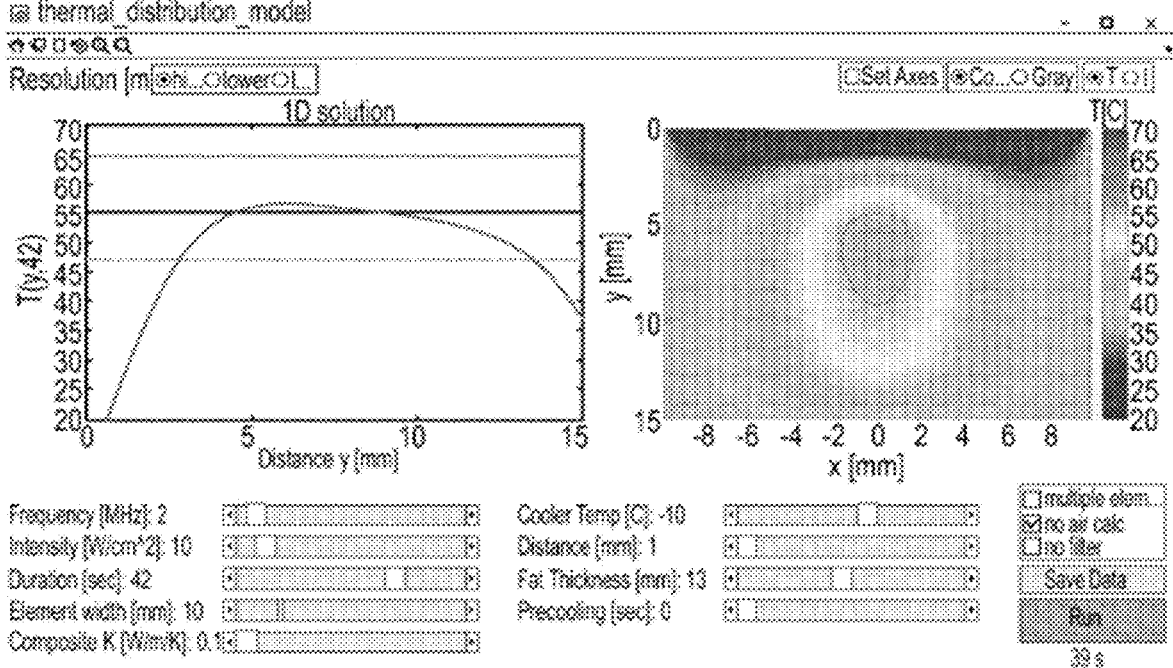

FIG. 8D describes simulation results obtained when using a frequency of 2 MHZ, intensity levels of 10 w/cm² for 37 seconds. FIG. 8E describes simulation results when using the parameter values as in FIG. 8D for a time period of 42 seconds. As shown in FIG. 8E, the temperature in the last 5 seconds of the simulation was in a range between 52-57° C.

Table B below summarizes the treatment parameter values when delivering ultrasonic waves with a frequency of 5 MHz:

TABLE B

| Intensity [W/cm^2] | Excitation duration [sec] | Fat temp. range [° C.] | Duration at temp. range [sec] | ~Pick temp. depth [mm] |
|---|---|---|---|---|
| 10 | 18 | 52-57 | 5 | 3.6 |
| 12 | 15 | 52-57 | 5 | 3.4 |
| 14 | 13 | 52-57 | 5 | 3.2 |
| 16 | 11 | 52-57 | 5 | 3.0 |

Figure 9A:
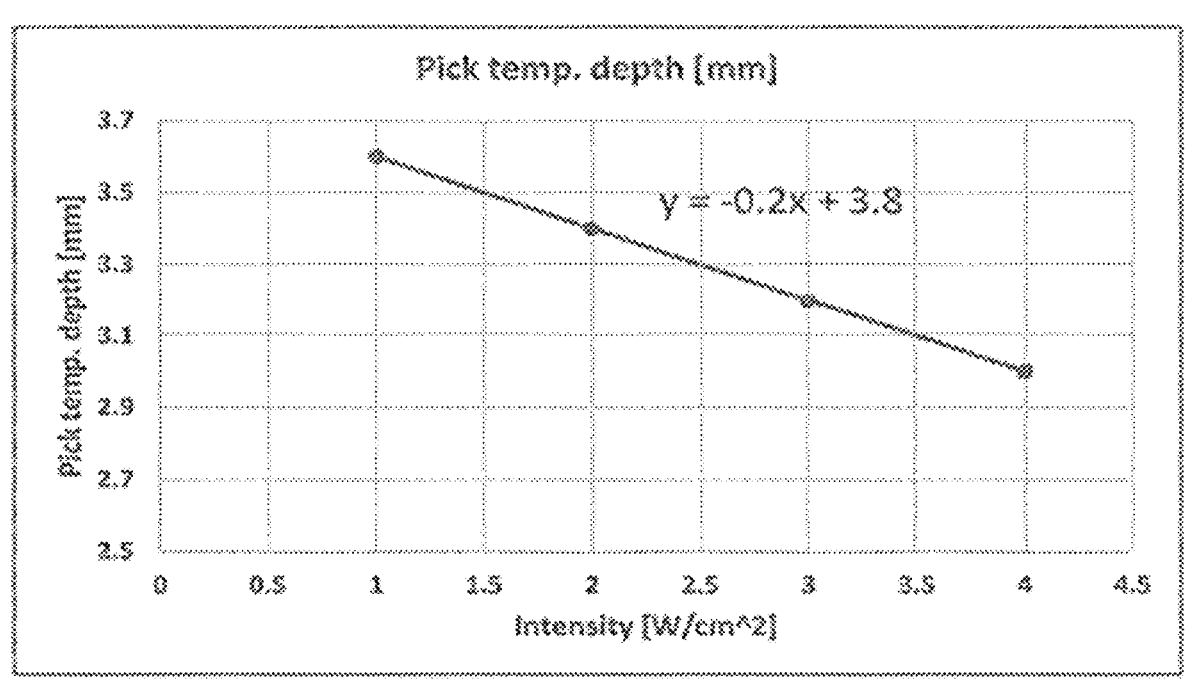
FIG. 9A is a graph of simulation results, according to some exemplary embodiments of the invention.

FIG. 9A describes a relation between intensity levels and the depth in which a peak in the temperature is measured.

Figure 9B:
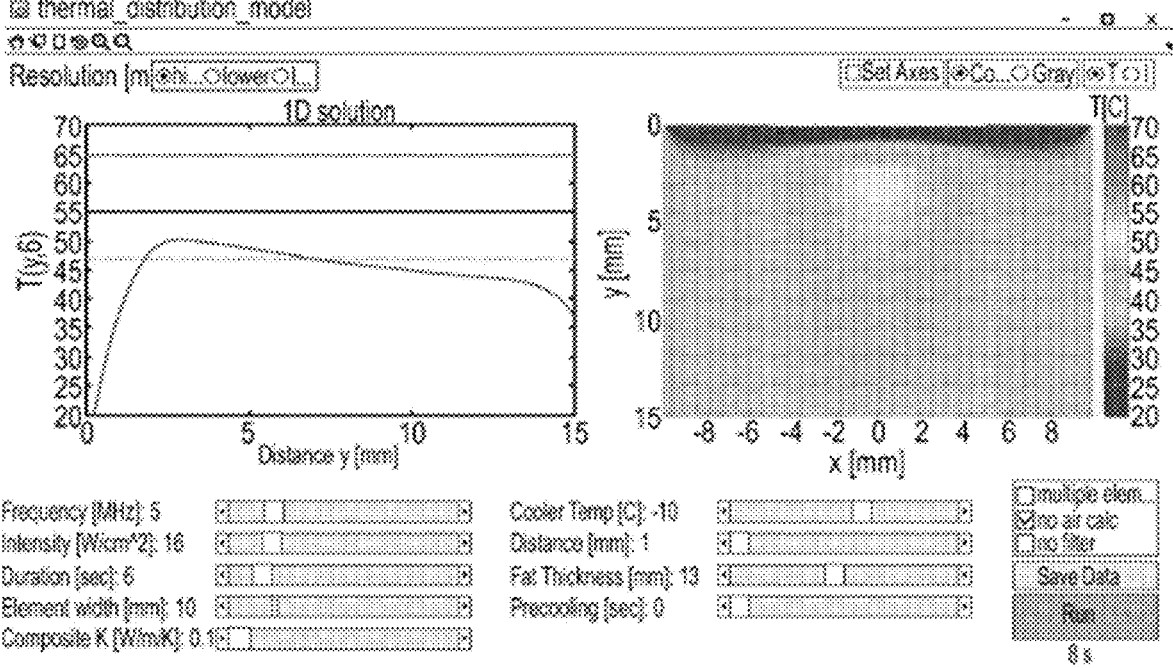
FIGS. 9B to 9E are simulation results when emitting ultrasonic waves in a frequency of 5 MHz, according to some exemplary embodiments of the invention.
Figure 9C:
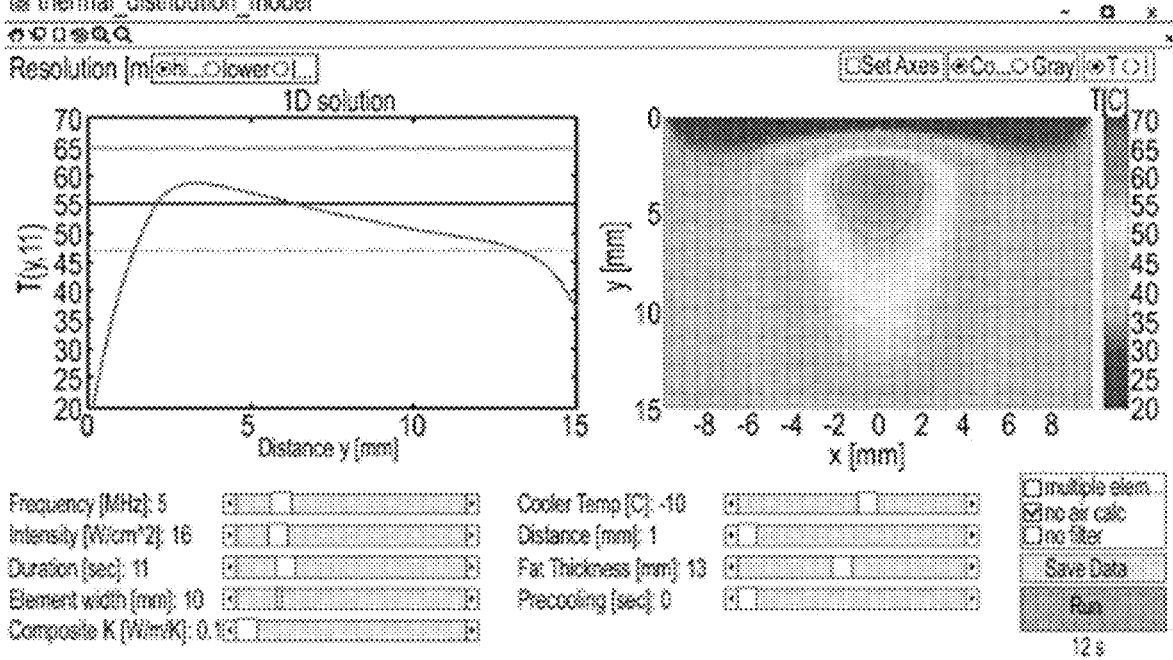

FIG. 9B describes simulation results obtained when using a frequency of 5 MHz, intensity levels of 16 w/cm² for 6 seconds. FIG. 9C describes simulation results when using the parameter values as in FIG. 9B for a time period of 11 seconds. As shown in FIG. 9C, the temperature in the last 5 seconds of the simulation was in a range between 52-57° C.

Figure 9D:
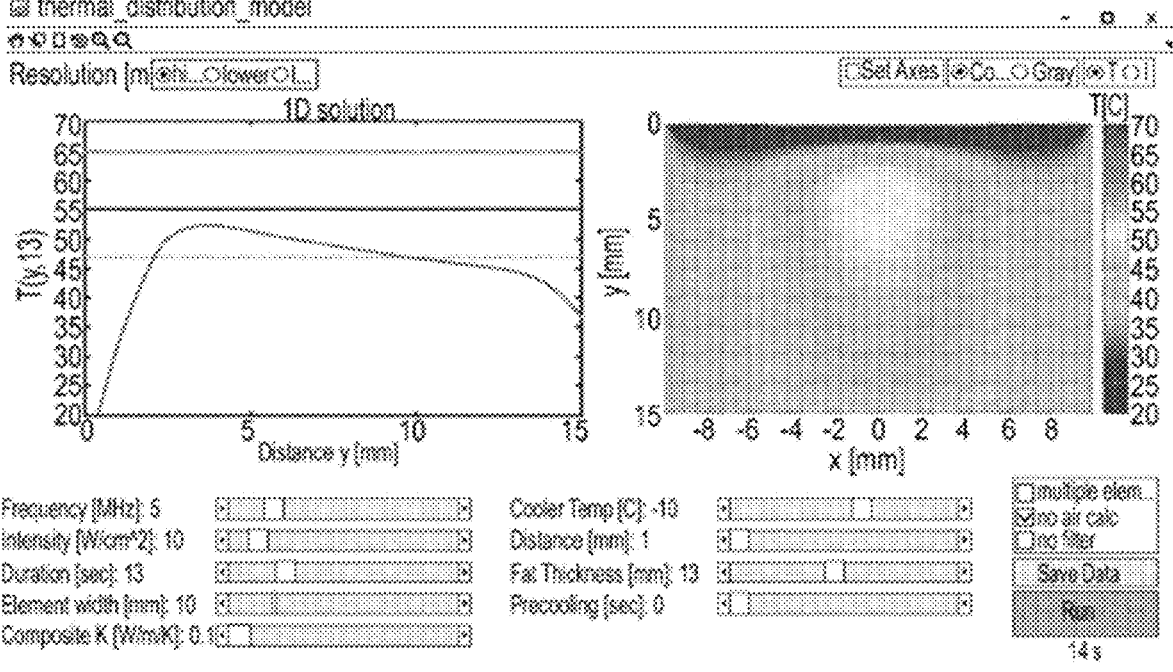
Figure 9E:
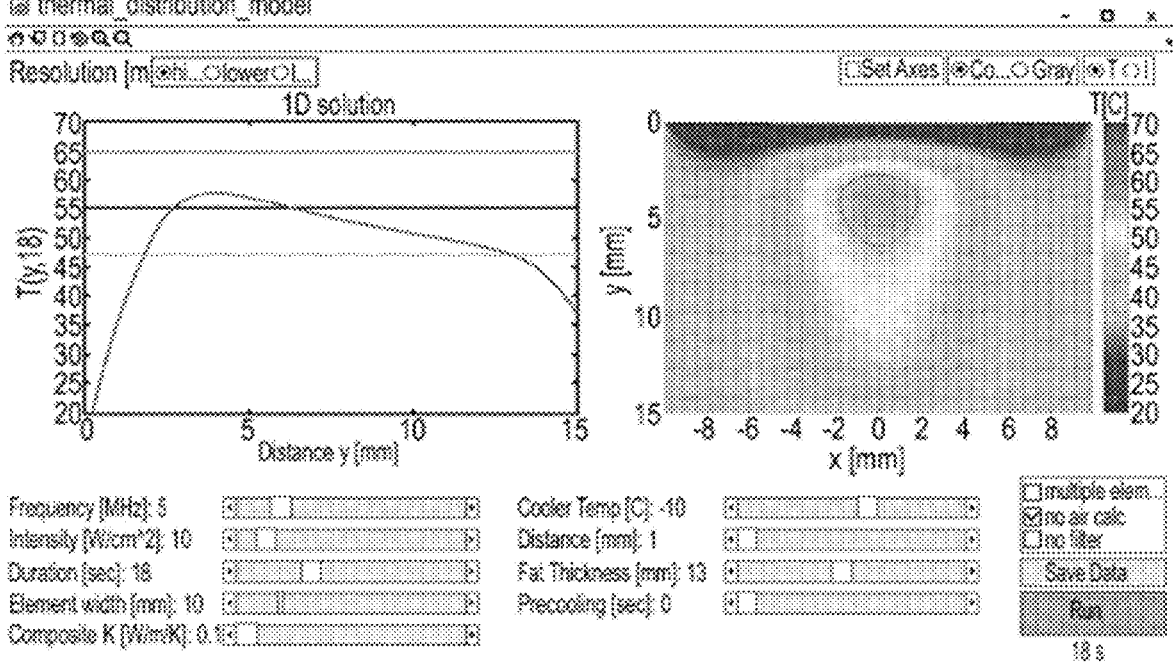

FIG. 9D describes simulation results obtained when using a frequency of 5 MHz, intensity levels of 10 w/cm² for 13 seconds. FIG. 9E describes simulation results when using the parameter values as in FIG. 9D for a time period of 18 seconds. As shown in FIG. 9E, the temperature in the last 5 seconds of the simulation was in a range between 52-57° C.

Exemplary Treatment

According to some exemplary embodiments, a treatment for reducing fat and/or cellulite, which is optionally part of a body contouring treatment, is delivered to a subject at a selected treatment region.

According to some exemplary embodiments, a subject to undergo a body contouring treatment, for example a fat and/or cellulite reduction treatment is selected. In some embodiments, the subject is selected based on one or more subject selection parameters comprising subject age, current clinical condition, medical history, drug regime, sensitivity of the subject to pain, high heat and/or cold levels.

Experiment

An experiment was performed to test the efficacy of a fat tissue treatment. In the experiment and in some embodiments of the invention, subjects are selected based on one or more characteristics, for example age, gender, current clinical condition, medical history, and/or sensitivity of the subject to heat and cold. In the experiment and in some embodiments of the invention, subjects were evaluated 1-3 months, for example 1-2 months, 1.5-2.5 months, 2-3 months or any intermediate, shorter or longer time period.

In the experiment and in some embodiments of the invention, the ultrasonic waves frequency was in a range of 10-13 Mhz, for example 10.5-12 MHz, 11-12 Mhz, 11.5-12.5 Mhz, 11.5 Mhz or any intermediate, smaller or larger value or range of values. In the experiment and in some embodiments of the invention, at least part of a surface of an ultrasound applicator placed in contact with the skin of a subject, was cooled to a temperature in a range of −5° C. to −15° C., for example −5° C. to −10° C., −8° C. to −15° C. or any intermediate, smaller or larger range of temperatures.

In the experiment and in some embodiments of the invention, a subject received ultrasonic waves to the Chin, with an intensity levels in a range of 3-4.2 Joules. In some embodiments, 1 Joule of energy delivered to the tissue equals 5 cm^2. In the experiment and in some embodiments of the invention, the ultrasonic waves to the Chin were delivered in a series of 4 pulses, 2-7 pulses, for example 2-5 pulses, 4-6 pulses, 5-7 pulses, or any intermediate, smaller or larger range of pulses or number of pulses. In the experiment and in some embodiments of the invention, a time duration of each pulse was 5 seconds or in a range of 3-6 seconds, for example 3-5 seconds, 4-5.5 seconds, 4-6 seconds, or any intermediate, shorter or longer time duration.

In the experiment and in some embodiments of the invention, a subject received ultrasonic waves to the neck, for example to the submental and/or right neck with an intensity levels in a range of 3-4.2 Joules. In the experiment and in some embodiments of the invention, the ultrasonic waves to the to the neck, for example to the submental and/or right neck were delivered in a series of 32 pulses, 20-40 pulses, for example 20-35 pulses, 30-40 pulses, 25-35 pulses, or any intermediate, smaller or larger range of pulses or number of pulses. In the experiment and in some embodiments of the invention, a time duration of each pulse was 5 seconds or in a range of 3-6 seconds, for example 3-5 seconds, 4-5.5 seconds, 4-6 seconds, or any intermediate, shorter or longer time duration.

In the experiment and in some embodiments of the invention, a subject received ultrasonic waves to the neck, for example to the left neck with an intensity levels in a range of 3-4.2 Joules. In the experiment and in some embodiments of the invention, the ultrasonic waves to the to the neck, for example to the left neck were delivered in a series of 22 pulses, 10-40 pulses, for example 20-35 pulses, 30-40 pulses, 25-35 pulses, or any intermediate, smaller or larger range of pulses or number of pulses. In the experiment and in some embodiments of the invention, a time duration of each pulse was 5 seconds or in a range of 3-6 seconds, for example 3-5 seconds, 4-5.5 seconds, 4-6 seconds, or any intermediate, shorter or longer time duration. In some embodiments, fewer pulses of ultrasonic waves are delivered to the left neck compared to the number of pulses derived to the right neck.

In the experiment and in some embodiments of the invention, images of the treated region are taken at an evaluation meeting or at the home of the subject, 2 months, 3 months, 1 week-6 months following the treatment, for example 2 weeks, 1 month, 2 months, 3 months or any intermediate, shorter or longer time duration following the treatment. In the experiment and in some embodiments of the invention, the images are analyses using an analysis software to detect changes following the treatment. In the experiment and in some embodiments of the invention, the analysis is performed using a system of Cherry Imaging™ (www(dot)cherryimaging(dot)com/).

Figure 10A:
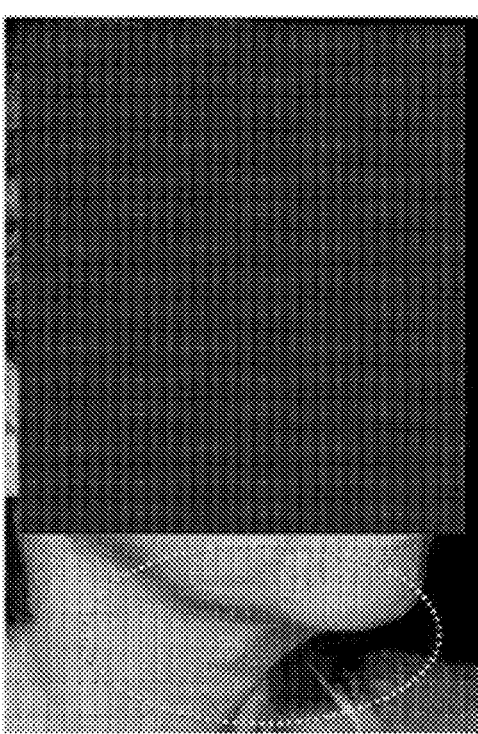
Figure 10B:
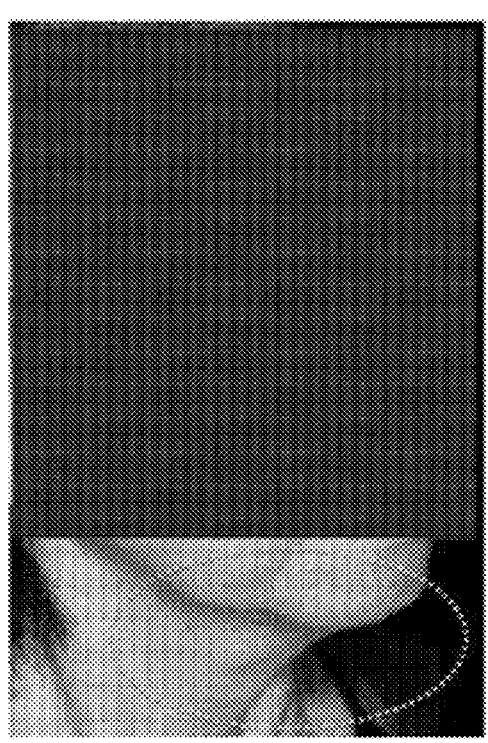
Figure 10C:
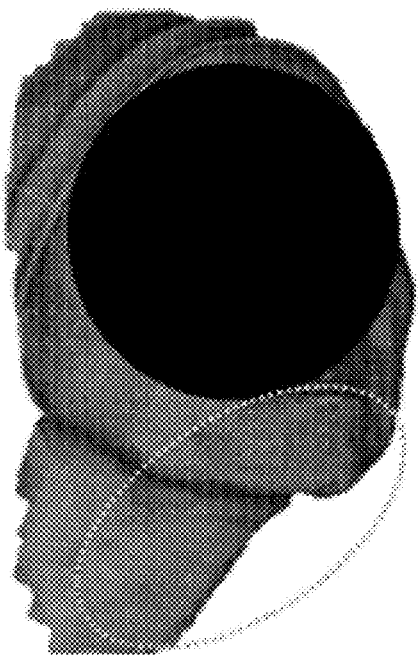
Figure 10D:
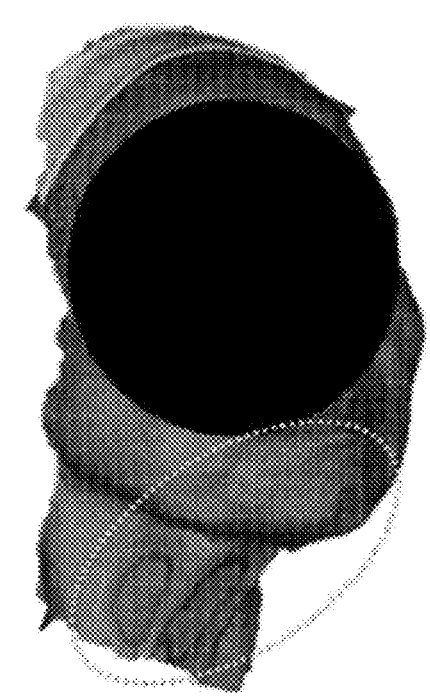
Figure 10E:
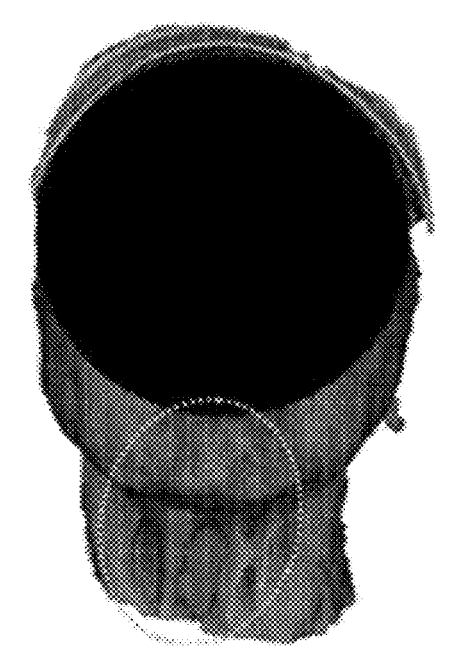

Reference is now made to FIGS. 10A-10E depicting tissue changes in a female subject following treatment as part of the experiment, of the Chin, Right Neck, Submental regions and the Left neck. FIGS. 10B and 10D describe changes in the shape and volume of tissue in the neck 3 months following the treatment, compared to base line FIGS. 10A and 10C respectively. Comparison of 10D to 10C using the cherry imaging system reveals a volume reduction of about 10.76 Cubic Centimeter (CC) following the treatment, as can also be seen in FIG. 10E.

Figure 11A:
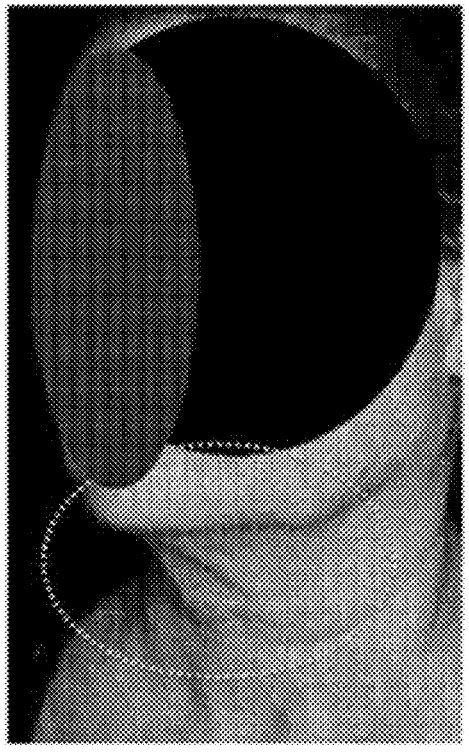
Figure 11B:
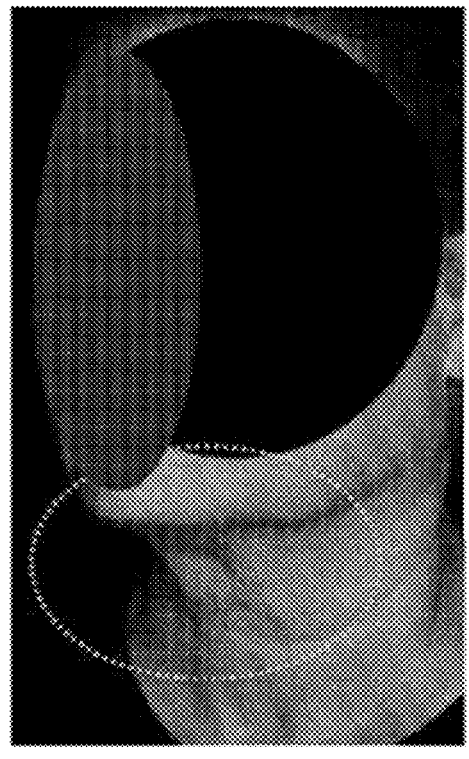
Figure 11C:
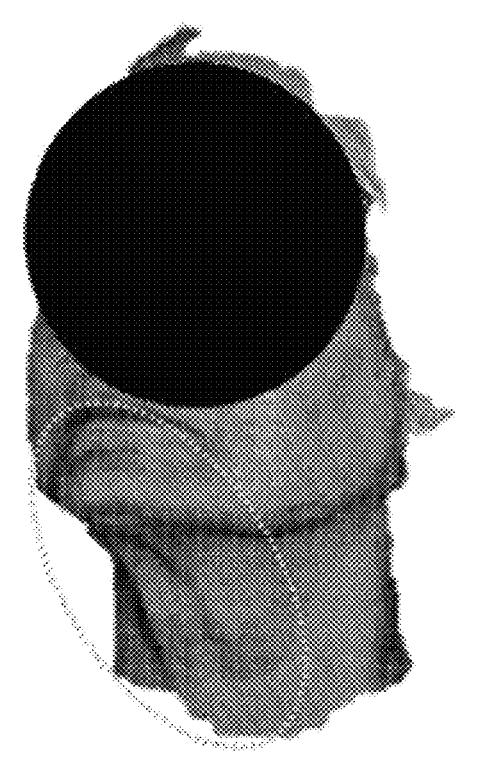
Figure 11D:
Figure 11D:
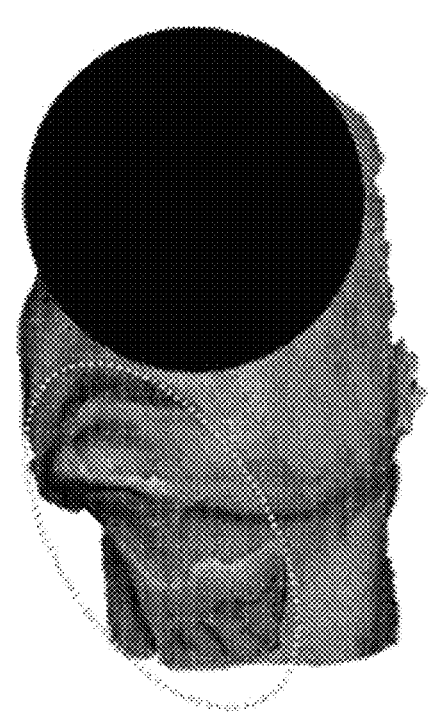

Reference is now made to FIGS. 11A-11D, depicting tissue changes in a female subject following treatment as part of the experiment, of the Right Neck, Submental regions and the Left neck. FIGS. 11B and 11D describe changes in the shape and volume of tissue in the neck, 3 months following the treatment, compared to base line FIGS. 11A and 11C respectively. Comparison of 11D to 11C using the cherry imaging system reveals a volume reduction of about 8.76 CC following the treatment.

Figure 12A:
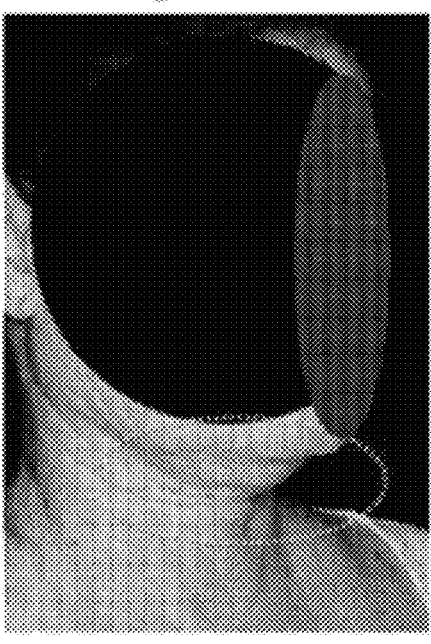
Figure 12B:
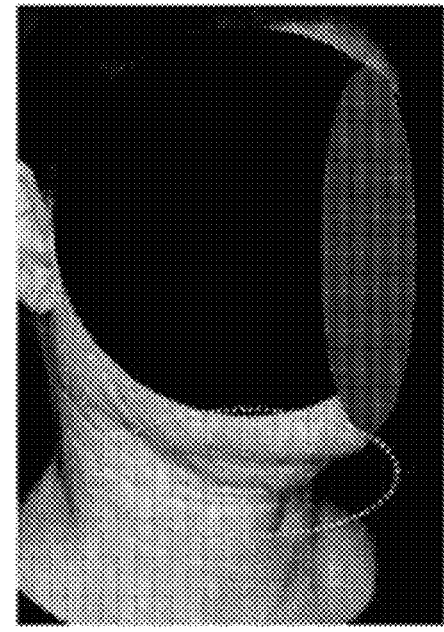
Figure 12C:
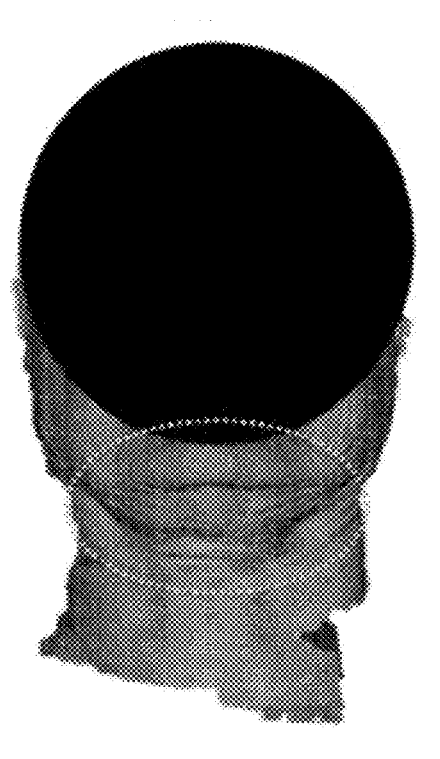
Figure 12D:
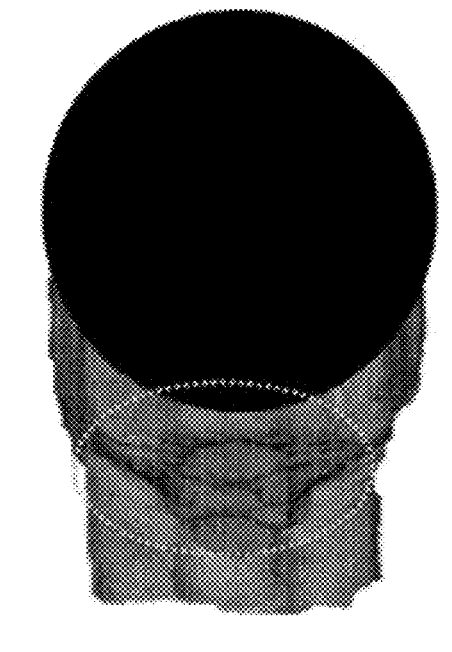

Reference is now made to FIGS. 12A-12D, depicting tissue changes in a female subject following treatment as part of the experiment, of the Right Neck, Submental regions and the Left neck. FIGS. 12B and 12D describe changes in the shape and volume of tissue in the neck, 3 months following the treatment, compared to base line FIGS. 12A and 12C respectively. Comparison of 12D to 12C using the cherry imaging system reveals a volume reduction of about 22.22 CC following the treatment.

Figure 13A:
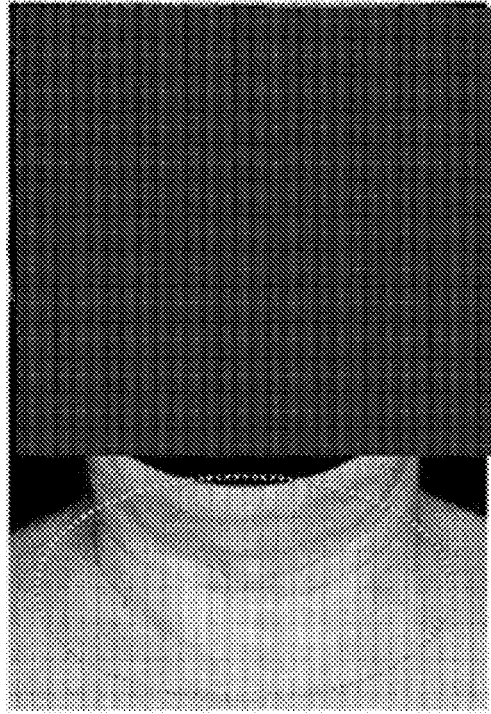
Figure 13B:
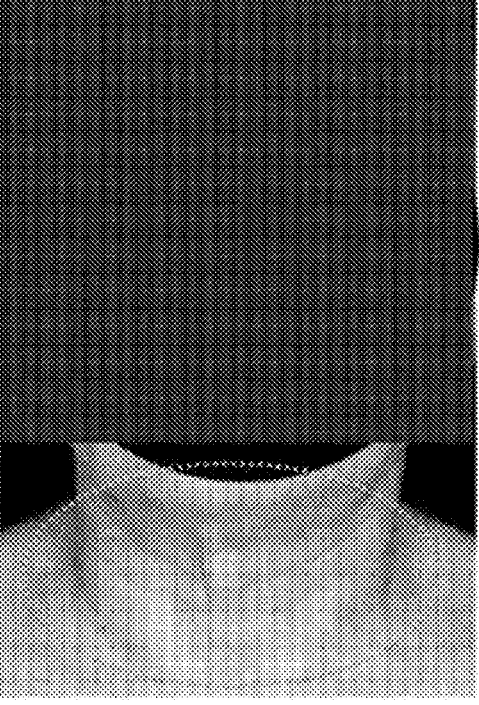

Reference is now made to FIGS. 13A-13D, depicting tissue changes in a male subject following treatment as part of the experiment, of the Right Neck, Submental regions and the Left neck. FIGS. 13B and 13D describe changes in the shape and volume of tissue in the neck, 3 months following the treatment, compared to base line FIGS. 13A and 13C respectively. Comparison of 13D to 13C using the cherry imaging system reveals a volume reduction of about 26.47 CC following the treatment.

It is expected that during the life of a patent maturing from this application many relevant ultrasound transducers will be developed; the scope of the term ultrasound transducer is intended to include all such new technologies a priori.

As used herein with reference to quantity or value, the term "about" means "within +10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A system for fat tissue treatment, the system comprising:

a plurality of piezoelectric (PZT) plates configured to generate ultrasound waves;

a plurality of electrical connections associated with each of plurality of PZT plates, wherein the plurality of PZT plates and the plurality of electrical connections form a plurality of ultrasound transducers;

one or more joints interconnecting the plurality of ultrasound transducers side-by-side in a linear arrangement to allow relative movement of at least some of the plurality of ultrasound transducers to conform to a contour of a treatment region, the treatment region including at least one of an abdomen, a thigh, or a buttocks;

a strap configured to fasten the plurality of ultrasound transducers to the treatment region, such that the strap and the ultrasound transducers form a belt-shaped ultrasound applicator; and electrical circuitry configured to cause controlled emission of ultrasonic waves via the belt-shaped ultrasound applicator with intensity values in a range of 5-90 W/cm² and frequency values in a range of 1-7 MHz to deliver ultrasonic energy to fat tissue at a depth of 2-20 mm beneath a skin surface of the treatment region to thereby heat the fat tissue to a temperature between 45° C. and 85° C.

2. The system of claim 1, wherein a number of ultrasound transducers in the linear arrangement is adjustable based on the treatment region.

3. The system of claim 1, wherein the plurality of ultrasound transducers includes at least four ultrasound transducers.

4. The system of claim 1, wherein the plurality of ultrasound transducers includes at least six ultrasound transducers.

5. The system of claim 1, wherein the electrical circuitry is further configured to activate two or more of the plurality of ultrasound transducers in alternation according to a sequence stored in memory.

6. The system of claim 1, wherein a thickness of each of the plurality of ultrasound transducers is in a range of 0.1 mm to 7 mm.

7. The system of claim 1, wherein the plurality of ultrasound transducers are configured to transmit the ultrasonic waves through a cover in contact with the skin surface.

8. The system of claim 1, wherein the electrical circuitry is further configured to cause the PZT plates to generate ultrasonic waves that are not focused to converge in two dimensions.

9. The system of claim 1, wherein the electrical circuitry is further configured to cause the PZT plates to generate ultrasonic waves having intensity values in a range of 40-90 W/cm² and frequency values in a range of 1-5 MHz.

10. The system of claim 1, wherein the electrical circuitry is further configured to cause the PZT plates to generate ultrasonic waves for delivering energy in a range of 1 to 18 Joules to the fat tissue.

11. The system of claim 1, wherein the electrical circuitry is further configured to determine a depth of the fat tissue relative to the skin surface.

12. The system of claim 1, wherein the electrical circuitry is further configured to generate ultrasonic waves targeted to different tissue layers.

13. The system of claim 12, wherein the electrical circuitry is further configured to combine fat reduction treatment with skin tightening treatment.

14. The system of claim 1, wherein the electrical circuitry includes at least one processor configured to control the emission of ultrasonic waves via the plurality of PZT plates.

15. A method for fat tissue treatment, the method comprising:

placing a plurality of interconnected ultrasound transducers in a side-by-side linear arrangement on a non-flat tissue surface of epidermis, the non-flat tissue surface being associated with at least one of an abdomen, a thigh, or a buttocks, wherein each of the plurality of ultrasound transducers include at least one piezoelectric (PZT) plate, and wherein the plurality of ultrasound transducers are connected in series in a manner permitting the linear arrangement to flex in accordance with a contour of the non-flat tissue surface;

fastening the plurality of ultrasound transducers to the non-fat tissue surface with a strap, such that the strap and the ultrasound transducers form a belt; and causing controlled emission of ultrasonic waves via the plurality of PZT plates with intensity values in a range of 5-90 W/cm² and frequency values in a range of 1-7 MHz to deliver ultrasonic energy to fat tissue at a depth of 2-20 mm beneath a skin surface of the treatment region to thereby heat the fat tissue to a temperature between 45° C. and 85° C.

16. The method of claim 15, wherein causing the controlled emission includes setting at least one of intensity values or frequency values of the ultrasonic waves according to an estimated depth of the fat tissue.

17. The method of claim 15, wherein causing the controlled emission includes activating at least one ultrasound transducer of the plurality of ultrasound transducers, while at least one other of the ultrasound transducers remain inactive.

18. The method of claim 15, wherein causing the controlled emission includes activating the at least some of the PZT plates for a duration of at least two seconds without causing damage to adjacent tissue layers near the fat tissue.

19. The method of claim 15, wherein causing the controlled emission includes activating the plurality of PZT plates in alternation to continuously heat the fat tissue while keeping a temperature of the skin surface of the treatment region below a predetermined value.

20. A non-transitory computer readable medium containing instructions that when executed by at least one processor cause the at least one processor to perform operations for fat tissue treatment, the operations comprising:

activating a plurality of piezoelectric (PZT) plates associated with a plurality of electrical connections, wherein the plurality of PZT plates and the plurality of electrical connections form a plurality of ultrasound transducers flexibly connected side-by-side in a linear arrangement to allow relative movement of at least some of the plurality of ultrasound transducers to conform to a contour of a treatment region, the treatment region including at least one of an abdomen, a thigh, or a buttocks; and causing controlled emission of ultrasonic waves via the plurality of PZT plates with intensity values in a range of 5-90 $W/cm^2$ and frequency values in a range of 1-7 MHz to deliver ultrasonic energy to fat tissue at a depth of 2-20 mm beneath a skin surface of the treatment region while at least some of the plurality of ultrasound transducers conform to the contour of the treatment region, to thereby heat the fat tissue to a temperature between 45° C. and 85° C.

\* \* \* \* \*